United States Patent [19]
Reichard et al.

[11] Patent Number: 5,840,725
[45] Date of Patent: Nov. 24, 1998

[54] SUBSTITUTED OXIMES, HYDRAZONES AND OLEFINS AS NEUROKININ ANTAGONISTS

[75] Inventors: Gregory A. Reichard, Morris Plains; Robert G. Aslanian, Rockaway; Cheryl A. Alaimo, Somerset; Michael P. Kirkup, Lawrenceville; Andrew Lupo, Jr., Emerson, all of N.J.; Pietro Mangiaracina, Monsey, N.Y.; Kevin D. McCormick, Edison, N.J.; John J. Piwinski, Clinton Township, N.J.; Bandarpalle B. Shankar, Branchburg, N.J.; Neng-Yang Shih, North Caldwell, N.J.; James M. Spitler, Westfield, N.J.; Pauline C. Ting, New Providence, N.J.; Ashit Ganguly, Upper Montclair, N.J.; Nicholas I. Carruthers, North Plainfield, N.J.

[73] Assignee: Schering Corporation, Kenilworth, N.J.

[21] Appl. No.: 901,028

[22] Filed: Jul. 25, 1997

Related U.S. Application Data

[62] Division of Ser. No. 641,384, Apr. 30, 1996, Pat. No. 5,696,267, Continuation-in-part of Ser. No. 460,819, Jun. 1, 1995, abandoned, which is a continuation-in-part of Ser. No. 432,740, May 2, 1995, abandoned.

[51] Int. Cl.[6] ........................ A61K 31/495; C07D 403/06
[52] U.S. Cl. .................... 514/252; 544/372; 544/392; 544/398; 544/402; 514/238.5; 514/255
[58] Field of Search ...................... 544/372, 392, 544/398, 402, 121, 139, 162; 514/238.5, 252, 255

[56] References Cited

U.S. PATENT DOCUMENTS

| 4,337,252 | 6/1982 | Astoin | 424/248.57 |
| 5,350,852 | 9/1994 | Emonds-Alt et al. | 544/336 |

FOREIGN PATENT DOCUMENTS

| 630887 | 12/1994 | European Pat. Off. |
| 0 680 962 | 11/1995 | European Pat. Off. |
| 0 699 674 | 3/1996 | European Pat. Off. |
| 2717802 | 9/1995 | France. |
| 2274777 | 8/1994 | United Kingdom. |
| WO93/01160 | 1/1993 | WIPO. |
| WO93/01169 | 1/1993 | WIPO. |
| WO93/23380 | 11/1993 | WIPO. |
| WO94/10146 | 5/1994 | WIPO. |
| WO94/20500 | 9/1994 | WIPO. |
| WO 94/29309 | 12/1994 | WIPO. |
| WO95/05377 | 2/1995 | WIPO. |
| WO95/12577 | 5/1995 | WIPO. |

OTHER PUBLICATIONS

Maggi et al, *Eur. J. Pharmacol.*, 166, (1989), pp. 435–440.
Ellis et al, *J. Pharmacol. Exp. Ther.*, 267, 1 (1993), pp. 95–101.
Furchgott, *Pharm. Rev.*, 7 (1955), pp. 183–265.
Arunlakshana et al, *Brit. J. Pharmacol.*, 14, 48 (1959), pp. 48–58.
Danko et al, *Pharmacol. Comm.*, 1, 3 (1992), pp. 203–209.
Chung et al, *Molecular Pharmacol.*, 48 (1995), pp. 711–716.
Abstract of FR 2,717,802.
Fernandez, J.A. et al.: Synthesis and Central Nervous System Activity of New Piperazine Derivative & J. Med. Chem. vol. 15 (4), pp. 417–419, 1972.

Primary Examiner—Alan L. Rotman
Assistant Examiner—Charanjit S. Aulakh
Attorney, Agent, or Firm—Anita W. Magatti

[57] ABSTRACT

Compound represented by the structural formula $$Z-(C)_a-\overset{R}{\underset{Q}{C}}-\overset{A}{\underset{}{C}}-\overset{R^{6a}}{\underset{R^{7a}}{C}}_d-X-\overset{R^{9a}}{\underset{R^{8a}}{C}}_b-T \quad \text{I}$$

or a pharmaceutically acceptable salt thereof, wherein:

a is 0, 1, 2 or 3;
b, d and e are independently 0, 1 or 2;
R is H, $C_{1-6}$ alkyl, —OH or $C_2$–$C_6$ hydroxyalkyl;
A is an optionally substituted oxime, hydrazone or olefin;
X is a bond, —C(O)—, —O—, —NR$^6$—, —S(O)e—, —N(R$^6$)C(O)—, —C(O)N(R$^6$)— —OC(O)NR$^6$—, —OC(=S)NR$^6$—, —N(R$^6$)C(=S)O—, —C(=NOR$^1$)—, —S(O)$_2$N(R$^6$)—, —N(R$^6$)S(O)$_2$—, —N(R$^6$)C(O)O— or —OC(O)—;
T is H, phthalimidyl, aryl, heterocycloalkyl, heteroaryl, cycloalkyl or bridged cycloalkyl;
Q is —SR$^6$, —N(R$^6$)(R$^7$), —OR$^6$, phenyl, naphthyl or heteroaryl;
R$^{6a}$, R$^{7a}$, R$^{8a}$, R$^{9a}$, R$^6$ and R$^7$ are H, $C_{1-6}$ alkyl, $C_2$–$C_6$ hydroxyalkyl, $C_1$–$C_6$ alkoxy-$C_1$–$C_6$ alkyl, phenyl or benzyl; or R$^6$ and R$^7$, together with the nitrogen to which they are attached, form a ring;
R$^{9a}$ is R$^6$ or —OR$^6$;
Z is morpholinyl, optionally N-substituted piperazinyl, optionally substituted

[structure showing a ring with $(\cdot)_g$ and $(\cdot)_h$ substituents, N—]

or substituted

[structure showing a ring with N—]

g is 0–3 and h is 1–4, provided the sum of h and g is 1–7; wherein aryl, heterocycloalkyl, heteroaryl, cycloalkyl and bridged cycloalkyl groups are optionally substituted; methods of treating asthma, cough, bronchospasm, imflammatory diseases, and gastrointestinal disorders with said compounds, and pharmaceutical compositions comprising said compounds are disclosed.

20 Claims, No Drawings

SUBSTITUTED OXIMES, HYDRAZONES AND OLEFINS AS NEUROKININ ANTAGONISTS

CROSS REFERENCE TO RELATED APPLICATION

This is a divisional of U.S. Ser. No. 08/641,384, filed Apr. 30, 1996, now U.S. Pat. No. 5,696,267 which is a continuation-in-part of U.S. Ser. No. 08/460,819, filed Jun. 1, 1995, now abandoned which is a continuation-in-part of U.S. Ser. No. 08/432,740, filed May 2, 1995. now abandoned.

BACKGROUND OF THE INVENTION

The present invention relates to a genus of substituted oximes, hydrazones and olefins useful as antagonists of tachykinin receptors, in particular as antagonists of the neuropeptides neurokinin-1 receptor ($NK_1$) and/or neurokinin-2 receptor ($NK_2$) and/or neurokinin-3 receptor ($NK_3$).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, central nervous system conditions such as migraine and epilepsy, nociception, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Some $NK_1$ and $NK_2$ receptor antagonists have previously been disclosed: arylalkylamines were disclosed in U.S. Pat. No. 5,350,852, issued Sep. 27, 1994, and spiro-substituted azacycles were disclosed in WO 94/29309, published Dec. 22, 1994.

SUMMARY OF THE INVENTION

Compounds of the present invention are represented by the formula I

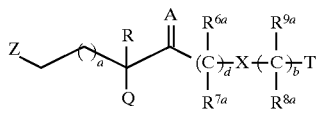

or a pharmaceutically acceptable salt thereof, wherein:

a is 0, 1, 2 or 3;

b and d are independently 0, 1 or 2;

R is H, $C_{1-6}$ alkyl, —$OR^6$ or $C_2$–$C_6$ hydroxyalkyl;

A is =N—$OR^1$, =N—N($R^2$)($R^3$), =C($R^{11}$)($R^{12}$) or =$NR^{25}$;

X is a bond, —C(O)—, —O—, —$NR^6$—, —S(O)e—, —N($R^6$)C(O)—, —C(O)N($R^6$)— —OC(O)$NR^6$—, —OC(=S)$NR^6$—, —N($R^6$)C(=S)O—, —C(=$NOR^1$)—, —S(O)$_2$N($R^6$)—, —N($R^6$)S(O)$_2$—, —N($R^6$)C(O)O— or —OC(O)—, provided that when d is 0, X is a bond, —C(O)—, —$NR^6$—, —C(O)N($R^6$)—, —N($R^6$)C(O)—, —OC(O)$NR^6$—, —C(=$NOR^1$)—, —N($R^6$)C(=S)O—, —OC(=S)$NR^6$—, —N($R^6$)S(O)$_2$— or —N($R^6$)C(O)O—; provided that when A is =C($R^{11}$)($R^{12}$) and d is 0, X is not —$NR^6$— or —N($R^6$)C(O)—; and provided that when A is =$NR^{25}$, d is 0 and X is —$NR^6$— or —N($R^6$)C(O)—;

T is H, $R^4$-aryl, $R^4$-heterocycloalkyl, $R^4$-heteroaryl, phthalimidyl, $R^4$-cycloalkyl or $R^{10}$-bridged cycloalkyl;

Q is $R^5$-phenyl, $R^5$-naphthyl, —$SR^6$, —N($R^6$)($R^7$), —$OR^6$ or $R^5$-hetero-aryl, provided that when Q is —$SR^6$, —N($R^6$)($R^7$) or —$OR^6$, R is not —$OR^6$;

$R^1$ is H, $C_{1-6}$ alkyl, —(C($R^6$)($R^7$))$_n$—G, —$G^2$, —(C($R^6$)($R^7$))$_p$—M— (C($R^{13}$)($R^{14}$))$_n$—(C($R^8$)($R^9$))$_u$—G, —C(O)N($R^6$)—(C($R^{13}$)($R^{14}$))$_n$—(C($R^8$)($R^9$))$_u$—G or —(C($R^6$)($R^7$))$_p$—M—($R^4$-heteroaryl);

$R^2$ and $R^3$ are independently selected from the group consisting of H, $C_{1-6}$ alkyl, —CN, —(C($R^6$)($R^7$))$_n$—G, —$G^2$, —C(O)—(C($R^8$)($R^9$))$_n$—G and —S(O)$_e R^{13}$; or $R^2$ and $R^3$, together with the nitrogen to which they are attached, form a ring of 5 to 6 members, wherein 0, 1 or 2 ring members are selected from the group consisting of —O—, —S— and —N($R^{19}$)—;

$R^4$ and $R^5$ are independently 1–3 substituents independently selected from the group consisting of H, halogeno, —$OR^6$, —OC(O)$R^6$, —OC(O)N($R^6$)($R^7$), —N($R^6$)($R^7$), $C_{1-6}$ alkyl, —$CF_3$, —$C_2F_5$, —$COR^6$, —$CO_2R^6$, —CON($R^6$)($R^7$), —S(O)$_e R^{13}$, —CN, —$OCF_3$, —$NR^6CO_2R^{16}$, —$NR^6COR^7$, —$NR^8CON(R^6)(R^7)$, $R^{15}$-phenyl, $R^{15}$-benzyl, $NO_2$, —N($R^6$)S(O)$_2R^{13}$ or —S(O)$_2$N($R^6$)($R^7$); or adjacent $R^4$ substituents or adjacent $R^5$ substituents can form a —O—$CH_2$—O— group; and $R^4$ can also be $R^{15}$-heteroaryl;

$R^6$, $R^7$, $R^8$, $R^{6a}$, $R^{7a}$, $R^{8a}$, $R^{13}$ and $R^{14}$ are independently selected from the group consisting of H, $C_{1-6}$ alkyl, $C_2$–$C_6$ hydroxyalkyl, $C_1$–$C_6$ alkoxy-$C_1$–$C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of —O—, —S— and —N($R^{19}$)—;

$R^9$ and $R^{9a}$ are independently selected from the group consisting of $R^6$ and —$OR^6$ $R^{10}$ and $R^{10a}$ are independently selected from the group consisting of H and $C_{1-6}$ alkyl;

$R^{11}$ and $R^{12}$ are independently selected from the group consisting of H, $C_1$–$C_6$ alkyl, —$CO_2R^6$, —$OR^6$, —C(O)N($R^6$)($R^7$), $C_1$–C6 hydroxyalkyl, -(CH$_2$)$_r$—OC(O)$R^6$, —(CH$_2$)$_r$OC(O)CH=CH$_2$, —(CH$_2$)$_r$—O(CH$_2$)$_s$—$CO_2R^6$, —(CH$_2$)$_r$—O—(CH$_2$)$_s$—C(O)N($R^6$)($R^7$) and —(CH$_2$)$_r$—N($R^6$)($R^7$);

$R^{15}$ is 1 to 3 substituents independently selected from the group consisting of H, $C_1$–$C_6$ alkyl, $C_1$–$C_6$ alkoxy, $C_1$–$C_6$ alkylthio, halogeno, —$CF_3$, —$C_2F_5$, —$COR^{10}$, —$CO_2R^{10}$, —C(O)N($R^{10}$)$_2$, —S(O)$_e R^{10a}$, —CN, —N($R^{10}$)$COR^{10}$, —N($R^{10}$)CON($R^{10}$)$_2$ and —$NO_2$;

$R^{16}$ is $C_{1-6}$ alkyl, $R^{15}$-phenyl or $R^{15}$-benzyl;

R19 is H, $C_1$–$C_6$ alkyl, —C(O)N($R^{10}$)$_2$, —$CO_2R^{10}$, —(C($R^8$)($R^9$))$_f$—$CO_2R^{10}$ or —(C($R^8$)($R^9$))$_u$—C(O)N($R^{10}$)$_2$;

f, n, p, r and s are independently 1–6;

u is 0–6;

G is selected from the group consisting of H, $R^4$-aryl, $R^4$-hetero-cycloalkyl, $R^4$-heteroaryl, $R^4$-cycloalkyl, —$OR^6$, —N($R^6$)($R^7$), —$COR^6$, —$CO_2R^6$, —CON($R^7$)($R^9$), —S(O)$_e R^{13}$, —$NR^6CO_2R^{16}$, —$NR^6COR^7$, —$NR^8CON(R^6)(R^7)$, —N($R^6$)S(O)$_2R^{13}$, —S(O)$_2$N($R^6$)($R^7$), —OC(O)$R^6$, —OC(O)N($R^6$)($R^7$), —C(=$NOR^8$)N($R^6$)($R^7$), —C(=$NR^{25}$)N($R^6$)($R^7$), —N($R^8$)C(=$NR^{25}$)N($R^6$)($R^7$), —CN, —C(O)N($R^6$)$OR^7$, and —C(O)N($R^9$)-($R^4$-heteroaryl), provided that when n is 1 and u is 0, or when $R^9$ is —$OR^6$, G is not —OH or —N($R^6$)($R^7$);

M is selected from the group consisting of a double bond, —O—, —N($R^6$)—, —C(O)—, —C($R^6$)(O$R^7$)—, —C($R^8$)(N ($R^6$)($R^7$))—, —C(=$NOR^6$) N($R^7$)—, —C(N $(R^6)(R^7))=NO\mathrm{-}$, $\mathrm{-C(=NR^{25})N(R^6)\mathrm{-}}$, $\mathrm{-C(O)N(R^9)\mathrm{-}}$, $\mathrm{-N(R^9)C(O)\mathrm{-}}$, $\mathrm{-C(=S)N(R^9)\mathrm{-}}$, $\mathrm{-N(R^9)C(=S)\mathrm{-}}$ and $\mathrm{-N(R^6)C(O)N(R^7)\mathrm{-}}$, provided that when n is 1, G is not OH or $\mathrm{-NH(R^6)}$; and when p is 2–6, M can also be $\mathrm{-N(R^6)C(=NR^{25})N(R^7)\mathrm{-}}$ or $\mathrm{-OC(O)N(R^6)\mathrm{-}}$;

$G^2$ is $R^4$-aryl, $R^4$-heterocycloalkyl, $R^4$-heteroaryl, $R^4$-cycloalkyl, $\mathrm{-COR^6}$, $\mathrm{-CO_2R^{16}}$, $\mathrm{-S(O)_2N(R^6)(R^7)}$ or $\mathrm{-CON(R^6)(R^7)}$;

e is 0, 1 or 2, provided that when e is 1 or 2, $R^{13}$ and $R^{10a}$ are not H;

$R^{25}$ is H, $C_1$–$C_6$ alkyl, $\mathrm{-CN}$, $R^{15}$-phenyl or $R^{15}$-benzyl;

Z is

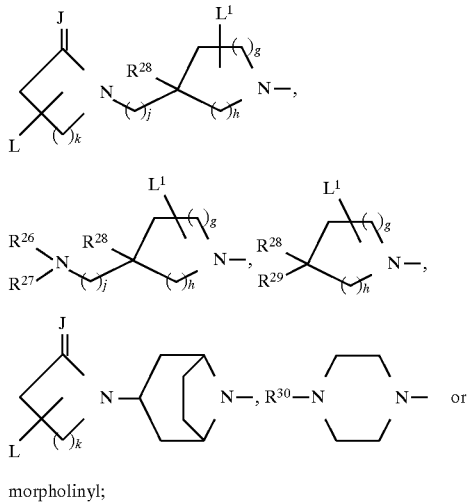

morpholinyl;

g and j are independently 0–3;

h and k are independently 1–4, provided the sum of h and g is 1–7;

J is two hydrogen atoms, $=O$, $=S$, $=NR^9$ or $=NOR^1$;

L and $L^1$ are independently selected from the group consisting of H, $C_1$–$C_6$ alkyl, $C_1$–$C_6$ alkenyl, $\mathrm{-CH_2}$-cycloalkyl, $R^{15}$-benzyl, $R^{15}$-heteroaryl, $\mathrm{-C(O)R^6}$, $\mathrm{-(CH_2)_m-OR^6}$, $\mathrm{-(CH_2)_m-N(R^6)(R^7)}$, $\mathrm{-(CH_2)_m-C(O)-OR^6}$ and $\mathrm{-(CH_2)_m-C(O)N(R^6)(R^7)}$;

m is 0 to 4, provided that when j is 0, M is 1–4;

$R^{26}$ and $R^{27}$ are independently selected from the group consisting of H, $C_1$–$C_6$ alkyl, $R^4$-aryl and $R^4$-heteroaryl; or $R^{26}$ is H, $C_1$–$C_6$ alkyl, $R^4$-aryl or $R^4$-heteroaryl, and $R^{27}$ is $\mathrm{-C(O)R^6}$, $\mathrm{-C(O)-N(R^6)(R^7)}$, $\mathrm{-C(O)(R^4\text{-aryl})}$, $\mathrm{-C(O)(R^4\text{-heteroaryl})}$, $\mathrm{-SO_2R^{13}}$ or $\mathrm{-SO_2-(R^4\text{-aryl})}$;

$R^{28}$ is H, $\mathrm{-(C(R^6)(R^{19}))_t-G}$, $\mathrm{-(C(R^6)(R^7))_v-G^2}$ or $\mathrm{-NO_2}$;

t and v are 0, 1, 2 or 3, provided that when j is 0, t is 1, 2 or 3;

$R^{29}$ is H, $C_1$–$C_6$ alkyl, $\mathrm{-C(R^{10})_2S(O)_eR^6}$, $R^4$-phenyl or $R^4$-heteroaryl;

$R^{30}$ is H, $C_1$–$C_6$ alkyl, $R^4$-cycloalkyl, $\mathrm{-(C(R^{10})_2)_w-(R^4\text{-phenyl})}$, $\mathrm{-(C(R^{10})_2)_w-(R^4\text{-heteroaryl})}$, $\mathrm{-C(O)R^6}$, $\mathrm{-C(O)OR^6}$, $\mathrm{-C(O)N(R^6)(R^7)}$,

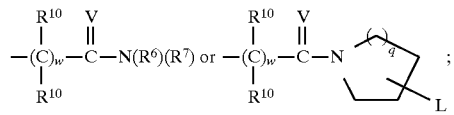

w is 0, 1, 2, or 3;

V is $=O$, $=S$ or $=NR^6$; and q is 0–4.

Preferred are compounds of formula I wherein X is $\mathrm{-O-}$, $\mathrm{-C(O)-}$, a bond, $\mathrm{-NR^6-}$, $\mathrm{-S(O)_e-}$, $\mathrm{-N(R^6)}$ $\mathrm{C(O)-}$, $\mathrm{-OC(O)NR^6}$ or $\mathrm{-C(=NOR^1)-}$. More preferred are compounds of formula I wherein X is $\mathrm{-O-}$, $\mathrm{-NR^6-}$, $\mathrm{-N(R^6)C(O)-}$ or $\mathrm{-OC(O)NR^6}$. Additional preferred definitions are: b is 1 or 2 when X is $\mathrm{-O-}$ or $\mathrm{-N(R^6)-}$; b is 0 when X is $\mathrm{-N(R^6)C(O)-}$; and d is 1 or 2. T is preferably $R^4$-aryl, $R^4$-heteroaryl, $R^4$-cycloalkyl or $R^{10}$-bridged cycloalkyl, with $R^4$-aryl, especially $R^4$-phenyl, being more preferred. Also preferred are compounds wherein $R^{6a}$, $R^{7a}$, $R^{8a}$ and $R^{9a}$ are independently hydrogen, hydroxyalkyl or alkoxyalkyl, with hydrogen being more preferred. Especially preferred are compounds wherein $R^{8a}$ and $R^{9a}$ are each hydrogen, d and b are each 1, X is $\mathrm{-O-}$, $\mathrm{-NR^6-}$, $\mathrm{-N(R^6)C(O)-}$ or $\mathrm{-OC(O)NR^6}$, T is $R^4$-aryl and $R^4$ is two substituents selected from $C_1$–$C_6$ alkyl, halogeno, $\mathrm{-CF_3}$ and $C_1$–$C_6$ alkoxy. Preferred definitions for T being $R^4$-heteroaryl include $R^4$-quinolinyl and oxadiazolyl.

Also preferred are compounds of formula I wherein R is hydrogen. Q is preferably $R^5$-phenyl, $R_5$-naphthyl or $R^5$-heteroaryl; an especially preferred definition for Q is $R^5$-phenyl, wherein $R^5$ is preferably two halogen substituents.

Preferred are compounds of formula I wherein A is $=\mathrm{N-OR^1}$ or $=\mathrm{N-N(R^2)(R^3)}$. More preferred are compounds wherein A is $=\mathrm{N-OR^1}$. $R^1$ is preferably H, alkyl, $\mathrm{-(CH_2)_n-G}$, $\mathrm{-(CH_2)_p-M-(CH_2)_n-G}$ or $\mathrm{-C(O)N}$ $(R^6)(R^7)$, wherein M is $\mathrm{-O-}$ or $\mathrm{-C(O)N(R^9)-}$ and G is $\mathrm{-CO_2R^6}$, $\mathrm{-OR^6}$, $\mathrm{-C(O)N(R^6)(R^9)}$, $\mathrm{-C(=NOR^8)N(R^6)}$ $(R^7)$, $\mathrm{-C(O)N(R^9)(R^4\text{-heteroaryl})}$ or $R^4$-heteroaryl. $R^2$ and $R^3$ are independently preferably H, $C_1$–$C_6$ alkyl, $\mathrm{-(C(R^6)(R^7))_n-G}$ or $G^2$.

Preferred definitions of Z are

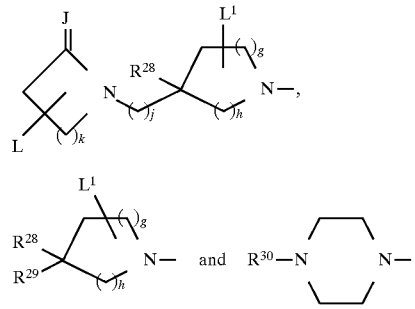

with the following groups being more preferred:

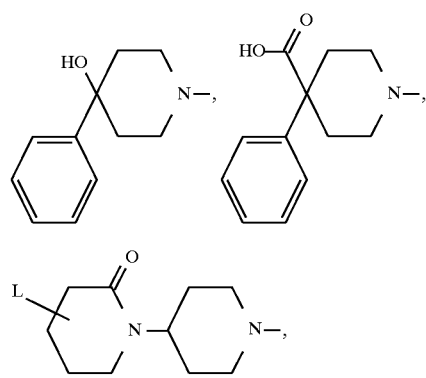

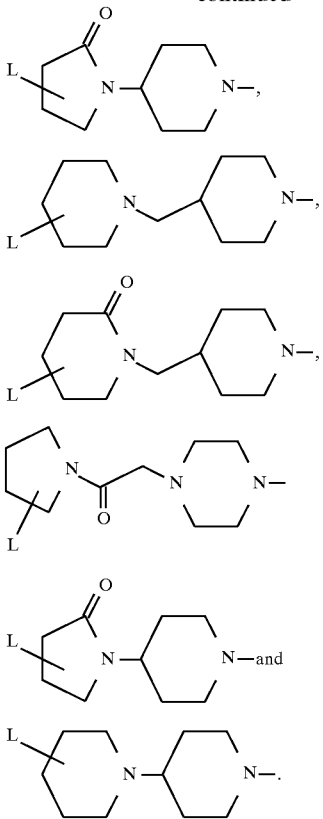

This invention also relates to the use of a compound of formula I in the treatment of asthma, cough, bronchospasm, inflammatory diseases such as arthritis, central nervous system conditions such as migraine and epilepsy, nociception, and various gastrointestinal disorders such as Crohn's disease.

In another aspect, the invention relates to a pharmaceutical composition comprising a compound of formula I in a pharmaceutically acceptable carrier. The invention also relates to the use of said pharmaceutical composition in the treatment of asthma, cough, bronchospasm, inflammatory diseases such as arthritis, migraine, nociception, and various gastrointestinal disorders such as Crohn's disease.

DETAILED DESCRIPTION

As used herein, the term "alkyl" means straight or branched alkyl chains. "Lower alkyl" refers to alkyl chains of 1–6 carbon atoms and, similarly, lower alkoxy refers to alkoxy chains of 1–6 carbon atoms.

"Cycloalkyl" means cyclic alkyl groups having 3 to 6 carbon atoms. "Bridged cycloalkyl" refers to $C_7$–$C_{10}$ saturated rings comprised of a cycloalkyl ring or a fused bicycloalkyl ring and an alkylene chain joined at each end to non-adjacent carbon atoms of the ring or rings. Examples of such bridged bicycloalkyl rings are adamantyl, myrtanyl, noradamantyl, norbornyl, bicyclo[2.2.1]heptyl, 6,6-dimethylbicyclo[3.1.1]heptyl, bicyclo[3.2.1]octyl, and bicyclo[2.2.2]octyl.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered saturated rings comprising 1 to 3 heteroatoms independently selected from the group consisting of —O—, —S— and —N($R^{19}$)—, with the remaining ring members being carbon. Examples of heterocycloalkyl rings are tetrahydrofuranyl, pyrrolidinyl, piperidinyl, morpholinyl, thiomorpholinyl and piperazinyl. $R^4$-heterocycloalkyl refers to such groups wherein substitutable ring carbon atoms have an $R^4$ substituent.

"Heteroaryl" refers to 5- to 10-membered single or benzofused aromatic rings comprising 1 to 4 heteroatoms independently selected from the group consisting of —O—, —S— and —N=, provided that the rings do not include adjacent oxygen and/or sulfur atoms. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are indolyl, quinolinyl, thianaphthenyl and benzofurazanyl. N-oxides of nitrogen-containing heteroaryl groups are also included. All positional isomers are contemplated, e.g., 1-pyridyl, 2-pyridyl, 3-pyridyl and 4-pyridyl. $R^4$-heteroaryl refers to such groups wherein substitutable ring carbon atoms have an $R^4$ substituent.

Where $R^2$ and $R^3$ or $R^6$ and $R^7$ substituents on a nitrogen atom form a ring and additional heteroatoms are present, the rings do not include adjacent oxygen and/or sulfur atoms or three adjacent hetero-atoms. Typical rings so formed are morpholinyl, piperazinyl and piperidinyl.

In the structures in the definition of Z, the substituents L and $L^1$ may be present on any substitutable carbon atom, including in the second structure the carbon to which the —N($R^{26}$)($R^{27}$) group is attached.

In the above definitions, wherein variables $R^6$, $R^7$, $R^8$, $R^9$, $R^{10}$, $R^{13}$, $R^{14}$, $R^{15}$, $R^{30}$ and $R^{31}$, for example, are said to be independently selected from a group of substituents, we mean that $R^6$, $R^7$, $R^8$, $R^9$, $R^{10}$, $R^{13}$, $R^{14}$, $R^{15}$, $R^{30}$ and $R^{31}$ are independently selected, but also that where an $R^6$, $R^7$, $R^8$, $R^9$, $R^{10}$, $R^{13}$, $R^{14}$, $R^{15}$, $R^{30}$ or $R^{31}$ variable occurs more than once in a molecule, those occurrences are independently selected (e.g., if B is =$NR^6$— wherein $R^6$ is hydrogen, X can be —N($R^6$)— wherein $R^6$ is ethyl). Similarly, $R^4$ and $R^5$ can be independently selected from a group of substituents, and where more than one $R^4$ and $R^5$ are present, the substitutents are independently selected; those skilled in the art will recognize that the size and nature of the substituent (s) will affect the number of substituents which can be present.

Compounds of formula I can have at least one asymmetrical carbon atom and all isomers, including diastereomers, enantiomers and rotational isomers, as well as E and Z isomers of the oxime, hydrazone and olefin groups, are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention have at least one amino group which can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared using methods well known to those skilled in the art. Following are typical procedures for preparing various compounds; the skilled artisan will recognize that other procedures may be applicable, and that the procedures may be suitably modified to prepare other compounds within the scope of formula I.

Procedure A:

Compounds of formula I wherein R is H, a and d are each 1, X is —O—, Q is $R^5$-phenyl, T is $R^4$-phenyl, A is =$NOR^1$ and the remaining variables are as defined above (see formula, below), can be prepared as shown in the following reaction scheme:

Step 1:

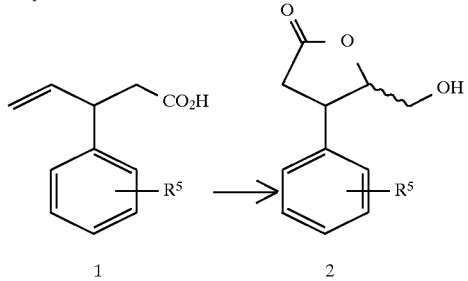

In step 1, the 3-(substituted phenyl)-2-propenoic acid of formula I, wherein $R^5$ is as defined above, is reacted with an oxidizing agent such as dimethyl dioxirane or m-chloroperoxybenzoic acid (m-CPBA) in an inert organic solvent such as $CH_2Cl_2$ or toluene. An acidic catalyst such as Amberlyst 15 or formic acid is added to give the desired lactone 2. Preferable reaction temperatures range from 0° to 60° C.

Step 2:

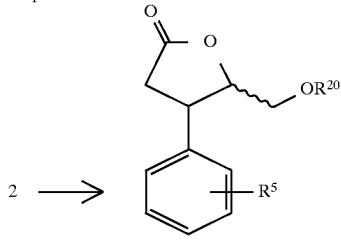

In step 2, lactone 2 is reacted with a suitable hydroxy-protecting group, for example an electrophile such as a compound of formula $R^{20}$—$R^{17}$ wherein $R^{17}$ is a leaving group such as Cl or Br and $R^{20}$ is of the formula

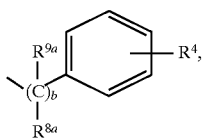

wherein $R^4$, $R^{8a}$, $R^{9a}$ and b are as defined above, or wherein $R^{20}$ is trialkylsilyl. The reaction is carried out in the presence of a silver salt such as $Ag_2O$ in an organic solvent such as dimethylformamide (DMF) or tetrahydrofuran (THF), most preferably DMF, at a temperature of 0° to about 500° C.

Step 3:

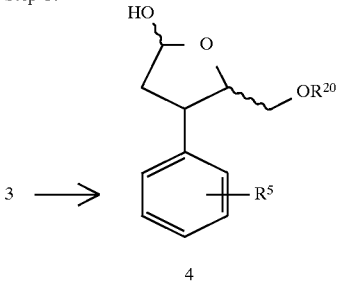

In step 3, compound 3 is dissolved in an inert organic solvent such as $CH_2Cl_2$, THF or toluene, preferably $CH_2Cl_2$, and reduced with a reagent such as DiBAL-H at temperatures from about −78° C. to room temperature.

Step 4:

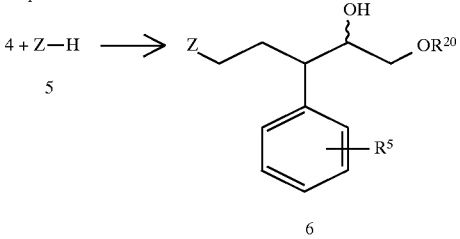

In step 4, compound 4 is reacted with an amine of formula 5, wherein Z is as defined above, in an alcohol such as $CH_3OH$, $CH_3CH_2OH$ or more preferably $CF_3CH_2OH$, in the presence of a dehydrating agent such as molecular sieves and a reducing agent such as $NaCNBH_3$ or under hydrogenating conditions ($H_2$/Pd/C), at a temperature range of 0 to 60° C.

Step 5:

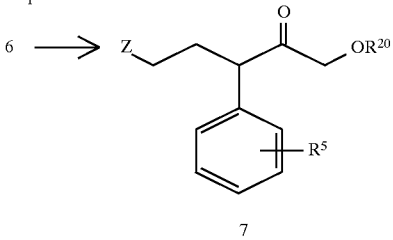

In Step 5, a compound of formula 6 is oxidized to the corresponding ketone of formula 7 using an oxidizing agent such as pyridinium chlorochromate (PCC) or Jones reagent, preferably Jones reagent, in a suitable organic solvent such as $CH_2Cl_2$ or toluene (for PCC) or acetone (for Jones reagent) at a temperature from about 0° to 50° C. Other suitable oxidizing agents include pyridinium dichromate (PDC), tetrapropylammonium perruthenate(VII)/4-methylmorpholine N-oxide (TPAP/NMO), and (COCl)$_2$/DMSO.

Step 6:

7 →  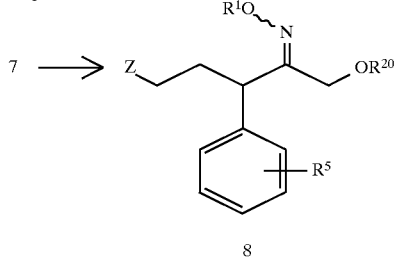

8

In Step 6, the ketone of formula 7 is converted to the corresponding oxime of formula 8 by treatment with a hydroxylamine derivative of the formula H$_2$NOR$^1$ or a salt thereof, e.g., the HCl salt, wherein R$^1$ is as defined above, in a suitable organic solvent such as pyridine at a temperature of from about 25° to 100° C. Alternatively, a low molecular weight alcohol (e.g., CH$_3$OH or CH$_3$CH$_2$OH) can be used as the solvent, in which case a base such as sodium acetate must be added. Alternatively, compounds of formula 8 wherein R$^1$ is not H can be prepared from compounds of formula 8 wherein R$^1$ is H by deprotonation with a suitable base, preferably NaH or Cs$_2$CO$_3$, and subsequent treatment with a suitable electrophile such as an alkyl halide, acid chloride or isocyanate.

When R$^{20}$ in oxime 8 is a trialkyl silyl hydroxy-protecting group such as (CH$_3$)$_3$Si—, (t—Bu)Si(CH$_3$)$_2$—, (Et)Si(i-Pr)$_2$— or (i—Pr)$_3$Si— (wherein Et is ethyl, i—Pr is isopropyl and t—Bu is tertiary butyl)), preferably (t—Bu)Si(CH$_3$)$_2$—, the oxime can be converted to the corresponding hydroxymethyl oxime of formula 8A, for example by treatment with fluoride ion, preferably TBAF:

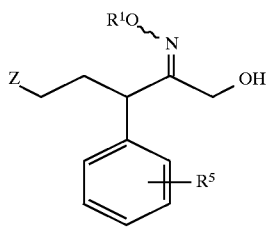

8A

Oxime 8A can be alkylated, acylated or the hydroxyl group can be activated displaced by sulfur or nitrogen nucleophiles. Alkylations are effected using a base, such as NaH, K$_2$CO$_3$ or Cs$_2$CO$_3$, in a solvent such as DMF, THF or CH$_2$Cl$_2$, with an alkylating agent such as an alkyl or benzyl halide or sulfonate. Acylations are effected using an appropriate carboxylic acid in the presence of a dehydrating agent, for example DEC in the presence of HOBT. Nitrogen and sulfur-containing groups can be introduced using Mitsunobu reaction conditions, for example DEAD and PPh$_3$ in a solvent such as THF with a thiol or amide nucleophile.

Corresponding compounds of formula I wherein A is a =C(R$^{11}$)(R$^{12}$) group are prepared by converting a compound of formula 7 to the corresponding alkene of formula 25

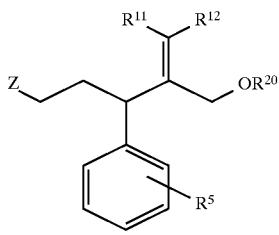

25 by treating the ketone of formula 7 with the Wittig reagent formed from Ph$_3$PCHR$^{11}$R$^{12}$R$^{17'}$ (R$^{17'}$=Cl, Br, I) and a suitable base such as NaH, LDA, or R$^{18}$N(TMS)$_2$ (R$^{18}$=Li, Na, or K) preferably NaN(TMS)$_2$, in a suitable organic solvent such as THF or ether, preferably THF, at a temperature from −15° to 65° C. Other suitable reagents for this transformation include the phosphonates (EtO)$_2$P(O)CHR$^{11}$R$^{12}$.

Corresponding compounds of formula I wherein A is a =N—N(R$^2$)(R$^3$) group are prepared by converting a compound of formula 7 to the corresponding hydrazone of formula 26

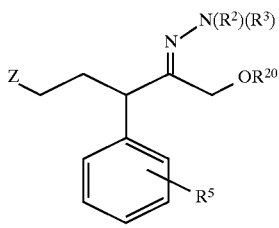

26 by treating the ketone of formula 7 with a substituted hydrazine of formula H$_2$NNR$^2$R$^3$ in a suitable organic solvent such as CH$_3$OH or CH$_3$CH$_2$OH, preferably CH$_3$CH$_2$OH, in the presence of an acidic catalyst such as acetic acid at a temperature in the range of 0° to 80° C.

Procedure B:

Compounds of formula I wherein R is H, a and d are each 1, X is —O— or —S—, Q is R$^5$-phenyl, T is H, R$^4$-aryl, R$^4$-cycloalkyl, R$^4$-alkyl, R$^4$-bicyclo or tricycloalkyl, and the remaining variables are as defined above (see compound 35, below), can be prepared according to the following reaction scheme:

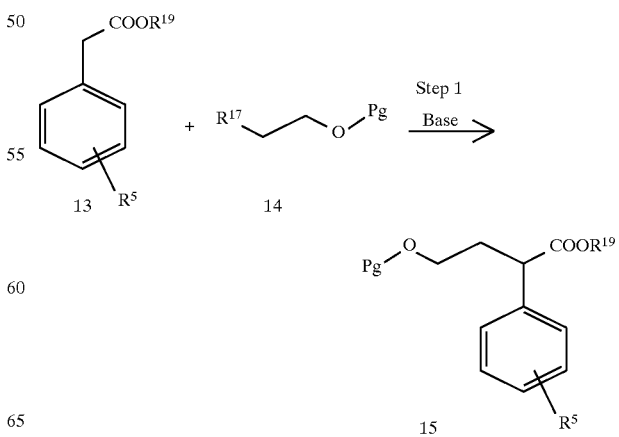

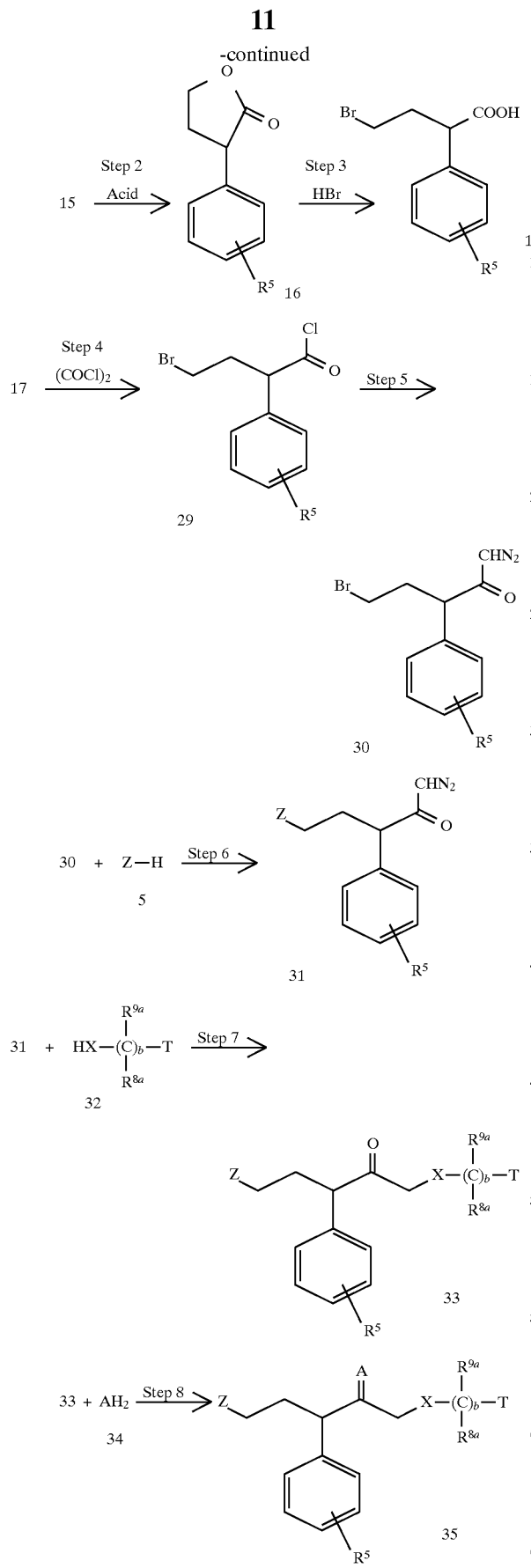

In step 1, the ester (preferably methyl) of the substituted aryl acetic acid of formula 13, wherein $R^{19}$ is a lower alkyl group, preferably methyl, is reacted with a compound of formula 14, wherein $R^{17'}$ is as defined above and Pg is a suitable protecting group such as tetrahydropyranyl, and a base to prepare a compound of formula 15. The base can be chosen from any strong base including LDA or lithium bis(trimethylsilyl)amide. The reaction is carried out in an inert organic solvent such as THF at temperatures of −15° to about 65° C.

In step 2, a compound of formula 15 is reacted with an acid in a solvent such as $CH_3OH$, at temperatures ranging from −10° to 65° C. The acid need not to be used in stochiometric amount. Alternatively, a compound of formula 16 can be prepared directly from step 1 without isolating the compound of formula 15: the reaction mixture obtained after the work up of the reaction described in step 1 can be dissolved in the solvent and reacted with the acid.

In step 3, a compound of formula 16 is reacted with an acid such hydrobromic acid (HBr) dissolved in a suitable solvent such as acetic acid. The reaction is performed at temperatures ranging from 5° to 45° C.

In step 4, the carboxylic acid of formula 17 is reacted with a halogenating agent such as $SOCl_2$ or $(COCl)_2$ in an appropriate solvent such $CH_2Cl_2$ to form the acid halide of formula 29.

In step 5, the compound of formula 29 is reacted with an alkylating agent such as diazomethane to obtain the compound of formula 30. This reaction may be performed at temperatures lower than ambient using an appropriate solvent such as $Et_2O$.

In step 6, a compound of formula 30 is reacted with a compound of formula 5 (defined above) to obtain a compound of formula 31. The reaction is carried out in a suitable solvent, e.g. EtOAc, at temperatures below 85° C. Bases such as $Et_3N$ may be beneficial to the reaction.

In step 7, a compound of formula 31 is reacted with a compound of formula 32, wherein X is —O— or —S—, T is H, $R^4$-aryl, $R^4$-cycloalkyl, $R^4$-alkyl, $R^4$-bicyclo or tricycloalkyl, and $R^{8a}$, $R^{9a}$, b and $R^4$ is as defined above in an appropriate solvent, e.g. $CH_2Cl_2$, with a Lewis acid, e.g. $BF_3$, at temperatures lower than 50° C.

In step 8 a compound of formula 33 is reacted with a compound of formula 34, wherein A is as defined above, in a solvent such as pyridine, to obtain the desired product of formula 35.

Procedure C:

Compounds of formula I wherein R is H, a and d are each 1, A is =$NOR^1$, X is —O—, Q is $R^5$-phenyl, T is $R^{15}$-phenyl ($R^{15}$ is a subset of $R^4$), and the remaining variables are as defined above (see compound 46, below), can be prepared according to the following reaction scheme:

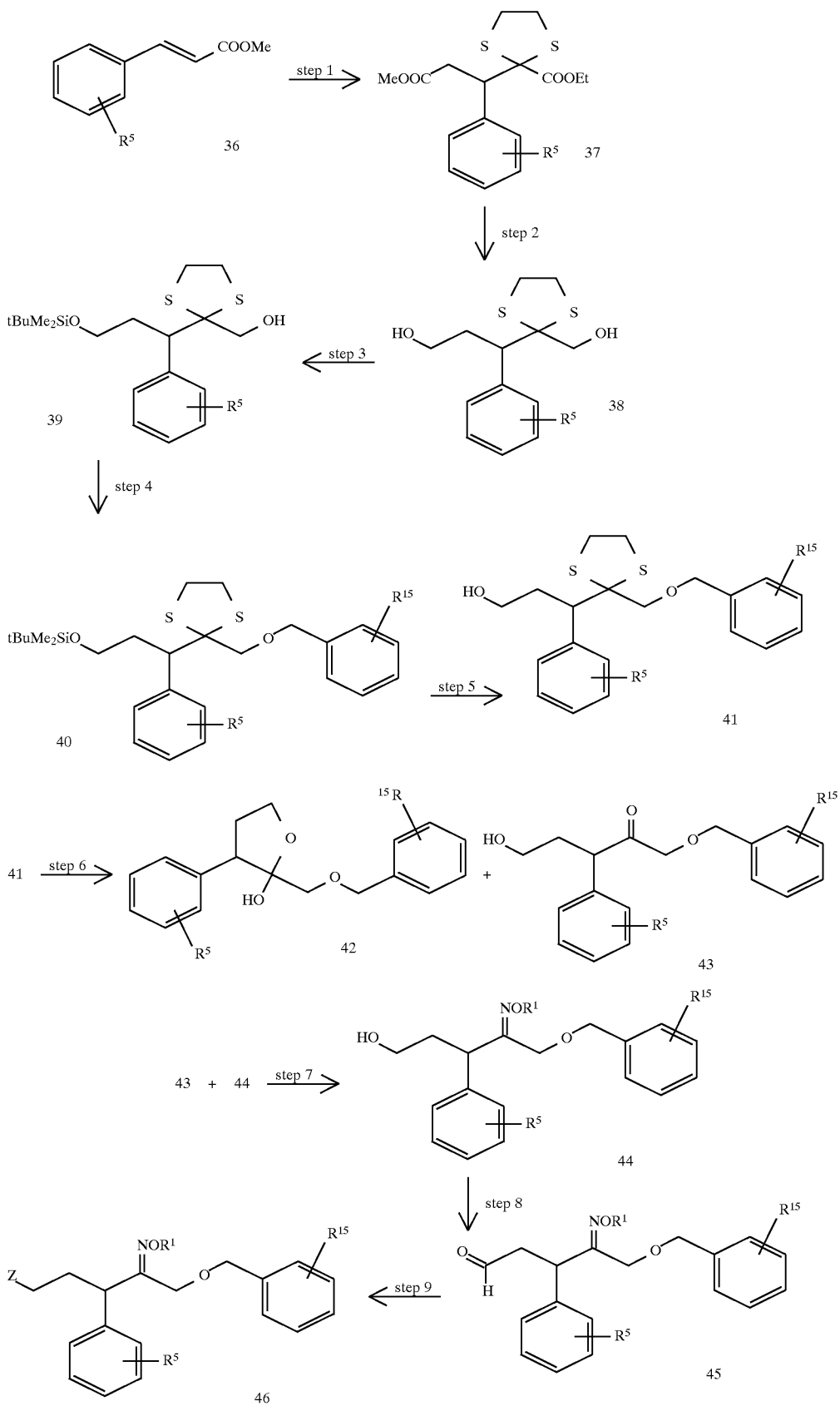

Steps 1 to 4 are preferably carried out in an inert solvent such as an ether (e.g. Et$_2$O, THF, or dioxane) under an inert atmosphere (N$_2$ or Ar).

In step 1, the anion (Li, Na or K) of ethyl 1,3-dithiolane-2-carboxylate is added to the cinnamate 36 at any suitable temperature, preferably −78° C. to −55° C.

Step 2, deprotection of the carboxy group in 37 is carried out with any suitable reducing agent (e.g. LiAlH$_4$ or diisobutylaluminum hydride) at any suitable temperature, preferably between 0° C. and 25° C.

In step 3, the hydroxy group of 38 is reacted with t-butyldimethylsilyl chloride and a suitable base (e.g. pyridine, Et$_3$N, dimethylaminopyridine, or diisopropylethylamine) at any suitable temperature, preferably between 0° C. and 25° C.

Step 4 is preferably carried out by first adding a suitable base (e.g. KH or [(CH$_3$)$_3$Si]$_2$NK) to the solvent containing 39 and subsequently adding the alkylating agent (e.g. a benzyl chloride or bromide) to obtain 40. Any suitable temperature can be used, preferably between −78° C. and 0° C. for the deprotonation and between 25° C. and 80° C. for the alkylation.

In step 5, removal of the silyl protecting group on 40 is preferably carried out with a fluoride source such as HF in CH$_3$CN or tetrabutyl-ammonium fluoride in an inert solvent such as an ether as described above. This step can also be carried out with acid (e.g. HOAc, CF$_3$CO$_2$H, tosic acid, H$_2$SO$_4$, or HCl) and water in an inert solvent such as an ether as described above, or in a chlorinated hydrocarbon (e.g. CH$_2$Cl$_2$, 1,2-dichloroethane, or CHCl$_3$). Any suitable temperature can be used, preferably temperatures between 0° C. and 80° C.

In step 6, oxidation of the dithiolanyl ring of 41 is preferably carried out with an oxidizing agent such as HgClO$_4$, AgNO$_3$, Ag$_2$o, copper chloride with copper oxide, thallium nitrate, N-chlorosuccinimide, or N-bromosuccinimide in an inert solvent such as an ether (e.g. Et$_2$O, THF, or dioxane), CH$_3$COCH$_3$, or CH$_3$CN. Any suitable temperature can be used with preferable temperatures between 0° C. and 80° C. Compounds 42 and 43 are present in equilibrium.

Preparation of the oxime of formula 44 in step 7 is preferably carried out on the mixture of 42 and 43 with a suitably substituted hydroxylamine (as its acid salt e.g. HCl or maleate, or as its free base) and a suitable base such as sodium acetate or pyridine in a protic solvent (e.g. water, CH$_3$OH, CH$_3$CH$_2$OH, or isopropanol). Any suitable temperature can be used, with preferable temperatures between 25° C. and 100° C.

In step 8, preferably 44 is treated with a suitable oxidizing agent (e.g. pyridinium chlorochromate, chromium trioxide-pyridine, pyridinium dichromate, oxalyl chloride-dimethylsulfoxide, acetic anhydride-dimethylsulfoxide, or periodinane) in an inert solvent such as chlorinated hydrocarbons (e.g. CH$_2$Cl$_2$, 1,2-dichloroethane, or CHCl$_3$) to obtain the ketone 45. Any suitable temperature can be used with preferable temperatures between −78° C. and 25° C.

Step 9 is preferably carried out with a suitably substituted amine (as its acid salt e.g. HCl or maleate or as its free base) and a hydride source such as NaBH$_3$CN or sodium triacetoxyborohydride in a protic solvent (e.g. CH$_3$OH, CH$_3$CH$_2$OH, or CF$_3$CH$_2$OH) with 3A sieves to obtain 46. Any suitable temperature can be used with preferable temperatures between 0° C. and 25° C.

Procedure D:

Compounds of formula I as defined above can be prepared as shown in the following reaction scheme:

Step 1:

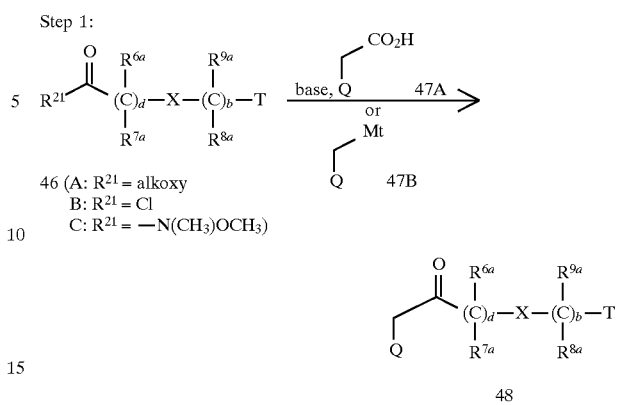

46 (A: R$^{21}$ = alkoxy
B: R$^{21}$ = Cl
C: R$^{21}$ = —N(CH$_3$)OCH$_3$)

In step 1, a compound of formula 47A. wherein Q is as defined above, is reacted with a base such as lithium diisopropylamide (LDA) or KH in an inert organic solvent such at THF or DME to generate a dianion. An acid chloride, ester or amide of formula 46A, 46B, or 46C is added to give a ketone of formula 48. Preferable reaction temperatures ranges from −78° C. to 30° C.

Alternatively, compounds of formula 48 can be generated by the reaction of a compound of formula 46, preferably 46C, with a metallated species of formula QCH$_2$Mt where Mt is a metal, such as MgHal, wherein "Hal" is halogen, or lithium. The metallated species QCH$_2$Mt can be generated by conventional procedures, such as treatment compounds of formula QCH$_2$Hal with Mg or by treating QCH$_3$ with an organolithium base.

Step 2:

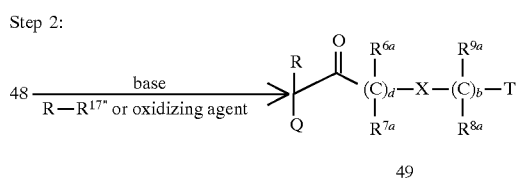

In step 2, for compounds of formula I wherein R is not hydrogen, the ketone 48 is reacted with a suitable base, such as LDA or KH in an inert organic solvent such as THF. For compounds wherein R is alkyl or hydroxyalkyl, a compound R—R$^{17"}$, wherein R$^{17"}$ is leaving group such as Br, I or triflate is added. For compounds wherein R is OH, an appropriate oxidizing agent such as dimethyldioxirane or Davis reagent is added. Preferable reaction temperatures range from −78° to 50° C.

Step 3:

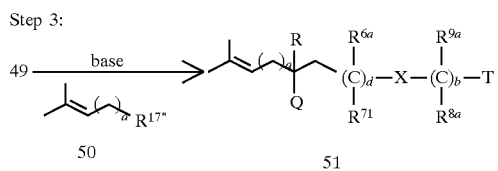

In step 3, ketone 49 is reacted with a base such as LDA in a solvent such as THF, then an olefin of formula 50 is added, wherein R$^{17"}$ is as defined above, to give the adduct 51. Preferable reaction temperatures range from −78° C. to 60° C.

Step 4:

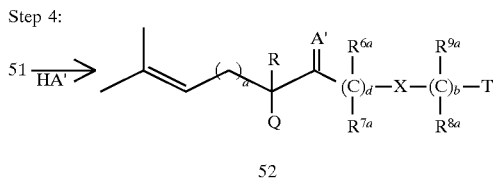

52

In step 4, ketone 51 is reacted with HA', wherein A' is NH—OR$^1$, NH-N(R$^2$)(R$^3$) or NHR26, in an organic solvent such as pyridine at a temperature from 25° C. to 150° C. to give a compound of formula 52.

Step 5:

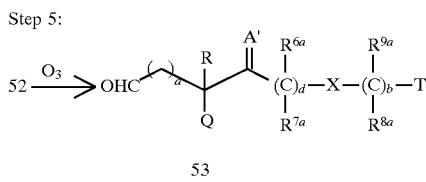

53

In step 5, a compound of formula 52 is oxidized by ozonolysis to give an aldehyde of formula 53. Suitable organic solvents include EtOAc, ethanol or the like. Preferable reaction temperatures are from −78° to 0°

Step 6:

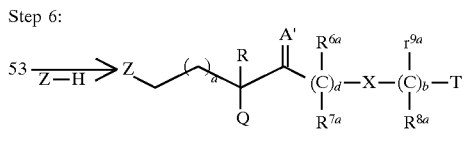

In step 6, an aidehyde of formula 53 is reacted with a compound of formula Z-H, wherein Z is as defined above, as described in Step 9 of Procedure C.

Alternatively, a compound of formula I can be prepared from 51 by the following reaction scheme:

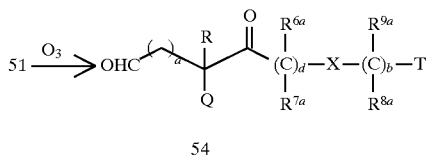

54

Compound 51 is oxized to a compound of formula 54 under conditions similar to those described for step 5 above. The aldehyde of formula 54 is reacted with a compound of formula Z—H in a manner similar to that described in Step 6, and the resultant ketone is then reacted with a compound of the formula HA' as described above in Step 4 to obtain the compound of formula I.

Procedure E:

Compounds of formula I wherein X is —O— or a bond and d is 1 or 2 can be prepared by the following reaction scheme, starting with ketone 49 from Procedure D. Alternatively, compounds of formula 49 can be prepared from compounds of formula 46D, wherein X is —O—, R$^{6a}$ and R$^{7a}$ are each H, and d is 1, which, in turn, are prepared according to the following reaction scheme:

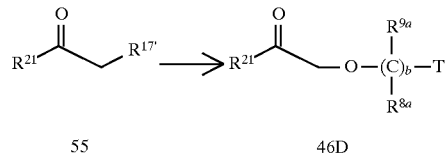

55                                     46D wherein compounds of formula 55, wherein R$^{21}$ is alkoxy or —N(CH$_3$)OCH$_3$ and R$^{17'}$ is as defined above are reacted with alcohols of the formula HO—(C(R$^{8a}$)(R$^{9a}$))$_b$—T in the presence of a suitable base such as Cs$_2$CO$_3$ or KHMDS to give the desired ether 46D.

Step 1:

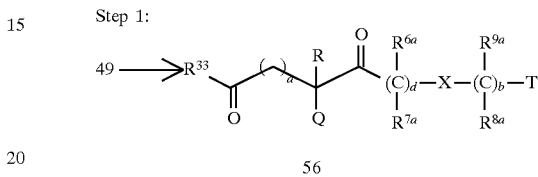

56

In step 1, compounds of formula 49 treated with an appropriate base, such as NaH, are reacted with alkylating agents of the formula R$^{33}$C(O)CH$_2$R$^{17}$ or R$^{33}$C(O)CH=CH$_2$ wherein R$^{33}$ is alkoxy or —N(CH$_3$)OCH$_3$ and R$^{17}$ is as defined above.

Step 2:

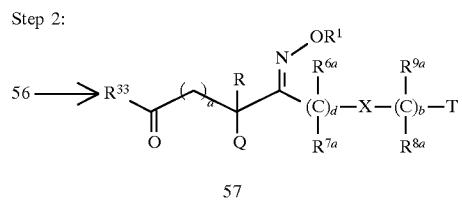

57

In step 2, compounds of formula 56 can be converted to the corresponding oxime of formula 57 in a manner similar to that described in Procedure D, Step 4.

Step 3:

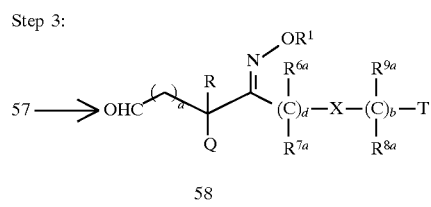

58

In step 3, compounds of formula 57 (or 56, i.e., wherein A' is O) are converted to the corresponding aldehyde 58 (or lactol from the keto-ester 56) by treatment with a suitable reducing agent such a DIBAL, in an suitable inert organic solvent such as THF, at a temperature from about −100° to −20° C.

Step 4:

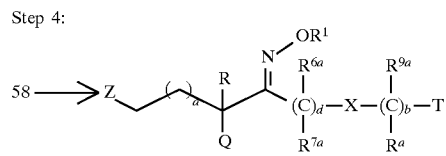

In step 4, compound 58 is reacted with an amine ZH in a manner similar to that described in Procedure B, Step 9, to obtain the compound of formula I.

Alternatively, as shown in the following reaction scheme, compounds of the formula 59, wherein R is H, A' is =O, X is —O— and $R^{33}$ is alkoxy can be converted to the corresponding lactol of formula 60 by treatment with a suitable reducing agent such a DIBAL, in an suitable inert organic solvent such as THF, at a temperature from about —100°0 to —20° C.:

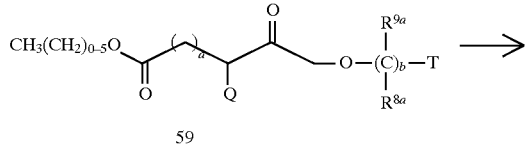

The lactol is then reacted with an amine ZH as described in Procedure A, Step 4, to give the amino alcohol 6.

Procedure F:

Compounds of formula I wherein R is H, d is 1, $R^{6a}$ and $R^{7a}$ are each H, X is a bond, —$(C(R^{9a})(R^{8a}))_b$— is —CH(OH)$(C(R^{8a})(R^{9a}))_{b1}$—, wherein b1 is 0 or 1 and $R^{8a}$ and $R^{9a}$ are generally as defined above, but are preferably not $R^{15}$-phenyl or $R^{15}$-benzyl, and the remaining variables are as defined above, are prepared by the following procedure (In the scheme below, Z is exemplified by 4-hydroxy-4-phenylpiperidine, but other Z—H amines can also be used.):

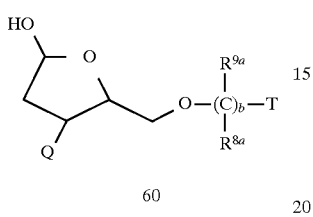

In Step 1, the amine of formula 63 is condensed with the acid of formula 64 using standard methods, for example a coupling agent such as DCC or EDCI in the presence of a base such as pyridine or $Et_3N$ (when necessary) is used in a solvent such as THF at temperatures from 0 to 50° C. preferably room temperature.

In Step 2, the alkene of formula 65 is converted to the nitro-substituted compound of formula 66 by refluxing the alkene in nitromethane in the presence of a base such as an alkoxide, a tert.-ammonium hydroxide or alkoxide, a trialkyl amine or a metal fluoride salt. The nitromethane can act as the solvent, or another solvent such as an alcohol, an ether, DMSO or DMF also can be used.

In Step 3, the nitro-oxobutyl compound of formula 66 is reacted with the olefin of formula 67 and $C_6H_5NCO$ in the presence of a trace amount of a base such as $Et_3N$, in an inert, non-hydroxylic solvent such as THF or $CH_2Cl_2$ to obtain the isoxazolinyl compound of formula 68. Reaction temperatures range from 0 to 40° C., with room temperature preferred.

In Step 4, the keto group is reduced, for example by refluxing with a reagent such as borane-dimethylsulfide complex. In Step 5, the isoxazolinyl ring is opened by treatment with Raney Nickel under conditions well known in the art. In Step 6, the ketone is converted to the oxime as described in Procedure A, Step 6.

The hydroxy-substituted compounds prepared above can be oxidized to the corresponding ketones, for example by treatment with Jones reagent. The resultant ketones can be converted to the corresponding bis-oximes using the methods described in Procedure A, Step 6.

Procedure G:

Compounds of formula I wherein R is H, d is 0, X is —C(O)— and the remaining variables are as defined above, are prepared by the following procedure (As above, other Z—H amines can also be used.):

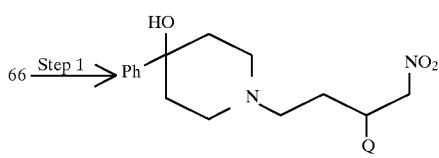

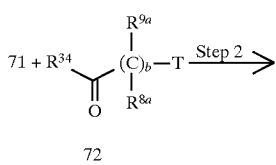

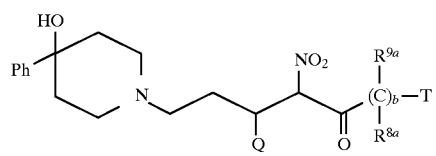

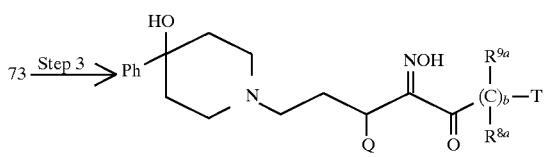

In Step 1, a compound of formula 66 is reduced in a manner similar to Procedure F, Step 4. In Step 2, the resultant nitrobutyl compound of formula 71 is reacted with a carboxyl derivative of formula 72, wherein $R^{34}$ is a leaving group such as a phenoxy, or an activating group such as p-nitro-phenyl, imidazolyl or halogeno, in the presence of a base such as potassium tert.-butoxide, in a solvent such as DMSO. Reaction temperatures range from 0° to 30° C.

In Step 3, the nitro group is converted to the oxime by treatment with $CS_2$ in the presence of a base such as $Et_3N$ in a solvent such as $CH_3CN$. The oxime can be converted into other oximes of formula I, i.e., wherein A is =N—$OR^1$ and $R^1$ is other than H, by the methods described in Procedure A, Step 6.

Similarly, compounds of formula I wherein d is 0, X is a bond, —$(C(R^{9a})(R^{8a}))_b$— is —$CH(OH)CH_2$— and the remaining variables are as defined above, are prepared by reducing the keto group of compound 73 using well known techniques, for example by treatment with $NaBH_4$, followed by converting the nitro group to the oxime as described above.

Procedure H:

Compounds of formula I wherein R is H, d is 0, X is —NH—, A is =NH, —$(C(R^{9a})(R^{8a}))_b$—T is —$(CH_2)_{b2}$—T—, wherein b2 is 1 or 2 and the remaining variables are as defined above, are prepared by the following procedure (As above, other Z—H amines can also be used.):

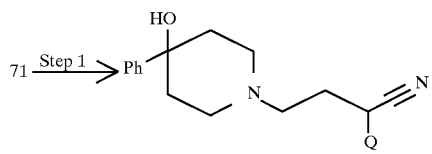

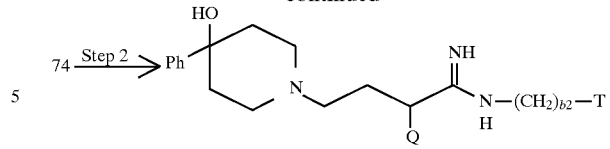

In Step 1, the nitrobutyl compound of formula 71 is reduced to the corresponding nitrile by treatment with $CS_2$ in the presence of a base such as $Et_3N$ in a solvent such as $CH_3CN$ at temperatures of 20° to 70° C.

In Step 2, the nitrile of formula 74 is reacted at elevated temperatures with an amine of formula $NH_2$—$(CH_2)_{b2}$—T in the presence of a catalyst such as a trialkylaluminum, in a solvent such as $CH_2Cl_2$ or toluene.

The following procedure can be used to prepare similar compounds wherein —$(C(R^{9a})(R^{8a}))_b$— is —$CH_2(C(R^{9a})(R^{8a}))$— and A is =$NOR^1$:

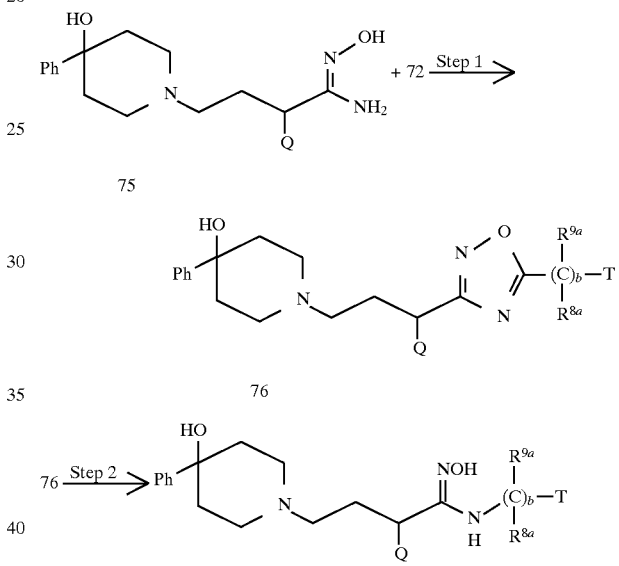

In Step 1, a oximeamide of formula 75, prepared by treating a compound of formula 74 with hydroxylamine, is reacted with a carbonyl derivative of formula 72 in a solvent such as pyridine at a temperature of about 70° C. to obtain an oxadiazolyl compound of formula 76.

In Step 2, the oxadiazolyl ring is opened by treatment with a reducing agent such as LAH, in a solvent such as ether, at temperatures of 20° to 60° C. to obtain the desired compounds of formula I.

Preparation of Starting Materials:

Starting materials of formula 27

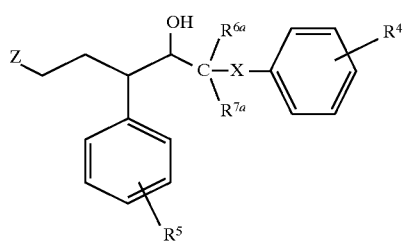

wherein X is —$NR^6$— or —S— and Z, $R^4$, $R^5$, $R^{6a}$ and $R^{7a}$ are as defined above can be prepared as shown in the following reaction scheme:

Step 1:

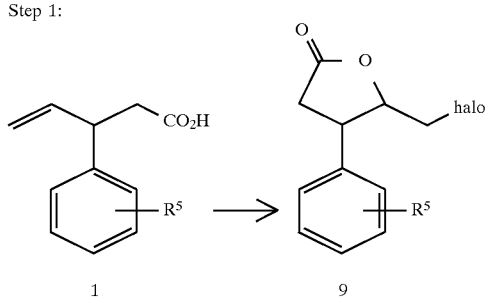

In step 1, compound 1, wherein $R^5$ is as defined above, is treated with a halogenating agent such as $I_2$ or N-bromosuccinimide in an organic solvent such as $CH_3CN$, THF or DMF at a temperature in the range of 0 to 250° C. to give the halolactone 9.

Step 2:

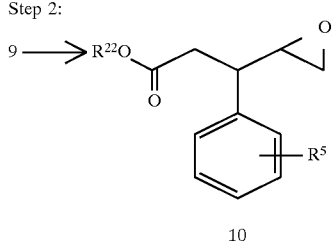

In step 2, compound 9 is dissolved in an alcohol $R^{22}OH$ wherein $R^{22}$ is a lower alkyl group such as methyl or ethyl, preferably methyl. A base such as $Cs_2CO_3$ or $Na_2CO_3$ is added and the mixture stirred at a temperature range of 0° to 50° C. to give the epoxide 10.

Alternatively, a lower alkyl ester of 1 can be epoxidized by a suitable epoxidizing agent such as dimethyl dioxirane or m-CPBA to obtain a compound of formula 10.

Step 3:

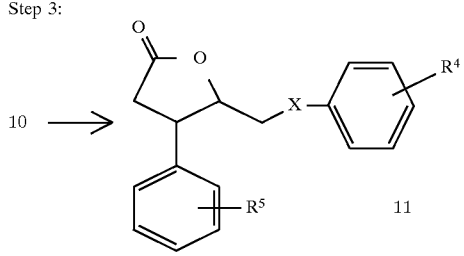

In step 3, a solution of epoxide 10 in an alcohol such as $CH_3OH$, $CH_3CH_2OH$, or more preferably $CF_3CH_2OH$, is treated with a nucleophile of the formula

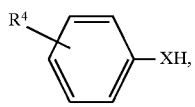

wherein X is $-NR^6-$ or $-S-$, and $R^4$ is as defined above, at 0° to 90° C. to give the lactone 11. Step 4: Using the reactions of Procedure A, steps 3 and 4, convert the lactone of formula 11 to the desired product of formula 27.

In a similar manner, starting materials of formula 28

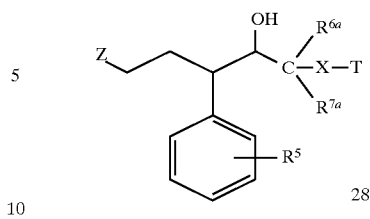

wherein X is $-NR^6-$ and T, Z, $R^5$, $R^{6a}$ and $R^{7a}$ are as defined above can be prepared as described above by treating an epoxide of formula 10 with an amine of formula $HN(R^6)-T$ and converting the resultant lactone to the compound of formula 28.

Also in a similar manner, an epoxide of formula 10 can be treated with a thiol of formula $HS(C(R^{8a})(R^{9a}))_b-T$ to obtain the corresponding lactone, which can be converted to the desired compound using Procedure A, steps 3 and 4. Sulfides can be converted to the sulfoxides and sulfones by oxidation with suitable reagents such as m-CPBA or potassium peroxymonosulfate.

Diol starting materials of formula 21

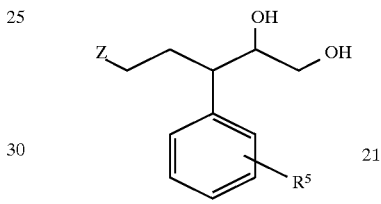

wherein Z and $R^5$ are as defined above, can be prepared as shown in the following reaction scheme:

Step 1:

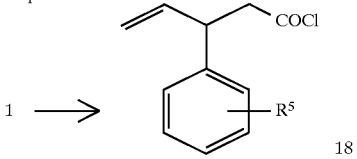

In step 1, compound 1 is dissolved in an inert organic solvent such as $CH_2Cl_2$ or toluene, preferably $CH_2Cl_2$, and treated with a reagent such as $(COCl)_2$, $SOCl_2$ or $PCl_3$, most preferably $(COCl)_2$, in the presence of a catalytic amount of DMF and at temperatures from 0° to 75° C. to give compound 18.

Step 2:

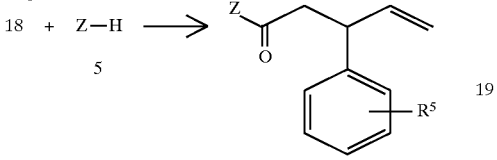

In step 2, compound 18 is dissolved in pyridine at room temperature and treated with an amine of formula 5 as defined above, to give the compound 19. Alternatively, compound 18 is dissolved in an inert organic solvent such as $CH_2Cl_2$ or toluene, preferably $CH_2Cl_2$, the mixture is cooled to 0° C. and a tertiary amine base such as $Et_3N$ or $(CH_3)_3N$ is added, followed by an amine 5.; the reaction is allowed to warm to room temperature to give the product 19. Other coupling methods known to those skilled in the art, such as EDC coupling, may also be employed.

Step 3:

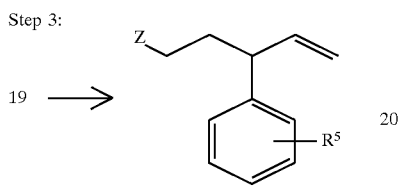

In step 3, the amide 19 is converted to the corresponding amine by standard reduction procedures, for example, it is taken up in an inert organic solvent and treated with a reducing agent at 0° to 80° C. to give the amine 20. Suitable solvents include ether, THF, $CH_2Cl_2$ and toluene, preferably THF. Reducing agents include LAH, $BH_3 \cdot Me_2S$ and DiBAL-H, preferably LAH.

Step 4:

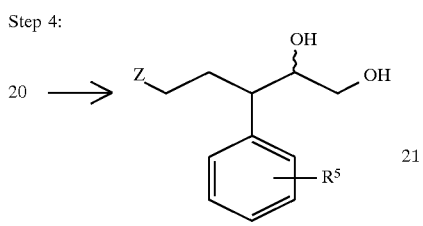

In step 4, the amine 20 is converted to the diol 21 by standard dihydroxylation procedures, for example, it is dissolved in a mixture of acetone and water at room temperature and treated with NMO and $OsO_4$.

Intermediate furanones for use in Procedure A, for example those of formula 62, can be prepared as follows:

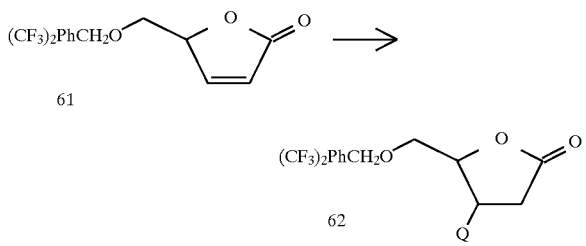

A furanone of formula 61 undergoes conjugate addition with a variety of nucleophiles, e.g., thiolates, azides and aryl anions to obtain compounds of formula 62. For example, compounds of formula 62 wherein Q is phenyl is prepared by treating 61 with phenyllithium in the presence of CuCN and $(CH_3)_3SiCl$.

In the above procedures, T and Q generally are exemplified as $R^5$-phenyl and $R^4$-phenyl, respectively, but those skilled in the art will recognize that in many cases, similar procedures can be used to prepare compounds wherein T and Q are other than substituted-phenyl.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \NH/ | \NCOalkyl/, \NCObenzyl/, \NCOphenyl/, \NCH₂OCH₂CH₂Si(CH₃)₃/, \NC(O)OC(CH₃)₃/, \N-benzyl/, \NSi(CH₃)₃/, \NSi—C(CH₃)₃ with CH₃ groups/ |
| —NH₂ | succinimide (—N(C=O)CH₂CH₂(C=O)) |
| —OH | —OCH₃, —OCH₂OCH₃, —OSi(CH₃)₃, —OSi—C(CH₃)₃ with CH₃ groups, or —OCH₂phenyl |

Compounds of formula I have been found to be antagonists of $NK_1$ and/or $NK_2$ and/or $NK_3$ receptors, and are therefore useful in treating conditions caused or aggravated by the activity of said receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution The pharmaceutical compositions can be prepared with conventional excipients and additives, using well known pharmaceutical formulation techniques. Pharmaceutically acceptable excipients and additives include non-toxic and chemically compatibile fillers, binders, disintegrants, buffers, preservatives, anti-oxidants, lubricants, flavorings, thickeners, coloring agents, emulsifiers and the like.

The daily dose of a compound of formula I for treating asthma, cough, bronchspasm, inflammatory diseases, migraine, nociception and gastrointestinal disorders is about 0.1 mg to about 20 mg/kg of body weight per day, preferably about 0.5 to about 15 mg/kg. For an average body weight of 70 kg, the dosage range is therefore from about 1 to about 1500 mg of drug per day, preferably about 50 to about 200 mg, more preferably about 50 to about 500 mg/kg per day, given in a single dose or 2–4 divided doses. The exact dose, however, is determined by the attending clinician and is dependent on the potency of the compound administered, the age, weight, condition and response of the patient.

Following are examples of preparing starting materials and compounds of formula I. As used herein, Me is methyl, Bu is butyl, Br is bromo, Ac is acetyl, Et is ethyl and Ph is phenyl.

PREPARATION 1

α-[[[(3.5-bis(trifluoromethyl)phenyl]methoxy]methyl]-β-(3.4-dichlorophenyl)-4-hydroxy-4-phenyl 1-piperidinebutanol

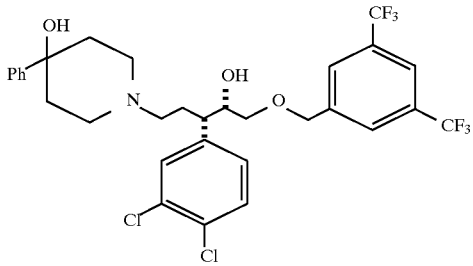

Step 1: Cool a solution of 3-(3,4-dichlorophenyl)-2-propeneoic acid (100 g, 461 mmol) in dry DMF (500 mL) to 0° C. and treat with $Cs_2CO_3$ (100 g, 307 mmol, 0.66 eq). Stir the resulting off-white slurry for 15 min, then add $CH_3I$ (33 mL, 530 mmol, 1.15 eq) via syringe. After 1 h, add additional DMF (250 mL), stir the slurry for 14 h and partition between EtOAc (1.5 L) and half saturated aqueous $NaHCO_3$ (500 mL). Separate the organic layer and extract the aqueous layer twice with EtOAc (1 L, 500 mL). Wash the combined organic layers with half saturated aqueous $NaHCO_3$ (500 mL) and water (5×500 mL), then dry ($Na_2SO_4$) and concentrate to obtain 105.4 g (456 mmol, 99%) of methyl 3-(3,4-dichlorophenyl)-2-propenoate as light brown needles.

Step 2: Treat a solution of the product of Step 1 (15 g, 65 mmol) in dry THF (250 mL), kept cool in a large ambient temperature water bath, with Dibal-H (140 mL, 140 mmol, 2.15 eq) over 30 min. Stir the resulting solution for 30 min at 23° C., pour into $Et_2O$ (500 mL), treat with water (5 mL), 15% NaOH (5 mL) and water (15 mL). Stir for 5 min, dilute the mixture with $Et_2O$ (200 mL) and treat with 15% NaOH (15 mL). Add $MgSO_4$ to cause a colorless precipitate. Remove the aluminum salts by filtration through a course glass frit. Wash the solids with $Et_2O$ (1 L) and concentrate the filtrate in vacuo to give 13.2 g (65 mmol, 99%) of 3-(3,4-dichlorophenyl)-2-propene-1-ol as an off-white solid.

Step 3: Treat a solution of the product of step 2 (13.2 g, 65 mmol) in $CH_2Cl_2$ (250 mL) at 0° C. with pyridine (7.89 mL, 97.5 mmol, 1.5 eq) and dimethylaminopyridine (397 mg, 3.25 0.05 eq), followed by $CH_3COCl$ (6.48 mL, 74.75 mmol, 1.15 eq). Allow the mixture to warm to 23° C., pour into 1M HCl (100 mL) and wash the resulting organic layer again with 1 M HCl (100 mL), followed by water (5×100 mL; pH=6.5–7). Dry the organic layer ($Na_2SO_4$) and concentrate to obtain 15.4 g (62.9 mmol, 97%) of 3-(3,4-dichlorophenyl)-2-propene-1-ol acetate as a colorless oil.

Step 4: Treat a solution of the product of step 3 (15 g, 61 mmol, dried by azeotropic distillation with toluene, 1×50 mL) in dry THF (250 mL) at −78° C. with chlorotriethylsilane (20.2 mL, 120 mmol, 2.0 eq) rapidly followed by the addition of potassium bis(trimethylsilyl)amide (183 mL, 91.5 mmol, 1.5 eq of 0.5M in toluene) via addition funnel over 50 min. Allow the mixture to warm to 23° C. and heat to reflux for 3 h. Gradually cool the solution overnight, then quench with saturated $NH_4Cl$ (150 mL). Stir the resultant mixture vigorously for 3h, treat with 1M HCl (150 mL) and then extract with $Et_2O$ (500 mL). Extract the aqueous layer with $Et_2O$ (400 mL), wash the combined organic layers with 5% NaOH (300 mL) and extract with 5% NaOH (8×150 mL). Cool the combined aqueous layers to 5° C. and, maintaining the temperature at 5°–10° C., acidify with conc. HCl (ca 175 mL) to pH 1. Extract the aqueous layer with $CH_2Cl_2$ (2×800 mL), dry ($Na_2SO_4$) and concentrate to give 13.4 g (54.5 mmol, 89%) of 3-(3,4-dichlorophenyl)-4-pentenoic acid as a faint yellow oil.

Step 5: Treat a solution of the product of step 4 (5.0 g, 20.4 mmol) in dry $CH_2Cl_2$ (60 mL) with purified m-CPBA (7 g, 40 mmol, 2 eq) [wash 13 g of commercial 55% mCPBA in 250 mL of benzene with pH 7.4 buffer (5×30 mL), dry ($Na_2SO_4$) and concentrate to obtain about 9 g of pure m-CPBA]. Stir for 48 h, add Amberlyst 15 (1.2 g) and stir the mixture for 8 h. Remove the Amberlyst by filtration through a medium porosity glass frit, rinsing with EtOAc. Wash the filtrate with saturated $Na_2SO_3$:$NaHCO_3$ (1:1) (100 mL). Dry the resulting organic layer and concentrate in vacuo. Take up the crude resulting product in hexahe:$CH_2Cl_2$ (1:1) and filter to give 3.3 g (12.6 mmol, 62%) of a mixture of isomers (3:2, trans/cis) of 4-(3,4-dichlorophenyl)-dihydro-5-(hydroxymethyl) 2(3H)-furanone as a colorless soft solid. Concentrate the filtrate to give 2.0 g of a viscous oil. Purify the oil by silica gel chromatography (column: 7×15 cm; solvent: hexane:EtOAc, 5:4 gradient to 1:1) to give 1.07 g (4.1 mmol, 20%) of the pure cis isomer as an oil to give a total yield of 4.3 g (16.47 mmol, 81%).

Step 6: Treat a solution of the product of step 5 (3.3 g, 12.6 mmol, 3:2 ratio of stereoisomers by NMR) in dry DMF(10 mL) with 3,5-bistrifluoro-methylbenzyl bromide (5.9 mL, 32.2 mmol, 2.5 eq) followed by $Ag_2O$ (5.8 g, 25.3 mmol, 2 eq), wrap the vessel in foil and stir for 2.5 days. Apply the resultant crude material to a pad of silica gel (10 cm×4 cm) packed with hexane:EtOAc (1:1). Wash the pad with the same solvent until no further product is eluted as shown by TLC and concentrate the resulting filtrate in vacuo to give the crude product as a solid (10 g). Dissolve the resultant residue in hexane:EtOAc (4:1) and purify by silica gel chromatography (column: 7.5×19; solvent: hexane:EtOAc (4:1)) to give 3.33 g (6.8 mmol, 54%) of (trans)-[[[(3,5-bis(trifluoromethyl)phenyl]methoxy]methyl]-4-(3,4-dichlorophenyl)-dihydro-2(3H)-furanone and 1.08 g (2.2 mmol, 17%) of the corresponding cis isomer for a total yield of 71%. Trans isomer: HRMS (FAB, M+H$^+$): m/e calc'd for $[C_{20}H_{15}O_3Cl_2F_6]^+$: 487.0302, found 487.0312. Cis isomer: HRMS (FAB, M+H$^+$): m/e calc'd for $[C_{20}H_{15}O_3Cl_2F_6]^+$: 487.0302, found 487.0297.

Step 7: Cool a solution of the cis isomer of the product of step 6 (2.1 g, 4.31 mmol) in dry $CH_2Cl_2$ (50 mL) to −78° C. and treat with Dibal-H (5.1 mL, 5.1 mmol, 1.2 eq; 1M in $CH_2Cl_2$). Stir for 2 h at −78° C., then treat the solution with NaF (905 mg, 22 mmol, 5 eq) and water (400 μL, 22 mmol, 5 eq). Allow the suspension to warm to 23° C. and stir for 45 min. Dilute the mixture with $Et_2O$ (50 mL) and filter through a pad of silica gel (6.5 cm×2 cm; 150 mL vacuum glass frit) packed with hexane:EtOAc (1:1). Wash the pad with hexane:EtOAc (1:1) until no further product is evident by TLC (ca. 600 mL). Concentrate the filtrate to give 1.92 g (3.86 mmol, 91%) of (cis)-[[[(3,5-bis(trifluoromethyl)phenyl]methoxy]methyl]-4-(3,4-dichlorophenyl)-tetrahydro-2-furanol as a foam which is used without further purification.

Step 8: Treat a solution of the product of step 7 (1.92 g, 3.86 mmol) in 2,2,2 trifluoroethanol (10 mL) with powdered 3Å MS (3.5 g) followed by 4-hydroxy-4-phenylpiperidine. Stir the resulting suspension under $N_2$ for 1 h at 23° C., then add $NaCNBH_3$ (533 mg, 8.6 mmol, 2 eq) and stir for 20 h. Filter the resultant mixture through a pad of silica gel (9.5 cm×2.5 cm, 600 mL, vacuum glass frit) packed and eluted with EtOAc:triethylamine (9:1) (ca. 500 mL) until no further product is apparent by TLC. Remove the solvent to obtain 2.77 g (>90%) of the title compound as a colorless foam. HRMS (FAB, M+Na$^+$): m/e calc'd for $[C_{31}H_{32}NO_3Cl_2F_6]^+$: 650.1663, found 650.1647.

Preparation 2

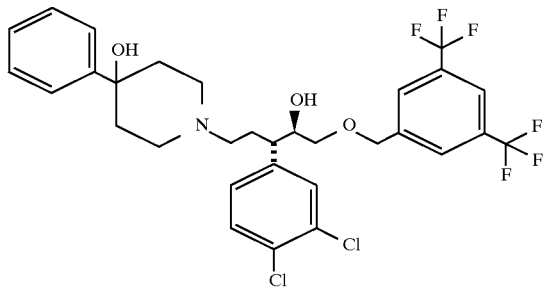

Using the trans isomer of Preparation 1, step 6, carry out the procedure of Preparation 1, steps 7–8 to obtain the title compound. HRMS (FAB, M+H$^+$): m/e calc'd for $[C_{31}H_{32}NO_3Cl_2F_6]^+$: 650.1663, found 25 650.1654.

Preparation 3

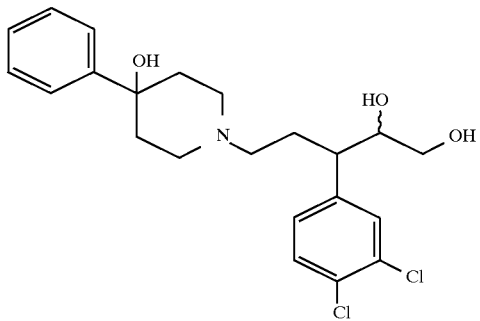

Steps 1–2: Treat a solution of the product of Preparation 1, step 4 (1.6 g, 6.5 mmol) in dry benzene (15 mL) at 5° C. with ClCOCOCl (680 μL, 7.8 mmol, 1.2 eq) followed by DMF (10 μL). Stir the resulting solution for 3 h at 23° C., concentrate in vacuo, azeotrope with benzene (1×15 mL), dissolve in dry CH$_2$Cl$_2$ (15 mL) and cool to 0° C. Treat a solution of 4-hydroxy-4-phenyl piperidine (2.3 g, 13 mmol, 2 eq) in dry CH$_2$Cl$_2$ (20 mL) with pyridine (1.57 mL, 19.5 mmol, 3 eq) and cool to 0° C. Add the acid chloride via cannula over a period of 20 min. Stir the resulting solution for 15 min, warm to 23° C., dilute with CH$_2$Cl$_2$ (150 mL) and wash consecutively with 10% aqueous citric acid (2×50 mL), water (1×50 mL) and aqueous saturated NaHCO$_3$ (1×50 mL), dry (Na$_2$SO$_4$) and concentrate. Purify the crude product by silica gel chromatography (column: 7×14 cm; eluant: hexane/EtOAc (1:1) (1 L) gradient to hexane/EtOAc (3:5) (2 L)) to provide 1.995 g (494 mmol, 76%) of the desired amide as a colorless solid.

Step 3: Treat a solution of the amide from step 2 (4.1 1g, 10.2 mmol) in dry THF (50 mL) with LiAlH$_4$ (20.4 mL of 1M solution in ether, 20.4 mmol, 2 eq). Stir for 30 min at 23° C., then pour the mixture into Et$_2$O (300 mL) and treat with water (750 μL), then 15% NaOH (750 μL) followed by water (3 mL). Remove the resulting aluminum salts by filtration through a glass frit, concentrate the filtrate, dissolve in hexane/EtOAc/triethyl amine (49:49:2) and filter through a plug of silica gel (10×4 cm), eluting with 800 mL of solvent. Concentrate the filtrate to give 3.38 g (8.67 mmol, 85%) of the desired amine as a yellow oil.

Step 4: Treat a solution of the product of step 3 (3.0 g, 7.69 mmol) in acetone/water (15 mL /30 mL) with NMO (1.35 g, 11.5 mmol, 1.5 eq) followed by OsO$_4$ (3.9 mL of 2.5% w/w solution in t-butanol, 0.38 mmol, 0.05 eq). After stirring for 17 h, treat the mixture with saturated aqueous Na$_2$SO$_3$ (100 mL) and stir for 1 h. Concentrate the mixture in vacuo, extract the resulting aqueous solution with CH$_2$Cl$_2$ (3×100 mL), dry the resulting organic layer (Na$_2$SO$_4$) and concentrate. Purify the crude product by silica gel chromatography (7×20 cm; eluant: gradient: CH$_2$Cl$_2$/CH$_3$OH/ triethylamine (180:5:150) to (140:5:50) to (100:5:150) to (10:1:1) to obtain 932 mg (2.19 mmol, 29%) of the trans diol as light amber oil and 1.455 g (3.4 mmol, 45%) if the cis diol as a colored oil. Pool mixed fractions to obtain an additional 221 mg of product as a mixture of isomers, giving a total yield of 6.11 mmol, 80%.

HRMS (FAB, M+H$^+$): m/e calc'd for $[C_{22}H_{28}Cl_2NO_3]^+$: 424.1446, found 424.1435.

Preparation 4

1[[(3.5-bis(trifluoromethyl)phenyl]methoxy]-3-(3,4-dichlorophenyl)-5-(4-hydroxy-4-phenyl-1-piperidinyl)-2-pentanone

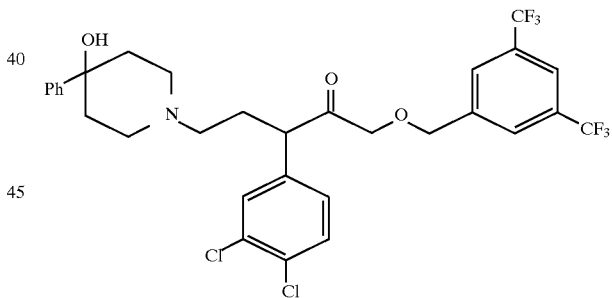

Treat a solution of the product of Preparation 1 (2.0 g, 3.08 mmol) in acetone (90 mL, 0° C.) with Jones reagent (9 mL of H$_2$CrO$_4$ in H$_2$SO$_4$ (ca. 8M)). Stir the light orange suspension at 0° C. for 1 h, then partition between CH$_2$Cl$_2$ (150 mL) and saturated aqueous NaHCO$_3$ (150 mL). Extract the aqueous layer with CH$_2$Cl$_2$ (3×150 mL), back extract the combined organic layers with saturated aqueous NaHCO$_3$ (150 mL), dry (Na$_2$SO$_4$) and concentrate to give 1.94 g crude product. Purify by silica gel chromatography (column: 4 cm×15 cm; eluant: EtOAc:hexane: triethylamine (66:33:2)) to obtain 1.64 g (2.53 mmol, 82%) of the title compound as a colorless foam.

HRMS (FAB, M+H$^+$): m/e calc'd for $[C_{31}H_{30}NO_3Cl_2F_6]^+$: 648.1507, found 648.1496.

Preparation 5

β-(3,4-dichlorophenyl)-4-hydroxy-α-[(methylphenylamino)methyl]-4-phenyl-1-piperidinebutanol

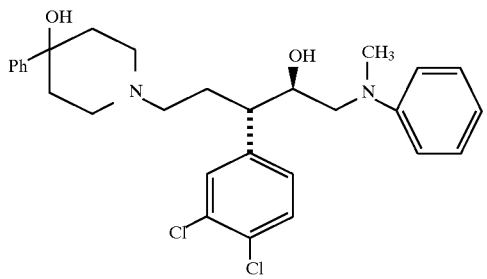

Step 1: Cool a solution of the product of Preparation 1, step 4 (6.4 g, 26 mmol) in dry $CH_3CN$ to 0° C. and treat with $I_2$ (19.8 g, 78 mmol, 3 eq). Store the solution at 0° C. for 100 h, then pour into saturated aqueous $NaHCO_3$ (250 mL)/saturated aqueous $Na_2SO_3$ (100 mL)/$Et_2O$ (400 mL). Extract the aqueous layer with $Et_2O$ (200 mL) and wash the combined $Et_2O$ layers with a mixture of saturated aqueous $Na_2SO_3$ (25 mL) and brine (100 mL). Dry the organic layer over $MgSO_4$ and concentrate to give a light yellow solid. Purify the crude material by recrystallization (hot isopropanol, 2×) to obtain 7.42 g (19.9 mmol, 77%) of 4-(3,4-dichloro-phenyl)-dihydro-5-(iodomethyl)-2(3H)-furanone as an off-white solid.

Step 2: Treat a solution of the product of step 1 (1.5 g, 4.02 mmol) in dry $CH_3OH$ (15 mL) under $N_2$ with $Cs_2CO_3$ (1.57 g, 4.8 mmol, 1.2 eq). Stir for 30 min, then pour the suspension into $Et_2O$ (200 mL)/water (100 mL). Extract the aqueous layer with $Et_2O$ (100 mL), wash the combined ether layers with 40 mL of saturated NaCl, dry ($MgSO_4$), and concentrate to give 1.11 g (4.02 mmol,>99%) of methyl β-(3,4-dichlorophenyl)-oxiranepropanoate as a colorless oil.

Step 3: Treat a solution of the product of step 2 (368 mg, 1.34 mmol) in 2,2,2 trifluoroethanol (1 mL) with N-methyl aniline (217 μL, 2.01 mmol, 1.5 eq) and stir for 6 h at 23° C. followed by 6 h at 80° C. Cool to 23° C., concentrate in vacuo and purify by silica gel chromatography (column: 3.5×12 cm; eluant: hexane:EtOAc (4:1)) to provide 446 mg (1.3 mmol, 97%) of 4-(3,4-dichlorophenyl)-dihydro-5-[(methylphenylamino)methyl]-2(3H)-furanone as a white solid.

Step 4: Cool a solution of the product of step 3 (435 mg, 1.24 mmol) in dry $CH_2Cl_2$ (10 mL) to −78° C. and treat with Dibal-H (1.56 mL, 1M in $CH_2Cl_2$). Stir the solution for 2 h, then add NaF (273 mg, 6.5 mmol, 5 eq) and water (117 μL, 6.5 mmol, 5 eq). Dilute the mixture with $Et_2O$ (100 mL) and warm to 23° C. Treat the mixture with $MgSO_4$, stir for 10 min, filter through a sintered glass frit and concentrate. Take up the residue in hexane:EtOAc (1:1) and filter through a pad of silica gel (7×2 cm) with about 150 mL of hexane:EtOAc (1:1). Concentrate the filtrate to obtain 415 mg (1.17 mmol, 95%) of the desired lactol as a colorless film.

Step 5: Treat a solution of the product of step 4 (415 mg, 1.17 mmol) in 2,2,2 trifluoroethanol with 4-hydroxy-4-phenyl piperidine (450 mg, 2.54 mmol, 2 eq) and 3Å MS (1 g). Stir for 2h, treat the mixture with $NaCNBH_3$ (157 mg, 2.54 mmol, 2 eq) and stir the resulting suspension vigorously for 16 h. Evaporate the solvent in vacuo, take up the crude in EtOAc, apply to a silica gel column (3.5×12 cm) packed with hexane:EtOAc:triethylamine (66:33:2) and elute with gradient elution: EtOAc:triethyl amine (98:2) to EtOAc:$CH_3OH$:triethylamine (80:20:2), to obtain 569 mg (1.11 mmol, 95%) of the title compound as a colorless foam.

HRMS (FAB, M+H$^+$): m/e calc'd for $[C_{29}H_{35}N_2O_2Cl_2]^+$: 513.2076, found 513.2063.

Compounds of Preparations 5A to 5C are prepared in a similar manner, using the appropriate amines in step 3:

| Prep. | T | Amine | HRMS calc'd (FAB, M + H$^+$) | HRMS Found |
|---|---|---|---|---|
| 5A | ![CF3 structure] | N-methyl-(3,5-bistri-fluoromethyl-phenyl)benzyl amine | 633.1980 | 633.1995 |
| 5B | ![phenyl structure] | N-methyl benzyl amine | 527.2232 | 527.2246 |
| 5C | ![isopropoxy structure] | N-methyl-(3-isopropoxy)benzyl amine | 585.2651 | 585.2644 |

Preparation 6

Substituted Piperidines—Method A

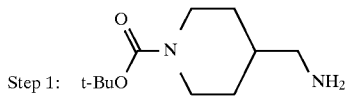

Dissolve 4-aminomethyl-piperidine (30.00 g, 0.263 mol) in $CH_3OH$ (500 mL), cool to −30° C. under $N_2$, add di-t-butyl dicarbonate (38.23 g, 0.175 mol) in $CH_3OH$ (100 mL) dropwise, warm slowly to 23° C. and stir for 16 h. Concentrate, add $CH_2Cl_2$ (700 mL), wash with saturated aqueous NaCl (2×200 mL), dry organic solution ($MgSO_4$), filter and concentrate to give 36.80 g of a 86:14 mixture of the title compound and 1,1-dimethyl-ethyl 4-[(1,1-dimethylethyloxycarbonyl)methyl]-1-piperidinecarboxylate.

Step 2A:

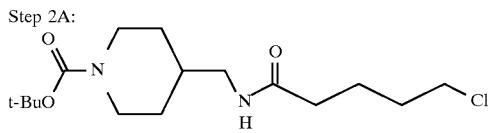

Dissolve the product (19.64 g, 0.0916 mol, 22.84 g of the mixture) of Step 1 in dry CH$_2$Cl$_2$ (350 mL) and cool to 0° C. under N$_2$. Add pyridine (10.87 g, 11.1 mL, 0.137 mol) then chlorovaleryl chloride (15.63 g, 13.0 mL, 0.101 mol), warm slowly to 23° C. and stir for 16 h. Add saturated aqueous NH$_4$Cl (300 mL), separate layers and extract with CH$_2$Cl$_2$ (2×250 mL). Dry combined organic extracts (MgSO$_4$), filter and concentrate. Purify by chromatography (1000 mL of flash silica gel; eluant: 1:1 EtOAc:hexane, then EtOAc). Combine appropriate fractions and concentrate to give 25.36 g (0.0762 mol. 84%) as a colorless oil.

MS (Cl/CH$_4$): m/e 333 (M+1)

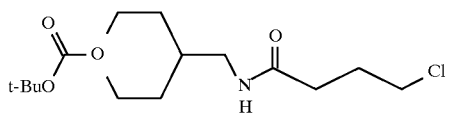

Step 2B:

Treat the product of Step 1 in a procedure similar to that described for Step. 2A, using chlorobutryl chloride. MS (FAB): m/e 319 (M+1)

Step 3:

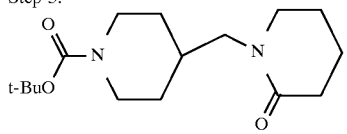

Prep. 6A:

Wash NaH (3.84 g, 0.160 mol, 6.40 g of 60 wt %) with hexane (25 mL), suspend in dry THF (150 mL) and cool to 0° C. under N$_2$. Add the product (25.35 g, 0.0762 mol) of Step. 2A in dry THF (150 mL) dropwise. Stir at 23° C. for 30 mins, reflux for 6 h, and stir at 23° C. for 16 h. Cool to 0° C. and add water (150 mL) and 1N HCl (150 mL). Concentrate and extract with EtOAc (3×200 mL). Wash combined organic extracts with saturated aqueous NaCl, dry (MgSO$_4$), filter and concentrate. Purify by chromatography (600 mL of flash silica gel; eluant: 5% CH$_3$OH—CH$_2$Cl$_2$). Combine appropriate fractions and concentrate to give 21.62 g (0.0729 mol, 96%) of the title compound as a yellow oil. MS (FAB): m/e 297 (M+1)

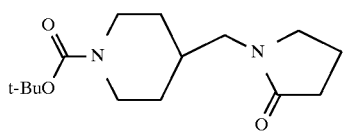

Prep. 6B:

Treat the product of Step 2B in a procedure similar to that described for Prep. 6A. MS (FAB): m/e 283 (M+1).

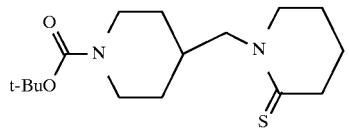

Prep. 6C:

Combine the product (1.50 g, 5.06 mmol) of Prep. 6A and Lawesson reagent (1.13 g, 2.78 mmol) in dry THF (20 mL) under N$_2$. Stir at 23° C. for 20 h. Concentrate and purify by chromatography (200 mL of flash silica gel; eluant: 1:3 EtOAc:hexane, 1:2 EtOAc:hexane, then 1:1 EtOAc:hexane). Combine appropriate fractions and concentrate to give 1.30 g (4.16 mmol, 82%) as a green oil. MS (FAB): m/e 313 (M+1).

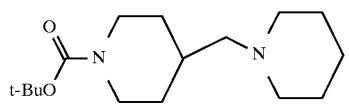

Prep. 6D:

Dissolve the product (2.50 g, 8.43 mmol) of Prep. 6A in dry THF (30 mL), add borane-DMS (16.9 mL of 2.0M in THF, 33.74 mmol) and reflux for 20 h. Cool to 0° C. and add CH$_3$OH (20 mL). Concentrate, add EtOH (50 mL) and K$_2$CO$_3$ (4.66 g, 33.74 mmol). Reflux for 4 h and cool to 23° C. Add water (100 mL), concentrate and extract with CH$_2$Cl$_2$ (4×50 mL). Dry combined organic extracts (MgSO$_4$), filter and concentrate. Purify by chromatography (200 mL of flash silica gel; eluant: 7% CH$_3$OH—CH$_2$Cl$_2$). Combine appropriate fractions and concentrate to give 1.72 g (6.09 mmol, 72%) of the title compound as a colorless oil. MS (FAB): m/e 283 (M+1).

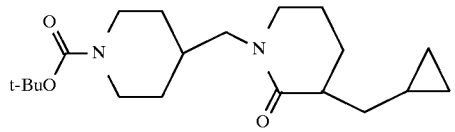

Prep. 6E:

Dissolve the product (1.50 g, 5.06 mmol) of Prep. 6A in dry THF (20 mL) and cool to −78° C. under N$_2$. Add [(CH$_3$)$_3$Si]$_2$NLi (5.5 mL of 1.0M in THF, 5.5 mmol) and stir at −78° C. for 1 h. Add bromomethylcyclopropane (0.820 g, 0.59 mL, 6.07 mmol), warm slowly to 23° C. and stir for 16 h. Add saturated aqueous NH$_4$Cl (40 mL), extract with EtOAc (3×30 mL), wash combined organic extracts with saturated aqueous NaCl, dry (MgSO$_4$), filter and concentrate. Purify by chromatography (175 mL of flash silica gel; eluant: 2% CH$_3$OH—CH$_2$Cl$_2$ then 4% CH$_3$OH—CH$_2$Cl$_2$). Combine appropriate fractions and concentrate to give 0.93 g (2.65 mmol, 53%) of the title compound as a colorless oil. MS (FAB): m/e 351 (M+1)

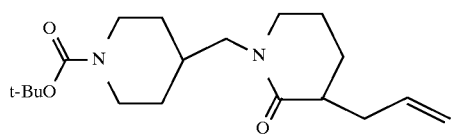

Prep. 6F:

Treat the product of Prep. 6A in a procedure similar to that described for Prep. 6G, using allyl bromide. MS (Cl/CH$_4$): m/e 337 (M+1). Step 3: Separately dissolve the products of Prep. 6A to 6H in CH$_2$Cl$_2$, add trifluoroacetic acid and stir at 23° C. for 4 h. Concentrate, add 1N NaOH, extract with CH$_2$Cl$_2$, dry the combined organic extracts (MgSO$_4$), filter and concentrate to obtain the corresponding substituted piperidines:

| Prep. | Substituted Piperidine | Data |
|---|---|---|
| 6-1 | | MS (Cl/CH$_4$): m/e 197 (M + 1) |
| 6-2 | | MS (Cl/CH$_4$): m/e 183 (M + 1) |
| 6-3 | | MS (Cl/CH$_4$): m/e 213 (M + 1) |
| 6-4 | | MS (Cl/isobutane: m/e 183 (M + 1) |
| 6-5 | | MS (Cl/CH$_4$): m/e 251 (M + 1) |
| 6-6 | | MS (Cl/CH$_4$): m/e 237 (M + 1) |

Preparation 7

Substituted Piperidines—Method B

Step 1:

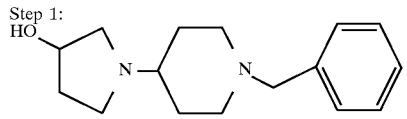

Prep. 7A:

Combine 1-benzyl-4-piperidone (2.00 g, 10.6 mmol) and 3-pyrrolinol (0.92 g, 10.6 mmol) in titanium isopropoxide (3.75 g, 3.9 mL, 13.2 mmol) and dry CH$_2$Cl$_2$ (4 mL). Stir at 23° C. under N$_2$ for 5 h. Add EtOH (30 mL) and NaCNBH3 (0.66 g, 10.6 mmol) and stir for 16 h. Add water (50 mL) and CH$_2$Cl$_2$ (50 mL), filter through celite, separate filtrate layers and extract with CH$_2$Cl$_2$ (2×50 mL). Wash combined organic extracts with saturated aqueous NaHCO$_3$, dry (MgSO$_4$), filter and concentrate. Purify by chromatography (150 mL of flash silica gel; eluant: 10% CH$_3$OH with NH$_3$—CH$_2$Cl$_2$, 15% CH$_3$OH with NH$_3$—CH$_2$Cl$_2$, then 20% CH$_3$OH with NH$_3$—CH$_2$Cl$_2$.) Combine appropriate fractions and concentrate to give 1.88 g (7.22 mmol, 68%) as a colorless oil.

MS (Cl/CH$_4$): m/e 261 (M+1).

Using the procedure of Prep. 7A and the appropriate amine, prepare Preps. 7B and 7C:

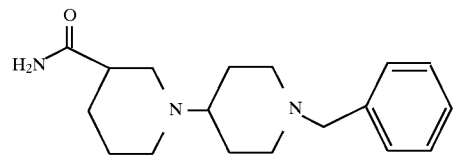

Prep. 7B:
MS(FAB): m/e 302 (M+1)

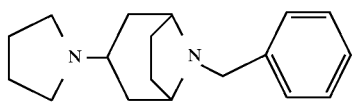

Prep.7 C:
MS(Cl/CH₄): m/e271 (M+1).

Step 2: Separately treat each of Preps. 7A, 7B and 7C with Pd/C catalyst in CH₃OH and formic acid at 23° C. under N₂ for 16 h. Filter each mixture through celite, washing with CH₃OH, concentrate the filtrates, add 1.0N NaOH and extract with 1:4 EtOH:CH₂Cl₂, dry, filter and concentrate to obtain Preps. 7-1, 7-2 and 7-3:

| Prep. | Substituted Piperidine | Data |
|---|---|---|
| 7-1 | | MS (Cl/CH₄): m/e 171 (M + 1) m.p. 138–140° C. |
| 7-2 | | MS (Cl/CH₄): m/e 212 (M + 1) |
| 7-3 | | MS (Cl/CH₄): m/e 181 (M + 1) |

Preparation 8

Substituted Piperidines—Method C

Step 1: Using 1,1-dimethyethyl 4-formyl-piperidinecarboxylate and the appropriate amine in a reductive amination procedure similar to that described in Example 42, Step 9, Preparations 8A, 8B and 8C are prepared:

Prep. 8A:
MS(Cl/isobutane): m/e313 (M+1)

Prep. 8B:
MS(Cl/CH₄): m/e313 (M+1)

Prep. 8C:
MS(FAB): m/e299 (M+1)

Step 2: Using the procedure described in Preparation 6, Step 3, prepare the following compounds:

| Prep. | Substituted Piperidine | Data |
|---|---|---|
| 8-1 | | MS (FAB): m/e 213 (M + 1) |
| 8-2 | | MS (Cl/CH₄): m/e 213 (M + 1) |
| 8-3 | | MS (Cl/CH₄): m/e 199 (M + 1) |

Preparation 9

Substituted Heptan- and Hexanaldehydes

Step 1:

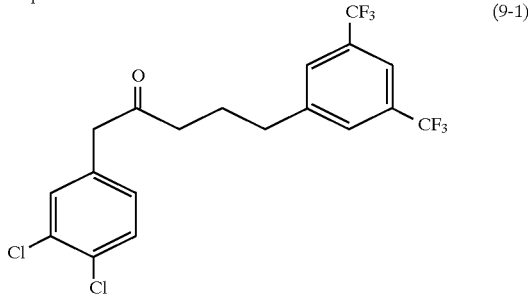

(9-1)

Treat a suspension of 4[3,5-bis(trifluoromethyl)phenyl] butyric acid (5.15 g, 17.55 mmol) in dry Et₂O (50 ml) with SOCl₂ (2.6 ml, 2 equiv.) and add 3 drops of pyridine. Stir for 15 h at ambient temperature, then decant the solution from pyridine hydrochloride and evaporate in vacuo to obtain the acid chloride (5.4 g, 99%) as an oil.

Cool a 1M solution of [(CH₃)₃Si]₂NLi (50 ml, 8.3 g, 49.63 mmol) in THF to −30° C. and add a solution of 3,4-dichlorophenylacetic acid (4.09 g, 19.8 mmol) in dry THF (20 ml) dropwise, maintaining the temperature at or below −14° C. Stir at 0°–5° C. for 1 h. Cool the reaction mixture to −78° C. and add a solution of 4-[3,5-bis (trifluoromethyl)phenyl]butyryl chloride (5.41 g, 15 16.97 mmol) in dry THF (10 ml) dropwise over 15 min. Stir at 0° C. for 1 h, then allow to warm up to room temperature and stir for 1 h. Pour on 50 ml of 1N HCl and ice, stir 30 min and extract the aqueous layer with EtOAc. Wash with saturated aqueous NaHCO₃ (200 ml), dry (MgSO₄), filter and concentrate in vacuo to obtain 7.5 g of crude product. Purify by flash chromatography over 180 g silica gel (particle size 32-63) and elute with hexane: CH₂Cl₂ (70:30) to obtain 3.86 9 (8.71 mmol, 51%) of the title crystalline compound. ¹H NMR (CDCl₃, 300 MHz)δ:7.72(s, 1 H Ar), 7.60(s, 2H Ar), 7.41 (d, J=8.3, 1 H Ar), 7.29(s, 1H Ar), 7.02(m, 1H Ar), 3.66(s, 2H, CH₂),2.72(t, 2H, CH₂, J=7), 2.54(t, 2H, CH₂, J=7), 1.94(m, 2H, CH₂). IR (CH₂Cl₂): 1720 cm⁻¹ (C=O).

Using a similar procedure with the appropriate acid, prepare the following compounds:

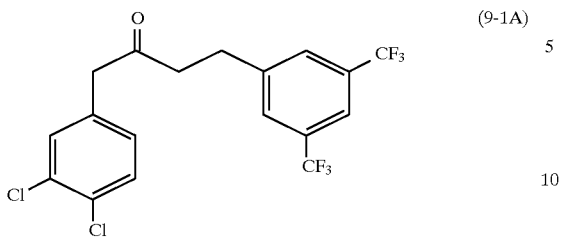
(9-1A)

Yield 66%. $^1$H NMR (CDCl$_3$, 200 MHz)δ: 7.72(s, 1H Ar), 7.60(s, 2H Ar), 7.38(d, 1H Ar, J=8), 7.26(1H Ar), 6.98(m, 1H Ar), 3.65(s,2H, CH$_2$), 3.02(t, 2H, CH$_2$, J=6.4), 2.86(t, 2H, CH$_2$ (t, 2H, CH$_2$, J=6.4)).

IR (CH$_2$Cl$_2$):1720 cm$^{-1}$ (C=O).

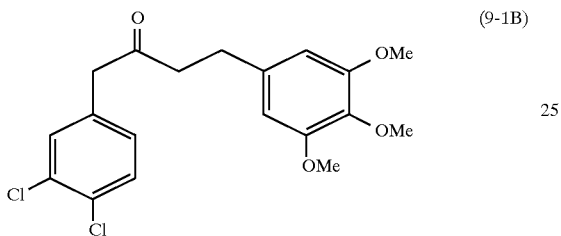
(9-1B)

Yield 60%. FAB-Ms: m/z 383 ([C$_9$H$_{20}$$^{35}$Cl$_2$O$_4$+H]+, 47%).

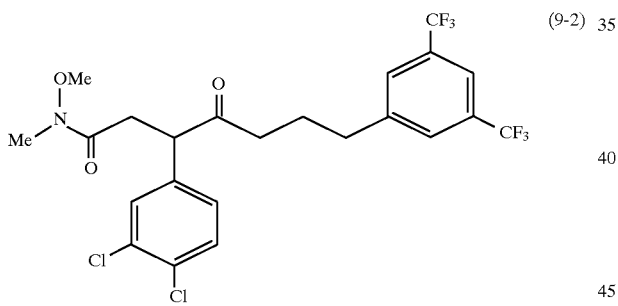
(9-2)

Step 2:

Step 2

Add a solution of the product of Step 1 (3.80 g. 8.57 mmol) in dry THF (20ml) to a stirred solution of [(CH$_3$)$_3$Si]$_2$NLi (9.35 ml, 9.3 mmol) in THF at −78° C. Add a solution of 2-chloro-N-methoxy-N-methyl-acetamide (1.18 g, 8.58 mmol) in THF (10 ml) dropwise over 10 min, add 1.2 g of Kl, allow the reaction mixture to warm to room temperature over a period of 1 h and stir overnight. Add 10 ml of saturated aqueous NH$_4$Cl and evaporate the solvent in vacuo. Partition the residue between CH$_2$Cl$_2$ (150 ml) and H$_2$O (150 ml). Wash the organic layer with aqueous NaHCO$_3$ (150 ml), dry (MgSO$_4$), filter and evaporate in vacuo to obtain 3.6 g (77%) of the oily product.

FAB-Ms: m/z 544 ([C$_{23}$H$_{21}$$^{35}$Cl$_2$F$_6$NO$_3$+H]+, 61%).

Using the procedure of Step 2, treat compounds 9-1A and 9-B of Step 1 to obtain:

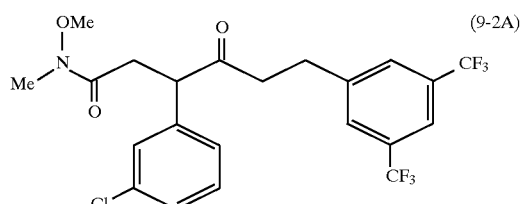
(9-2A)

Yield 77%. FAB-Ms: M/Z 530 ([C$_{22}$H$_{19}$$^{35}$Cl$_2$F$_6$NO$_3$+ H]+, 52%).

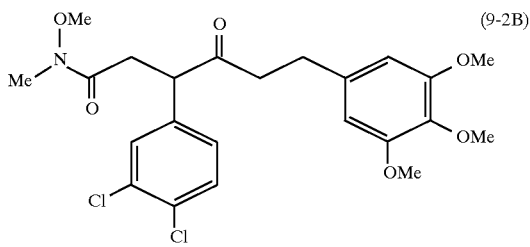
(9-2B)

Yield: 77%. FAB-Ms: m/z 484 ([C$_{23}$H$_{27}$$^{35}$Cl$_2$NO$_6$+ H]+, 30%).

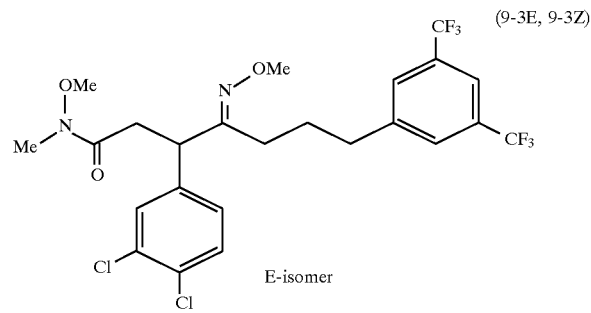
(9-3E, 9-3Z)

Treat a solution of the product of Step 2 (3.5 g, 6.43 mmol) in dry pyridine (10 ml) with 0-methoxylamine HCl (0.65 g, 7.78 mmol) and heat to 60° C. for 1 h. Remove the pyridine in vacuo, partition the residue between CH$_2$Cl$_2$ and water. Dry over MgSO$_4$, filter and evaporate in vacuo to obtain the mixture of E- and Z-oximes. Separate E-oxime and Z-oxime by flash chromatography using 120 g of SiO$_2$ (particle size 32-63) and eluant: EtOAc:hexane (20:80) to obtain 2.91 g (79%) of E-isomer and 0.47 g (12.8%) of Z-isomer.

9-3(E): FAB-Ms (E-isomer): m/z 573 ([C$_{24}$H$_{24}$$^{35}$Cl$_2$F$_6$N$_2$O$_3$+H]+, 27%).
$^1$H NMR- E-isomer (CDCl$_3$, 300 MHz)δ4.08 (H-γ).
9-3(Z): FAB-Ms (Z-isomer): m/z 573 ([C$_{24}$H$_{24}$$^{35}$Cl$_2$F$_6$N$_2$O$_3$+H]+, 70%).
$^1$H NMR- Z-isomer (CDCl$_3$, 300 MHz)δ4.69 (H-γ).

Using the procedure of Step 3, treat compounds 9-3A and 9-3B to obtain the following:

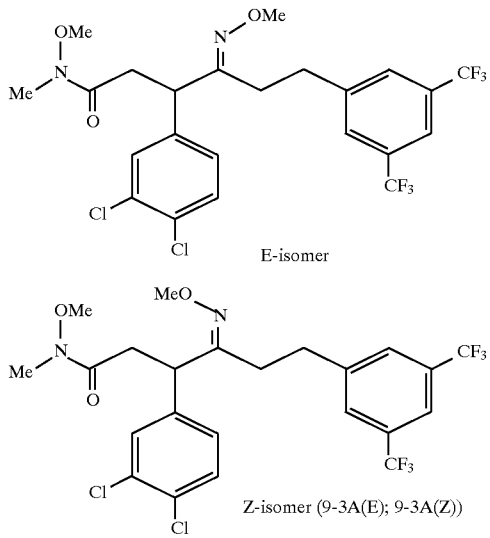

Yield: 73% of E-isomer (m.p. 62°–64° C.) and 18% of Z-isomer.

9-3A(E): Ms-Cl+CH$_4$ (E-isomer): m/z 559 ([C$_{23}$H$_{22}$$^{35}$Cl$_2$F$_6$N$_2$O$_3$+H]$^+$, 100%). $^1$H NMR- E-isomer (CDCl$_3$, 300 MHz)δ4.11 (H-γ).

9-3A(Z): Ms-Cl+/CH$_4$ (Z-isomer): m/z 559 ([C$_{23}$H$_{22}$$^{35}$Cl$_2$F$_6$N$_2$O$_3$+H]$^+$, 100%). $^1$H NMR-Z-isomer (CDCl$_3$, 300 MHz)δ4.71 (H-γ).

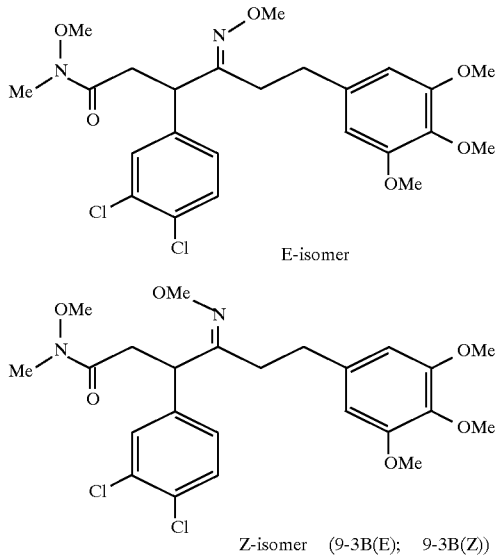

Yield: 61% of E-isomer (m.p. 114°–118° C.) and 23% of oily Z-isomer.

9-3B(E): FAB-Ms (E-isomer): m/z 513 ([C$_{24}$H$_{30}$$^{35}$Cl$_2$N$_2$O$_6$+H]$^+$, 42%).

$^1$H NMR- E-isomer (CDCl$_3$, 300 MHz) 8 4.10 (H-γ).

9-3B(Z): FAB- Ms (Z-isomer): m/z 513 ([C$_{24}$H$_{30}$$^{35}$CL$_2$N$_2$O$_6$+H]$^+$, 60%).

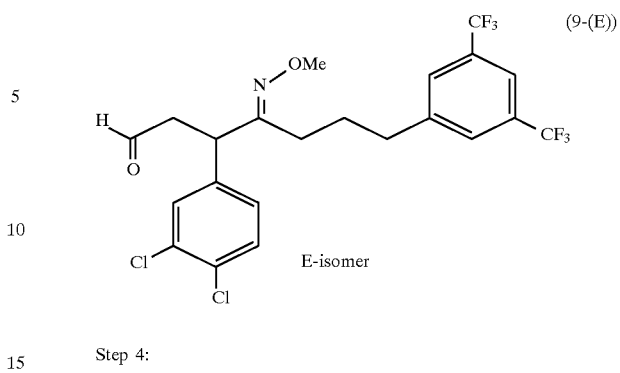

Step 4:

To a solution of the E-isomer of Step 3 (9-3(E)) (1.43 g, 2.54 mmol) in THF (20 ml) at −78° C., add 6 ml of 1M Dibal-H in hexane (6 mmol) over a period of 5 min. Stir at −78° C. for 30 min, then add 15 ml of H$_2$O and 1 g of NaF. Allow the reaction mixture to warm to room temperature, dilute with EtOAc (100 ml), separate organic layer from aqueous, dry (MgSO$_4$), filter and evaporate in vacuo. Treat the residue with Et$_2$O, filter and evaporate in vacuo. Use the product immediately, without purification. Using the procedure described in step 4, treat preparative compounds 9-3A (Z), 9-3B(E) and 9-3B(Z) to obtain the corresponding aldehydes 9-A(Z), 9-B(E) and 9-B(Z).

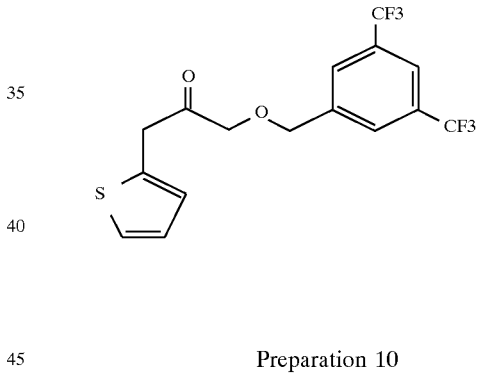

Preparation 10

Treat a solution of 2-thiopheneaceticacid (1.6 g, 11.2 mmole) in anhydrous THF (100 mL, −78° C.) with lithium-hexadimethylsilazide (24.5 mmole, 1M THF soln.). Warm the solution to 0° C. over a period of 2 h, then cool to −78° C. and add ethyl [[3,5-bis(trifluoromethyl)phenyl]-methoxy]-acetate (3.55 g, 11.2 mmole) dropwise as a THF solution (10 mL). Stir the resulting mixture for 4 h and allow the temperature to warm to 0° C. Quench the reaction with 1 ml HOAc and stir for 4h. Dilute the reaction with EtOAc (100 mL), wash the organics with water (2×50 mL) and brine (1×50 mL), dry (Na$_2$SO$_4$) and concentrate to obtain 3.4 g of crude product. Purify by silica gel chromatography (3:7 Et$_2$O:hexane ) to give the title compound, 2.8 g (7.3 mmole, 65.4%) as a colorless foam.

MS: (Cl+/CH$_4$) (M+H$^+$) 383.

Preparation 11

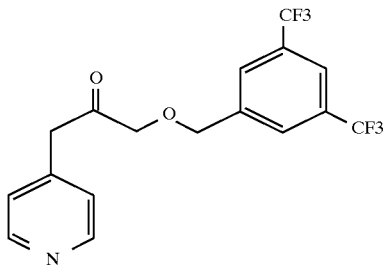

Treat a solution of 4-picoline (1.42g, 15 mmole) in anhydrous THF (50 mL, −10° C.) with phenyllithium (15 mmole, 8.3 mL cyclohexane:Et$_2$O) and stir for 1 h at 0° C. Cool the solution to −78° C. and add the product of Example 47, Step 1 (5.27 g, 15 mmole) dropwise as a THF solution (10 mL). Stir the resulting mixture for 4 h (−78° C. to 0° C.) and quench with saturated aqueous NH$_4$Cl (10 mL). Extract with EtOAc (100 mL), wash with water (2×50mL), brine (50 mL), dry (Na$_2$SO$_4$), and concentrate. Purify the crude by silica gel column chromatography (8:2 EtOAc:hexane) to obtain the title compound. (2.5 g, 44%). MS: (Cl+/CH$_4$) (M+H$^+$) 378.

Preparation 12

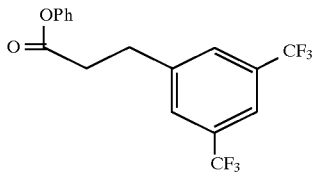

Step 1: Treat a solution of 3,5-bis(triflouromethyl) benzaldehyde (10 g, 0.04 moles) in toluene (130 mL) with carboethoxymethylenetriphenyl-phosphorane (14.38 g, 0.041 moles) and reflux in toluene for six hours. Remove the solvent under vacuum and dissolve the residue in CH$_2$Cl$_2$ and filter through a pad of silica gel (50 g) on a suction filter. Concentrate the filtrate and dry under vacuum to give the title compound (13.01 g) as a white solid. MS(Cl, M+H$^+$), m/e 313.

Step 2: Treat a degassed solution of the product of Step 1 (31.0 g, 0.04 mmoles) in EtOH (60 mL) with 10% Pd/C (1.3 g), introduce H$_2$ gas to a pressure of 20 psi. and shake at room temperature for 2 hours. Filter through celite and remove solvent by vacuum distillation to obtain the title compound (13.0 gm). MS(Cl, M+H$^{3o}$), m/e 315.

Step 3: Treat an EtOH solution (200 mL) of the product of Step 2 (13 g, 0.041 moles) with an aqueous solution of NaOH (50%, 12 ml, 0.26 moles). Heat the solution at reflux for 3 h. Cool the mixture to room temperature and remove the solvent by vacuum distillation. Dissolve the residue in water (150 mL) and acidify to pH 2 with concentrated HCl. Extract the product into EtOAc (2×100 mL), wash the EtOAc layer with water (2×50 mL), dry (MgSO$_4$) and remove the solvent by vacuum distillation to afford a white solid (11.26 g). M. p. 65°–67° C. MS (Cl, M+H$^+$) m/e 287.

Step 4: Treat a solution of the product of Step 3 (11.26 g, 0.039 moles) in CH$_2$Cl$_2$ (300 mL) with oxalyl chloride (5.99 g, 0.047 moles, added dropwise with stirring) and a trace of DMF. Stir the mixture at room temperature for 2 h and heat to reflux for 15 min. Cool the reaction to room temperature and concentrate to dryness under vacuum. Repeatedly dissolve the residue in toluene (2×100 mL) and concentrate to dryness to afford an off-white solid. Dissolve the solid in CH$_2$Cl$_2$ (100 mL) and add dropwise into a cold (0° C.) solution of phenol (3.7 g, 0.04 moles) in a mixture of CH$_2$Cl$_2$ (100 mL) and pyridine (15 mL). Stir at room temperature overnight and concentrate to a yellow oil. Redissolve in CH$_2$Cl$_2$ (100 mL), wash with aq. 1M HCl (2×50 mL), water (1×50 mL) and dry (MgSO$_4$). Remove the solvent by vacuum distilation to afford a light yellow solid (9.2 g). M.p. 39°–40° C. MS (Cl, M+H$^+$) m/e 363.

Preparation 13

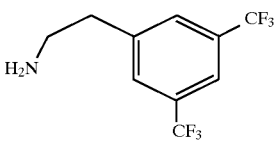

Treat a suspension of 3.5-bis(trifluoromethyl)phenyl acetic acid (5 g, 18 mmoles) in CH$_2$Cl$_2$ (100 mL) with oxallyl chloride (4.7 g, 3.3 mL, 37 mmoles) and a trace (3 drops) of DMF. Stir the mixture at room temp. under N$_2$ for 1 h and then heat to reflux for 1 h. Cool the mixture and remove the solvent in vacuo. Dilute the residue (5.2 g) with toluene (20 mL) and concentrate under reduced pressure (3 times). Dilute a portion (2.9 g, 10 mmoles) of the crude residue with CH$_2$Cl$_2$ (10 mL) and add to a rapidly stirred biphasic mixture of water (30 mL), concentrated NH$_4$OH and CH$_2$Cl$_2$ (30 mL). Stir the mixture an additional 15 min to obtain a precipitate. Separate the organic phase, dilute with 10 mL of EtOAc to dissolve the precipitate and dry (MgSO$_4$). Remove the solvent by vacuum distilation and triturate the residue with Et$_2$O/hexane (30 mL, 4:1). Collect the solid (2.48 g) by vacuum filtration and dry under vacuum. Dissolve a portion of the solid (1.47 g, 5.4 mmoles) in THF (20 mL) and add solid LiAlH$_4$ (0.51 g, 50 mmole) in small portions. Heat the mixture to reflux for 3 h, cool and then treat with 20 mL of a mixture of CH$_3$OH and 2N NaOH (9:1). After rapidly stirring for 20 minutes, remove the precipatate by filtration through celite. Dilute the organic phase with EtOAc (25 mL) and extract with 1N HCl (30mL). Basify the aqueous phase with 3N NaOH and extract with CH$_2$Cl$_2$ (2×30 mL). Dry the organic phase (MgSO$_4$) and concentrate under vacuum to give 0.22 g of the title compound. Concentrate the EtOAc layer from above under vacuum to a reddish oil and triturate with Et$_2$O to obtain an additional 0.11 gms of the title compound as the HCl salt. MS(Cl, M+H$^+$), m/e 258.

EXAMPLE 1

1-(3.5-bis(trifluoromethyl)phenyl[methoxy]-3-(3.4-dichlorophenyl)-5-(4-hydroxy-4-phenyl-1-piperidinyl)-2-pentanone O-methyloxime

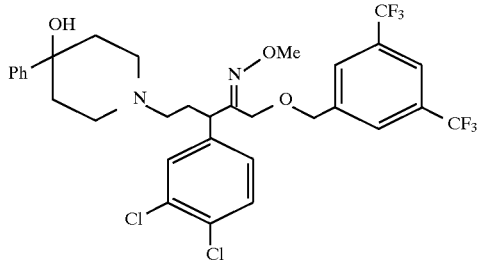

Treat a solution of the product of Preparation 4 (270 mg, 0.417 mmol) in dry pyridine (5 mL) with O-methoxylamine HCl (52 mg, 0.626 mmol, 1.5 eq) and heat to 60° C. for 30 min. Allow the vessel to cool to 23° C. and remove the pyridine in vacuo. Take up the crude product in a minimal amount of $CH_2Cl_2$ (2 mL) and apply to a silica gel column (2.5 cm×15 cm) packed with hexane:EtOAc:triethylamine (66:33:1). Elute with the same solvent system to obtain 190 mg (0.281 mmol, 67%) of the title compound as a colorless foam.

HRMS (FAB, M+H$^+$): m/e calc'd for $[C_{32}H_{33}N_2O_3Cl_2F_6]^+$: 677.1772, found 677.1785.

Examples 1 A to 1 F are prepared from the product of Preparation 4 in a procedure similar to that described for Example 1:

EXAMPLE 2

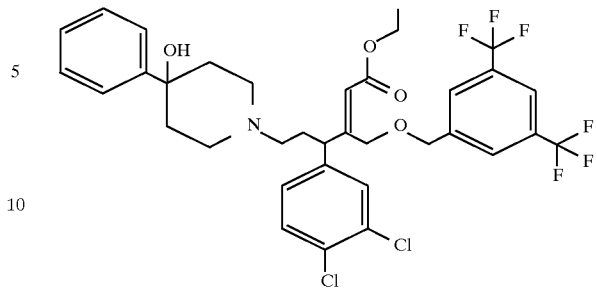

Treat a solution of triethyl phosphonoacetate (18 μL, 0.11 mmol, 1.1 eq) in dry THF (1.5 mL) at 0° C. with [(CH$_3$)$_3$Si]$_2$NNa (110 gL of .1M THF, 0.11 mmol, 1.1 eq). Stir for 30 min at 0° C. and add a solution of the ketone from Preparation 4 in dry THF (1.5 mL), using THF (0.5 mL) for quantitative transfer. Allow the reaction to warm to 23° C. and stir for 24 h. Quench the mixture with water and extract with $CH_2Cl_2$ (3×25 mL). Wash the combined organic layers with 5% aqueous NaOH, dry (Na$_2$SO$_4$) and concentrate to give the crude product as on oil. Purify by preparative TLC (0.5 mm silica gel; eluant: $CH_2Cl_2/CH_3OH$ (saturated with ammonia) (95:5) to obtain 41 mg (.057 mmol, 57%) of the title compound as a film.

HRMS (FAB, M+H$^+$): m/e calc'd for $[C_{35}H_{36}NO_4F_6Cl_2]^+$: 718.1926, found 718.1915.

EXAMPLES 3–4

Resolve the racemic compound of Example 1 A by HPLC using a Daicel Chiralcel AD chiral chromatography column

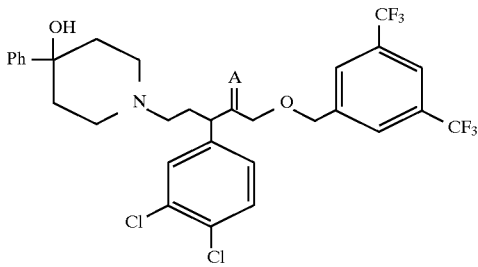

| Ex. | A | Starting Material | HRMS (FAB, M + H$^+$) calc'd | HRMS Found |
|---|---|---|---|---|
| 1A | =N—OH (Z isomer) | hydroxyl amine.HCl | 663.1616 | 663.1625 |
| 1B | HO—N= (E isomer) | hydroxyl amine.HCl | 663.1616 | 663.1631 |
| 1C | =N—OCH$_2$Ph | O-benzyl-hydroxyl amine.HCl | 753.2085 | 753.2069 |
| 1D | =N—OCH$_2$CH$_3$ | O-ethyl-hydroxyl amine.HCl | 691.1929 | 691.1922 |
| 1E | =N—OCH$_2$CH=CH$_2$ | O-allyl-hydroxyl amine.HCl | 703.1929 | 703.1946 |
| 1F | =N—OC(CH$_3$)$_3$ | O-t-butyl-hydroxyl amine.HCl | 719.2242 | 719.2252 |
| 1G | =N—OCH$_2$COOH | H$_2$NOCH$_2$CO$_2$H.HCl | | 721 (M + 1) |
| 1H | =N—O(CH$_2$)$_2$COOH | H$_2$NO(CH$_2$)$_2$—CO$_2$H.HCl | 735.1827 | 735.1807 |

(2.0 cm.×50.0 cm., 13% isopropanol in hexane). Four injections of 100 mg each provide:

Example 3, the (+) isomer:

150 mg; $t_R$=10 min.; $[\alpha]^{25}D$=+6.5°,(c=0.01, CHCl$_3$)

Example 3A, the (−) isomer:

140 mg; $t_R$=17 min.; $[\alpha]^{25}D$=−9.5°, (c=0.01, CHCl$_3$).

In a similar manner, resolve the compound of Example 1 B to obtain Examples 4 and 4A:

Enantiomer A: $t_R$=21 min.; HRMS (FAB, M+H$^+$): m/e calc'd for [C$_{31}$H$_{31}$N$_2$O$_3$F$_6$Cl$_2$]$^+$: 663.1616, found 663.1601;

Enantiomer B: $t_R$=31 min.; HRMS (FAB, M+H$^+$): m/e calc'd for [C$_{31}$H$_{31}$N$_2$O$_3$F$_6$Cl$_2$]$^+$: 663.1616, found 663.1621.

Prepare examples 5–6 from the products of Example 3 and 3A, respectively, in a manner similar to that described in Example 8, using CH$_3$I as the alkyl halide and DMF as the solvent.

EXAMPLE 5

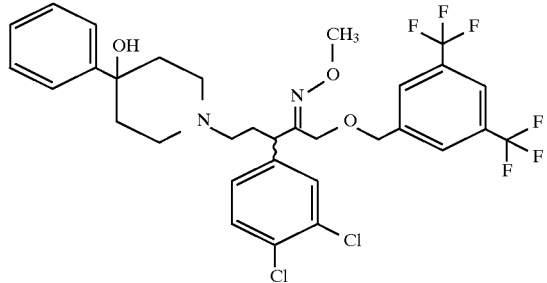

HRMS (FAB, M+H$^+$): m/e calc'd for [C$_{32}$H$_{33}$N$_2$O$_3$F$_6$Cl$_2$]$^+$: 677.1772, found 677.1769.

EXAMPLE 6

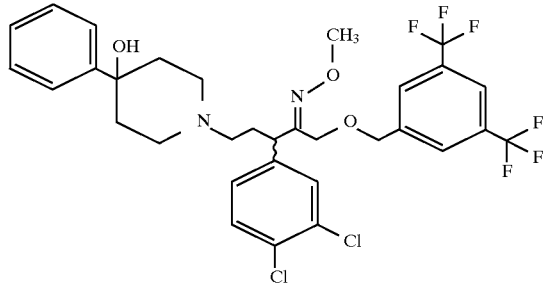

HRMS (FAB, M+H$^+$): m/e calc'd for [C$_{32}$H$_{33}$N$_2$O$_3$F$_6$Cl$_2$]$^+$: 677.1772, found 677.1762.

EXAMPLE 7

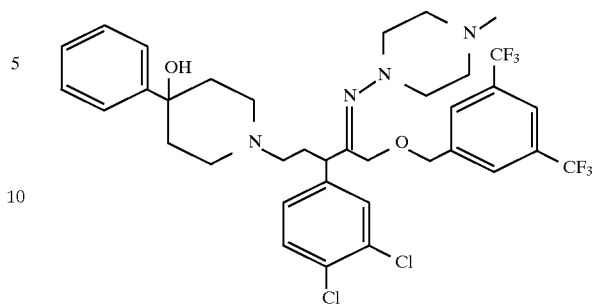

Treat a solution of the ketone of Preparation 4 (100 mg, 0.154 mmol) in ethanol (3 mL) with acetic acid (3 drops) followed by 1-amino-4-methyl-piperizine. Stir the mixture at 60° C. for 1 h, concentrate and triturate with water using sonication. Filter the resulting colorless solid and wash with water (3 mL) to give 86 mg (0.115 mmol, 75%) of the product as a colorless solid, mp 48°–49° C.

HRMS (FAB, M+H$^+$): m/e calc'd for [C$_{36}$H$_{40}$N$_4$O$_2$Cl$_2$F$_6$]$^+$: 745.2511, found 745.2502.

Using a similar procedure but substituting 4-aminomorpholine, dimethylhydrazine and 4-amino-i-piperazineethanolfor 1-amino-4-methyl-piperizine, obtain compounds 7A, 7B and 7C, respectively, as E/Z mixtures:

| Ex. | —N(R$^2$)(R$^3$) | HRMS calc'd (FAB, M + H$^+$) | HRMS Found |
|---|---|---|---|
| 7A | —N⟨O⟩ | 732.2194 | 732.2184 |
| 7B | —N(CH$_3$)$_2$ | 690.2089 | 690.2100 |
| 7C | —N⟨N—(CH$_2$)$_2$—OH⟩ | 775.2616 | 775.2641 |

EXAMPLE 8

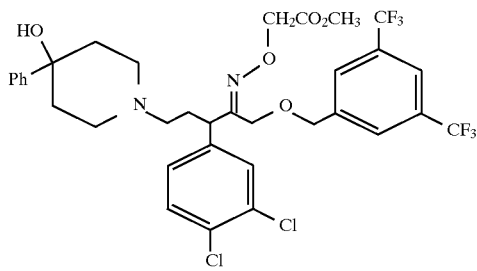

Treat a solution of Example 1A (400 mg, 0.603 mmol) in dry DMF (12 mL) at 0° C. with 60% NaH in mineral oil (48 mg), stir for 40 min and treat with methyl bromoacetate (60 μL, 0.633 mmol, 1.05 eq). Stir for 30 min, pour into EtOAc (250 mL) /half saturated NaHCO$_3$ (200 mL) and extract. Wash the organic layer with water (2×100 mL), then brine (10 mL) and dry over Na$_2$SO$_4$. Purify the crude mixture by silica gel chromatography (4×15 cm; hex/EtOAc 1:1 w/2% NEt$_3$) to give 361.8 mg (0.492 mmol, 82%) of the pure product as an oil.

HRMS (FAB, M+H$^+$): m/e calc'd for $[C_{34}H_{34}Cl_2F_6N_2O_5]^+$: 735.1827, found 735.1839.

Using a similar procedure, treat the product of Example 1A with the appropriate alkyl halide to obtain the following compounds 8A-8L:

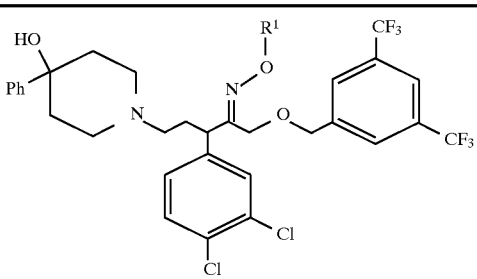

| Ex. | R$^1$ | Alkyl Halide | HRMS calc'd (FAB, M + H$^+$) | HRMS Found |
|---|---|---|---|---|
| 8A | —CH$_2$CH$_2$CO$_2$CH$_3$ | Me 3-Br-propionate | 749.1956 | 749.1984 |
| 8B | —CH$_2$CN | Br-acetonitrile | 702.1725 | 702.1720 |
| 8C | —CH$_2$(CH$_2$)$_2$CO$_2$CH$_3$ | Me 4-Br-butyrate | 763.2140 | 763.2143 |
| 8D | —CH$_2$(CH$_2$)$_3$CO$_2$CH$_3$ | Me 5-Br-valerate | 777.2297 | 777.2304 |
| 8E | —CH$_2$CH$_2$OH | 2-Br-1-(t-Bu-diMe-silyloxy)-ethane* | 707.1878 | 707.1856 |
| 8F | —CH$_2$CH$_2$OCH$_3$ | 2-Br-ethyl Me ether | 721.2035 | 721.2029 |
| 8G | —CH$_2$CH$_2$CH$_2$-Phthalyl | N-(3-Br-propyl)-phthalimide | 850.2249 | 850.2248 |
| 8H | —CH$_2$CH(OH)CH$_2$OH | (+/−)-3-Br,1,2-bis-(t-Bu-diMe-silyl-oxy)-propane* | 737.1984 | 737.1982 |
| 8I | —CH$_2$OCH$_3$ | Br-methyl Me ether | 707.1878 | 707.1855 |
| 8J | —CH$_2$OCH$_2$CH$_2$OCH$_3$ | 2-methoxy-ethoxy-Me Cl | 751.2140 | 751.2159 |
| 8K |  | epibromohydrin | 719.1878 | 719.1881 |

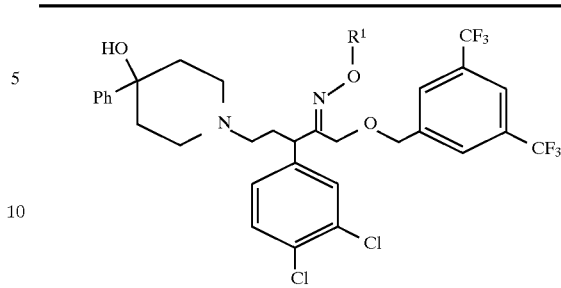

| Ex. | R$^1$ | Alkyl Halide | HRMS calc'd (FAB, M + H$^+$) | HRMS Found |
|---|---|---|---|---|
| 8L | H | 4-(3-Cl-propyl)-1-trityl-imidazole** | 771.2303 | 771.2305 |

*Followed by desilylation with 1M TBAF in THF (3 h, 23° C.).

**Followed by deprotection of the trityl group by stirring in PPTS/MeOH for 3 h at 60° C.

EXAMPLE 9

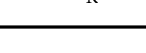

Treat a solution of the product of Example 8 (57 mg, 0.078 mmol) in MeOH (3mL) at 0° C. with gaseous ammonia for 5 min. After venting 2–3 times, seal the vessel with a polypropylene cap and stir until TLC shows the reaction is complete (20 h) to give (56 mg, 0.078 mmol, >99%) of the pure product as a colorless powder.

HRMS (FAB, M+H$^+$): m/e calc'd for $[C_{33}H_{33}Cl_2F_6N_3O_4]^+$: 720.1831, found 720.1841.

Using a similar procedure, treat the product of Example 8 with the appropriate amine to obtain the following compounds 9A, 9B and 9E; treat the product of Example 8A to obtain 9C and 9D; and treat the products of Examples 8C and 8D to obtain 9F and 9G, respectively:

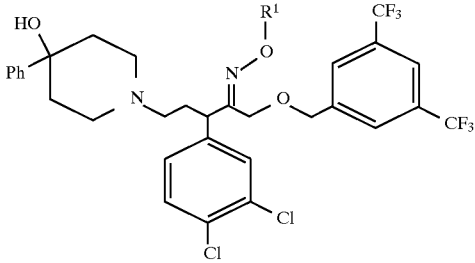

| Ex. | R¹ | Amine | HRMS calc'd (FAB, M + H⁺) | HRMS Found |
|---|---|---|---|---|
| 9A | —CH$_2$CONHCH$_3$ | CH$_3$NH$_2$ | 734.1987 | 734.2008 |
| 9B | —CH$_2$CON(CH$_3$)$_2$ | (CH$_3$)$_2$NH | 748.2144 | 748.2123 |
| 9C | —CH$_2$CH$_2$CONH$_2$ | ammonia | 734.1987 | 734.1976 |
| 9D | —CH$_2$CH$_2$CONHCH$_3$ | CH$_3$NH$_2$ | 748.2144 | 748.2124 |
| 9E | —CH$_2$CONHOH | H$_2$NOH in MeOH | 736.1780 | 736.1767 |
| 9F | —CH$_2$CH$_2$CH$_2$CONH$_2$ | ammonia | 748.2144 | 748.2169 |
| 9G | —CH$_2$(CH$_2$)$_3$CONH$_2$ | ammonia | 762.2300 | 762.2303 |

EXAMPLES 10 to 18

Using the procedures described below, compounds of the following structural formula were prepared, wherein the definitions of R¹ are shown in the table below:

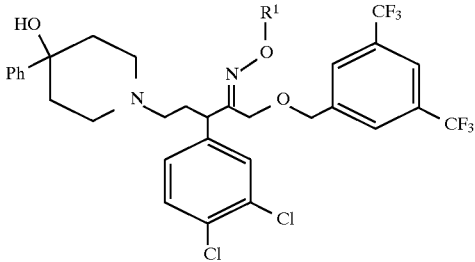

| Ex. | R¹ | HRMS calc'd (FAB, M + H⁺) | HRMS Found |
|---|---|---|---|
| 10 | —OCONHCH$_3$ | 720.1831 | 720.1820 |
| 11 | 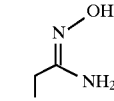 | 735.1940 | 735.1956 |
| 12 | 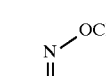 | 749.2096 | 749.2109 |
| 13 | 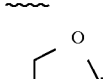 | 763.1776 | 763.1799 |

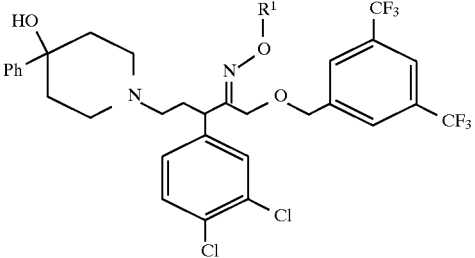

| Ex. | R¹ | HRMS calc'd (FAB, M + H⁺) | HRMS Found |
|---|---|---|---|
| 14 | 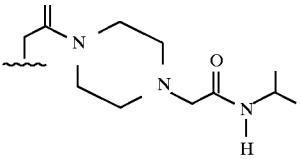 | 888.3093 | 888.3090 |
| 15 | 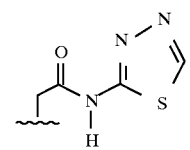 | 804.1613 | 804.1598 |
| 16 | 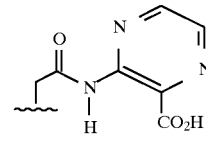 | 842.1947 | 842.1965 |
| 17 | 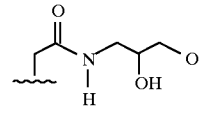 | 794.2198 | 794.2195 |
| 18 | 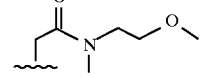 | 778.2249 | 778.2251 |

EXAMPLE 10

Treat a solution of the product of Example 1 (100 mg, 0.151 mmol) in CH$_2$Cl$_2$ (1 mL) with CH$_3$NCO (9 μL, 0.151 mmol, 1 eq) and pyridine (18 μL, 0.227 mmol, 1.5 eq) and stir for 60 hr. Concentrate in vacuo and purify by silica gel chromatography (2.5×18 cm; EtOAc/Hex 2:1 w/2% NEt$_3$) to give 88 mg (0.122, mmol 81%) of the pure product as a film.

EXAMPLE 11

Treat a suspension of H$_2$NOH.HCl (47 mg, 0.68 mmol, 5 eq) in ethanol with KOH in MeOH (680 μL, 0.68 mmol, 5 eq), sonicate for 5 min and then add to a solution of Example 8B (95 mg, 0.135 mmol) in ethanol (5 mL). Heat for 2.5 h at 60° C., filter, concentrate in vacuo and purify by silica gel chromatography (2.5×14 cm; CH$_2$Cl$_2$/MeOH (NH$_3$) 95:5) to give 98.3 mg (0.134 mmol, 99%) of the product as a film.

EXAMPLE 12

Use a procedure similar to that described in Example 11 using the product of Example 8B as the starting material, $H_2NOCH_3 \cdot HCl$ as the alkoxyl amine and 2,2,2-trifluoroethanol as the solvent.

EXAMPLE 13

Treat a solution of Example 8H (50 mg, 0.068 mmol) in 1,2 dichloroethane (1 mL) with carbonyidiimidazole (60 mg, 0.38 mmol, 5 eq), stir for 10 hr at reflux, and concentrate in vacuo. Purify by silica gel chromatography (1.5×121 cm; $CH_2Cl_2/MeOH$ ($NH_3$) 98:2) to give 40 mg (0.052mmol, 77%) as a film.

EXAMPLE 14

Treat a solution of Example 1G (100 mg, 0.139 mmol) in THF (2 mL) and N-isopropyl-1-piperazine-acetamide (77 mg, 0.417 mmol, 3 eq) with $Et_3N$ (29 μL, 0.209 mmol, 1.5 eq) and DEC (40 mg, 0.209 mmol, 1.5 eq), stir until complete by TLC (72 hr), and partition between EtOAc (50 mL) /10% citric acid (20 mL). Wash with water (25 mL), sat'd $NaHCO_3$ (25 mL), brine (10 mL), and dry over $Na_2SO_4$. Purify by silica gel chromatography (2.5×10 cm; $CH_2Cl_2/MeOH$ ($NH_3$) 9:1) to give 36.2 mg (0.041 mmol, 29%) of the desired product as a foam.

EXAMPLE 15

In a similar fashion to Example 14, use 2-amino-1,3,4-thiadiazole as the amine to obtain the desired product.

EXAMPLE 16

In a similar fashion to Example 14, use 3-aminopyrazine-2-carboxylic acid as the amine to obtain the desired product.

EXAMPLE 17

In a similar fashion to Example 14, use (+/−)-3-amino-1,2-propanediol as the amine to obtain the desired product.

EXAMPLE 18

In a similar fashion to Example 14, use 2-methoxyethyl amine as the amine to obtain the desired product.

Examples 19, 19A and 19B

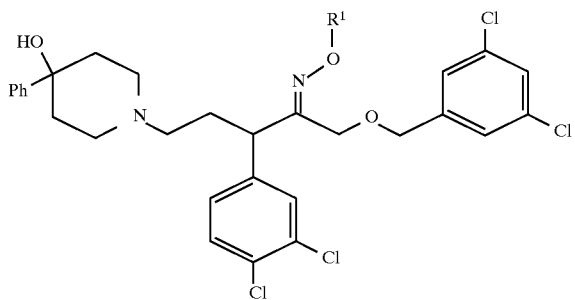

Using the procedures described below, compounds of the structural formula above were prepared, wherein the definitions of $R^1$ are shown in the following table:

| Ex. | $R^1$ | HRMS calc'd (FAB M + H⁺) | HRMS Found |
|---|---|---|---|
| 19 | —$CH_2CN$ | 634.1198 | 634.1206 |
| 19A | —$CH_2CH_2OH$ | 639.1351 | 639.1342 |
| 19B | ![structure with N-OH and NH2] | 667.1351 | 639.1342 |

EXAMPLE 19

Step 1: Prepare the allyl oxime ether of the product of Example 22, Step 2, using a procedure similar to that used in Example 1, employing 0 allylhydroxylamine HCl as the alkoxyl amine.

Step 2: Deprotect the silyl protective group in a procedure similar to that describe in Example 22, Step 4.

Step 3: Alkylate the hydroxyl group with 3,5-dichlorobenzylbromide in a procedure similar to that in Example 22.

Step 4: Treat a solution of the product of step 3 (285 mg, 0.426 mmol) in 80% aqueous EtOH with $Pd(PPh_3)_4$ (25 mg, 0.021 mmol, 0.05 eq) and triethylammoniumformate (2.13 mL of IM solution in THF, 5 eq) and stir at reflux for 4 h. Cool, concentrate and purify by silica gel chromatography (2.5×16.5 cm; hex/EtOAc 1:1 w/2% $NEt_3$) to give 185 mg (0.3095 mmol, 73%) as a film.

Step 5: Treat the product of step 4 in a similar fashion to Example 8, using $BrCH_2CN$ as the alkyl halide.

EXAMPLE 19A

Treat the product of Example 19, step 4, in a similar fashion to Example 8, using 2-bromo-1-(tbutyldimethylsiloxy)ethane as the alkyl halide, followed by desilylation (3 h, 23° C.) with 1M TBAF in THF.

EXAMPLE 19B

Treat the product of Example 19 in a similar fashion to Example 11 to obtain the desired product.

EXAMPLES 20, 20A, 20B, 20C and 20D

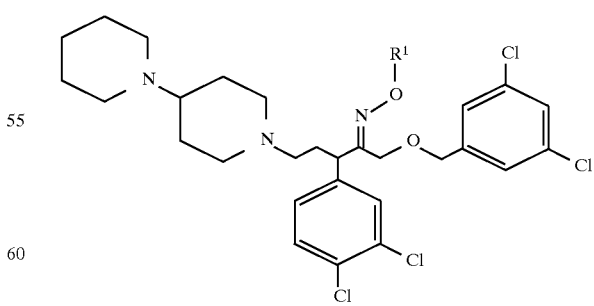

Using the procedures described below, compounds of the structural formula above were prepared, wherein the definitions of $R^1$ are shown in the following table:

| Ex. | R¹ | HRMS calc'd (FAB, M + H⁺) | HRMS Found |
|---|---|---|---|
| 20 | —H | 586.1562 | 586.1582 |
| 20A | —CH₂CN | | 627 (M + 1) |
| 20B | ![N-OH, NH2 group] | 658.1885 | 658.1873 |
| 20C | —CH₂CH₂OH | 630.1824 | 630.1816 |
| 20D | —CH₃ | 600.1718 | 600.1722 |

| Ex. | R¹ | HRMS calc'd (FAB, M + H⁺) | HRMS Found |
|---|---|---|---|
| 21 | —CH₃ | 631.1620 | 631.1599 |
| 21A | —CH₂CH₂OH | 659.1725 | 659.1708 |
| 21B | —CH₂CN | 654.1572 | 654.1563 |
| 21C | ![N-OH, NH2 group] | 687.1787 | 687.1797 |

EXAMPLE 20

Using a procedure similar to Example 47, substitute 3,5 dichlorobenzyl alcohol for 3,6 bistrifluorobenzyl alcohol in step 1; proceed in a similar manner through steps 2, 3, and 4, using allylhydroxylamine HCl as the alkoxyl amine in step 4. Proceed in a similar fashion through steps 5 and 6, using piperidinopiperidine in place of 4-phenyl-4-piperidinyl acetamide. Treat the resultant product using a procedure similar to Example 19, step 4, to obtain the desired compound.

EXAMPLE 20A

Treat the product of Example 20 in a similar fashion to Example 8, using BrCH₂CN as the alkyl halide to obtain the desired product.

EXAMPLE 20B

Treat the product of Example 20A in a similar fashion to Example 11 to obtain the desired product.

EXAMPLE 20C

Treat the product of Example 20 in a similar fashion to Example 8 using 2-bromo-1-(t butyidimethylsiloxy)ethane as the alkyl halide, followed by desilylation (3 h, 23° C.) with 1M TBAF in THF to obtain the desired product.

EXAMPLE 20D

Treat the product of Example 20 in a similar fashion to Example 8 using CH₃I as the alkyl halide to obtain the desired product.

EXAMPLES 21, 21A, 21B and 21C

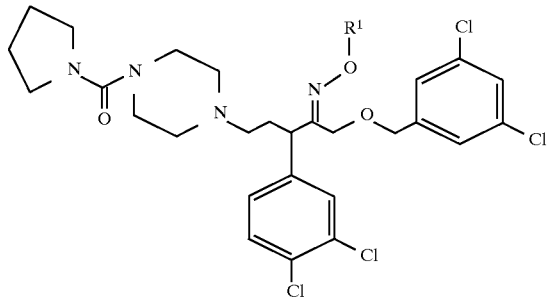

Using the procedures described below, compounds of the structural formula above were prepared, wherein the definitions of R¹ are shown in the following table:

EXAMPLE 21

Step 1: Prepare the oxime precusor using a procedure similar Example 20, using 1-(pyrrolidinocarbonylmethyl) piperizine in place of piperidinopiperidine.

Step 2: Treat the product of step 1, in a similar fashion to Example 8, using CH₃I as the alkyl halide to obtain the desired product.

EXAMPLE 21A

Treat the product of Example 21, step 1, in a similar fashion to Example 8, using 2-bromo-1-(tbutyidimethylsiloxy)ethane as the alkyl halide, followed by desilylation (3 h, 23° C.) with 1M TBAF in THF to obtain the desired product.

EXAMPLE 21B

Treat the product of Example 21, step 1, in a similar fashion to Example 8, using BrCH₂CN as the alkyl halide to obtain the desired product.

EXAMPLE 21C

Treat Example 21B in a similar fashion to Example 11 to obtain the desired product.

EXAMPLE 22

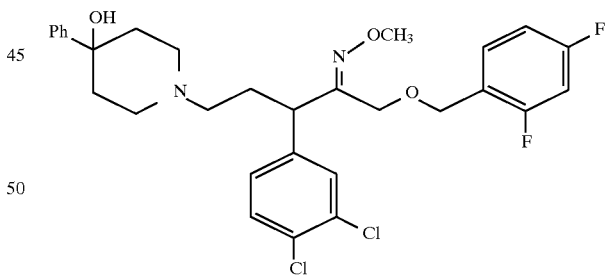

Step 1: β-(3,4-dichlorophenyl)-α-[[[dimethyl(1,1-dimethylethyl)silyl]oxy]-methyl]-4-hydroxy-4-phenyl-1-piperidinebutanol Treat a solution of the diol from Preparation 3 (1 9.8g, 46.6 mmol), Et₃N (13 mL, 93.2 mmol) and dimethylaminopyridine (564 mg, 4.66 mmol) in CH₂Cl₂ (300 mL)with TBSCI (8.44 g, 55.9 mmol) at 0° C. Allow the resulting solution to warm to room temperature and stir for 12–18 hours. Quench the reaction with water and extract with CH₂Cl₂ (3×200 mL), combine the organic layers, dry over MgSO₄, filter and concentrate under reduced pressure to give the crude product. Purify by silica gel chromatography (column: 10 cm×24 cm; pack column in $CH_2Cl_2$ and elute using a gradient of 100% $CH_2Cl_2$ to 10% $CH_3OH/CH_2Cl_2$) to obtain 21.5 g (39.8 mmol, 85%) of the title compound as a tan foam.

Step 2: 3-(3,4-dichlorophenyl)-1-[[dimethyl(1,1-dimethylethyl)silyl]oxy]-5-(4-hydroxy-4-phenyl-1-piperidinyl)-2-pentanone Treat a solution of the alcohol from Step 1 (21.5 g, 39.8 mmol) in $CH_2Cl_2$ (600 mL) with PDC (22.5 g, 59.9 mmol). Stir the resulting black mixture for 12 h. Filter the reaction mixture through a plug of celite and wash plug with $CH_2Cl_2$ (200 mL) and EtOAc (200 mL). Concentrate the filtrate under reduced pressure to give the crude product as a black oil. Purify by silica gel chromatography (column: 10 cm ×24 cm; pack column in $CH_2Cl_2$ and elute using a gradient of 100% $CH_2Cl_2$ to 5% $CH_3OH(NH_3)/CH_2Cl_2$) to obtain 16 g (29.9 mmol, 75%) of the title compound as a tan foam.

Step 3: 3-(3,4-dichlorophenyl)-1-[[dimethyl(1,1-dimethylethyl)silyl]oxy]-5-(4-hydroxy-4-phenyl-1-piperidinyl)-2-pentanone O-methyloxime Treat a solution of the ketone from Step 2 (6.6 g, 12.3 mmol) and NaOAc (6.05 g, 73.8 mmol) in EtOH (110 mL) and $H_2O$ (27 mL) with $NH_2OCH_3·HCl$. Stir the resulting solution for 12–18 hours at room temperature. Concentrate under reduced pressure and partition the resulting residue between $CH_2Cl_2$ (100 mL) and $H_2O$ (100 mL). Extract the aqueous layer with $CH_2Cl_2$ (3×100 mL), dry the combined organic layers over $MgSO_4$, filter and concentrate under reduced pressure to yield the crude product as a pale oil. This product is carried on without purification to the next step. HRMS (FAB, M+H$^+$): m/e cal'd for $[C_{29}H_{43}N_2O_3SiCl_2]^+$: 565.2420, found 565.2410.

Step 4: 3-(3,4-dichlorophenyl)-1-hydroxy-5-(4-hydroxy-4-phenyl-1-piperidinyl)-2-pentanone O-methyloxime Treat a solution of the crude oxime from Step 3 ($\leq$12.3 mmol) in THF (400 mL) with TBAF (15.4 mL, 15.4 mmol, 1M in THF) at 0° C. Stir the solution for 2 hours. Quench the reaction with water and extract the aqueous phase with EtOAc (3×100 mL). Dry the combined organic layers over $MgSO_4$, filter and concentrate under reduced pressure to give the crude product as a yellow oil. Purify by silica gel chromatography (column: 7.5 cm×20 cm; pack column in $CH_2Cl_2$ and elute using a gradient of 100% $CH_2Cl_2$ to 5% $CH_3OH(NH_3)/CH_2Cl_2$) to obtain 16 g (29.9 mmol, 75% from Example CAA2) of the title compound as a white solid. HRMS (FAB, M+H$^+$): m/e cal'd for $[C_{23}H_{29}N_2O_3Cl_2]^+$: 451.1555, found 451.1553.

Step 5: 3-(3,4-dichlorophenyl)-1-[(2,4-difluorophenyl)methoxy]-5-(4-hydroxy-4-phenyl-1-piperidinyl)-2-pentanone O-methyloxime Treat a solution of the hydroxy-oxime (200 mg, 0.44 mmol) of Step 4 in DMF at 0° C. with NaH (12 mg, 0.48 mmol). Stir the resulting mixture for 30 mins at 0° C. Add 2,4-difluorobenzylbromide (60 µL, 0.465 mmol) in one portion and remove cooling bath. Stir the reaction for 12–18 hours at room temperature. Quench the reaction with $H_2O$ and extract with EtOAC (3×30 mL). Dry the combined organic layers over $MgSO_4$, filter and concentrate under reduced pressure to give the crude compound as a yellow oil. Purify by silica gel chromatography (column: 2.5 cm×15 cm; pack column in 50% EtOAc/Hexane and elute using a gradient of 50–100% EtOAc/Hexane) to obtain 128 mg (0.22 mmol, 50%) of the title compound as a pale oil. HRMS (FAB, M+H$^+$): m/e cal'd for $[C_{30}H_{33}N_2O_3Cl_2F_2]^+$: 577.1836, found 577.1832.

Examples 22A to 22AL, shown in the following table, are prepared from the product of Example 22, Step 4 in a procedure similar to that described for Example 22, Step 5, using the appropriate halide:

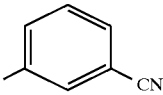

| Ex. | T | Starting Material | HRMS calc'd (FAB, M + H$^+$) | HRMS Found |
|---|---|---|---|---|
| 22A | 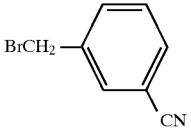 | 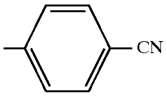 | 566.1977 | 566.1982 |
| 22B | 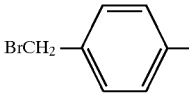 | 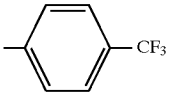 | 566.1977 | 566.1976 |
| 22C | 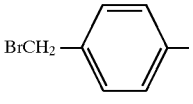 | BrCH$_2$-⟨⟩-CF$_3$ | 609.1899 | 609.1886 |

| | | | | |
|---|---|---|---|---|
| 22D | 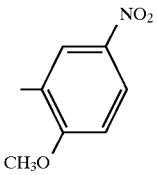 | 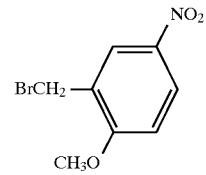 | 616.1981 | 616.1984 |
| 22E | 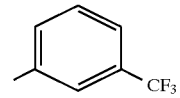 | 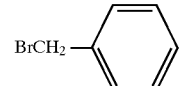 | 609.1899 | 609.1906 |
| 22F | 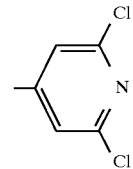 | 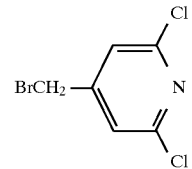 | 610.1198 | 610.1203 |
| 22G | 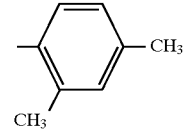 | 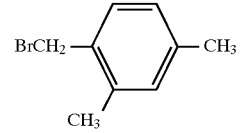 | 569.2338 | 569.2335 |
| 22H | 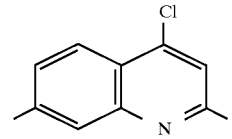 | 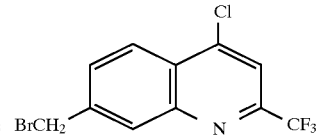 | 694.1618 | 694.1615 |
| 22I | 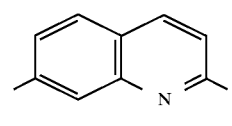 | 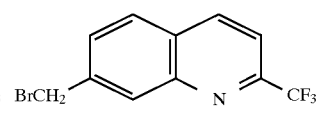 | 660.2008 | 660.2005 |
| 22J | 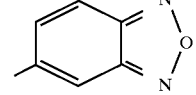 | 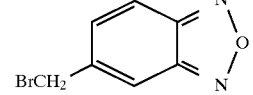 | 583.1879 | 583.1886 |
| 22K | 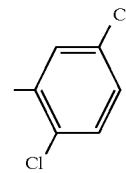 | 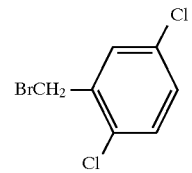 | 609.1253 | 609.1253 |
| 22L | 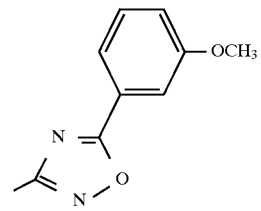 | 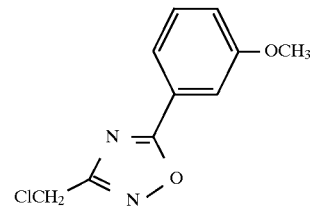 | 639.2141 | 639.2147 |
| 22M | 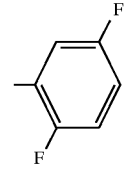 | 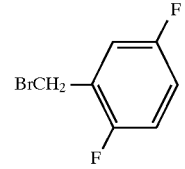 | 577.1836 | 577.1840 |

-continued
| | | | | |
|---|---|---|---|---|
| 22N | 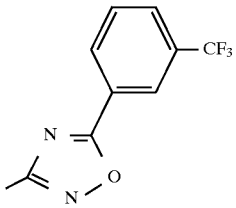 | 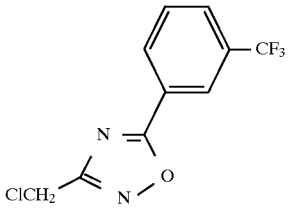 | 677.1909 | 677.1907 |
| 22O | 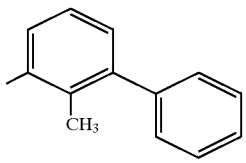 | 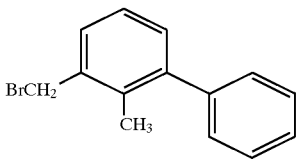 | 631.2494 | 631.2499 |
| 22P | 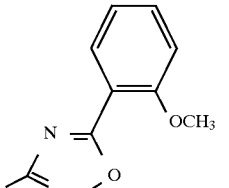 | 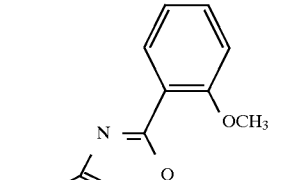 | 639.2141 | 639.2141 |
| 22Q | 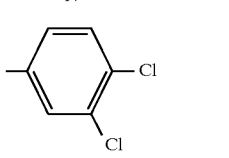 | 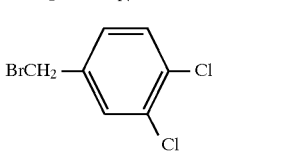 | 609.1245 | 609.1241 |
| 22R | 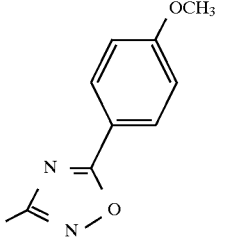 | 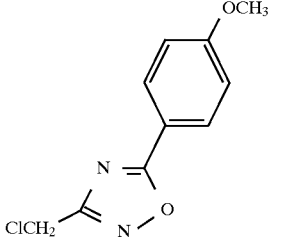 | 639.2141 | 639.2135 |
| 22S | 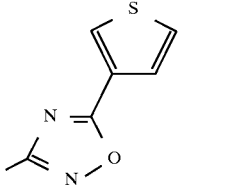 | 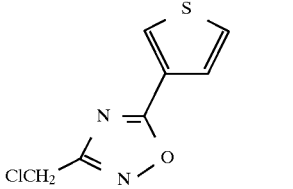 | 615.1600 | 615.1613 |
| 22T | 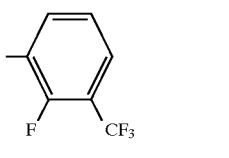 | 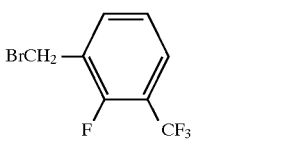 | 627.1804 | 627.1813 |
| 22U | 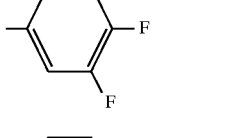 | 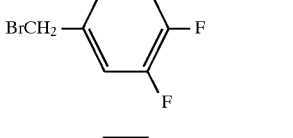 | 577.1836 | 577.1845 |
| 22V | 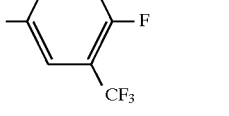 | 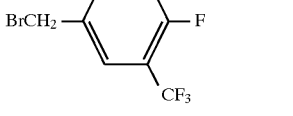 | 627.1804 | 627.1813 |

-continued
| Ex. | T | Starting Material | | |
|---|---|---|---|---|
| 22W | 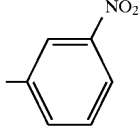 | 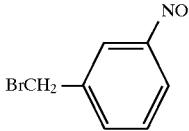 | 586.1876 | 586.1873 |
| 22X | 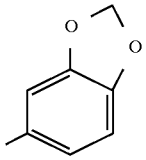 | 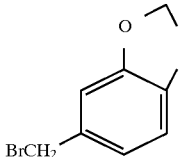 | 585.1923 | 585.1916 |
| 22AK | 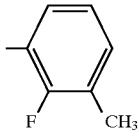 | 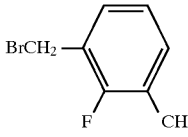 | 573.2087 | 673.2096 |
| 22AL | 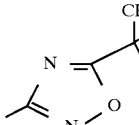 | 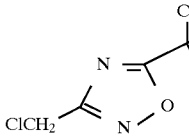 | 589.2348 | 589.2342 |
| Ex. | T | Starting Material | Analysis Calc'd | Analysis Found |
|---|---|---|---|---|
| 22Y |  | 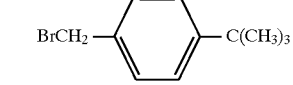 | C, 68.33; H, 7.08; N, 4.69 [$C_{34}H_{42}N_2O_3Cl_2$] | C, 67.99; H, 7.38; N, 4.79 |
| 22Z | 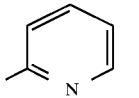 | 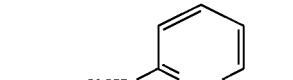 | C, 63.68; H, 6.17; N, 7.68 [$C_{29}H_{33}N_3O_3Cl_2 \cdot 0.25 H_2O$] | C, 63.54; H, 6.43; N, 7.68 |
| 22AA |  | 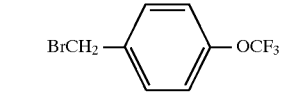 | C, 57.86; H, 5.48; N, 4.35 [$C_{31}H_{33}N_2O_4Cl_2F_3 \cdot H_2O$] | C, 58.16; H, 5.43; N, 4.45 |
| 22AB | 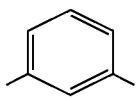 | 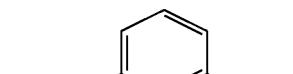 | C, 64.18; H, 6.85; N, 4.54 [$C_{33}H_{40}N_2O_4Cl_2 \cdot H_2O$] | C, 64.03; H, 7.06; N, 4.77 |
| 22AC | 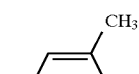 | 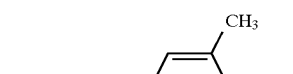 | C, 62.12; H, 6.29; N, 4.42 [$C_{32}H_{38}N_2O_3Cl_2 \cdot 0.75 CH_2Cl_2$] | C, 62.37; H, 6.85; N, 4.53 |
| 22AD |  |  | C, 60.28; H, 6.01; N, 8.79 [$C_{32}H_{35}N_4O_4Cl_2 \cdot 1.5H_2O$] | C, 60.3; H, 6.02; N, 8.60 |

| | | | |
|---|---|---|---|
| 22AE | —⟨C₆H₄⟩—CO₂CH₃ | BrCH₂—⟨C₆H₄⟩—CO₂CH₃ | C, 60.47; H, 6.34; N, 4.41 [C₃₂H₃₆N₂O₅Cl₂·2H₂O] | C, 59.79; H, 6.34; N, 4.67 |
| 22AF | —⟨C₆H₄⟩—I | BrCH₂—⟨C₆H₄⟩—I | C, 51.89; H, 5.23; N, 4.03 [C₃₀H₃₃N₂O₃Cl₂I·1.5H₂O] | C, 51.73; H, 5.22; N, 3.98 |
| 22AG | —⟨C₆H₃(Br)(OCH₃)⟩ | BrCH₂—⟨C₆H₃(Br)(OCH₃)⟩ | C, 53.54; H, 5.80; N, 4.03 [C₃₁H₃₅N₂O₄BrCl₂·2.5H₂O] | C, 53.47; H, 5.49; N, 4.14 |

EXAMPLE 22AH

Using 2-acetoxy-1-bromo-1-phenylethane as the halide, prepare 1-(acetyloxy)-3-(3,4-dichlorophenyl)-5-(4-hydroxy-4-phenyl-1-piperidinyl)-2-pentanone O-methyloxime. HRMS (FAB, M+H⁺): m/e cal'd for $[C_{25}H_{31}N_2O_4Cl_2]^+$: 493.1661, found 493.1652.

EXAMPLE 22AI

Using a-methylbenzylbromide as the halide, prepare 3-(3,4-dichlorophenyl)-5-(4-hydroxy-4-phenyl-1-piperidinyl)-1-(1-phenylethoxy)-2-pentanone O-methyloxime. HRMS (FAB, M+H⁺): m/e cal'd for $[C_{21}H_{27}N_2O_3Cl_2]^+$: 555.2181, found 555.2181.

EXAMPLE 22AJ

Using cinnamoylbromide as the halide, prepare 3-(3,4-dichlorophenyl)-1-[3-phenyl-2-propenyloxy]-5-(4-hydroxy-4-phenyl-1-piperidinyl)-2-pentanone O-methyloxime. Mass spectrum (FAB): 567.

EXAMPLE 23

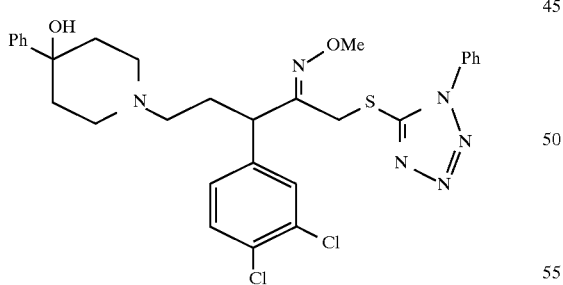

Treat the product of Example 22, Step 4 (0.203 g) in THF (5 mL) at 0° C. with 1-phenyl-5-mercaptotetrazole (0.16 9), stir for 30–40 min. and add this mixture to a solution of DEAD (142 μL) and Ph₃P (0.236 g) in THF (2.5 mL) also at 0° C. Stir the combined mixture for 30 min. and evaporate the solvent under reduced pressure. Purify the residue by silica gel chromatography eluting with mixtures of NH₃/MeOH/CH₂Cl₂ to give the title compound (0.038 g). Analysis: Calc'd for C₃₀H₃₂N₆O₆Cl₂S·H₂O; C, 57.23, H, 5.44, N, 13.25. Found: C, 57.70, H, 5.17, N, 12.91.

Using the product of Example 22, Step 4, as starting material in the procedure of Example 23, prepare Examples 23A and 23 B, using 4,6-dimethylpyrimidine-2-thiol and phthalimide, respectively:

EXAMPLE 23A

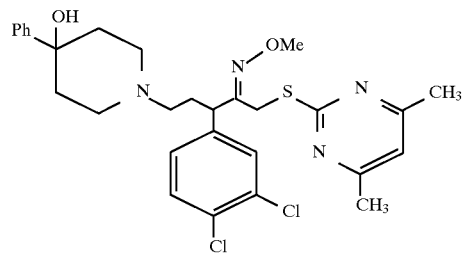

Example 23A: HRMS (FAB, M+H⁺): m/e calc'd for $[C_{29}H_{35}N_4O_2SCl_2]^+$: 573.1858, found 573.1845.

EXAMPLE 23B

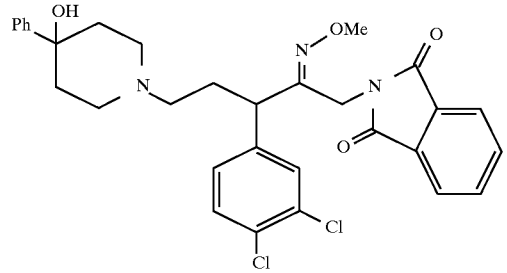

Example 23B: HRMS (FAB, M+H⁺): m/e calc'd for $[C_{31}H_{32}N_3O_4Cl_{22}]^+$: 580.1770, found 580.1771.

EXAMPLE 24

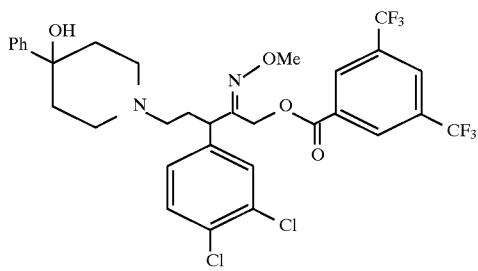

Treat the product of Example 22, Step 4 (0.18 g) with HOBT (54 mg) and 3,5-bis-trifluorobenzoic acid (0.13 g) in $CH_2Cl_2$ (40 mL) at 0° C. To this cooled mixture add DEC (76 mg) and stir for a further 18 h. Wash the solution with $H_2O$ (20 mL), dry the organic layer over $MgSO_4$, filter and evaporate give a foam. Purify the crude product by silica gel chromatography eluting with mixtures $NH_3$/MeOH/$CH_2Cl_2$ to give the title compound (0.18 g). Analysis: Calc'd for $C_{32}H_{30}N_2O_4Cl_2F_6 \cdot 1.5H_2O$; C, 53.49, H, 4.63, N, 3.90. Found: C, 53.39, H, 4.31,) N, 3.78.

EXAMPLE 25

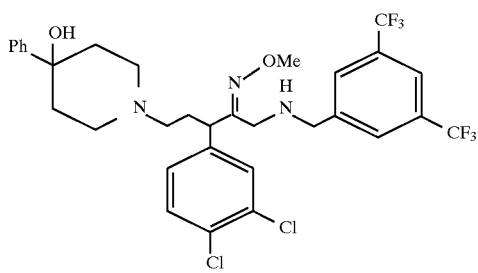

Step 1: Add the product of Example 22, Step 4 (1.8 g) and TFA (0.31 μL) to a iodoxybenzoic acid (2.24 g) in DMSO (20 mL). Stir the mixture for 2 h and add ice/$H_2O$ (50 mL), conc. $NH_4OH$ soln. (5 mL) and EtOAc (50 mL). Stir the mixture and filter to remove solids. Wash the solid residue with $H_2O$ (2×20 mL) and EtOAc (2×20 mL). Combine the filtrates, separate the organic layer and wash with $H_2O$ (2×25 mL), dry over $MgSO_4$, filter and evaporate to give 3-(3,4-dichlorophenyl)-5-(4-hydroxy-4-phenyl-1-piperidinyl)-2-(2-methoxyimino)pentanal (1.8 g) as a foamy solid. Mass spectrum (FAB): 449.

Step 2: Treat the product of Step 1 (0.2 g) in $CF_3CH_2OH$ (5 mL) with 3Å molecular sieves (1.0 g) and 3,5-bistrifluoromethylbenzylamine (0.14 g). Stir the mixture for 90 min. and add $NaBH_3CN$ (0.12 g). After 18 h. filter the reaction mixture through a pad of celite, rinse the celite with MeOH (10 mL) and evaporate the combined filtrates. Partition the residue between $CH_2Cl_2$ (15 mL) and 20% KOH (15 mL). Separate the organic layer and extract the aqueous layer with $CH_2Cl_2$ (2×20 mL). Combine the organic extracts, dry over $MgSO_4$, filter and evaporate to give a solid. Purify the crude by silica gel chromatography eluting with $NH_3$/MeOH/$CH_2Cl_2$ mixtures to give the title compound (0.1 g)

HRMS (FAB, M+H$^+$): m/e calc'd for $[C_{32}H_{34}N_3O_6Cl_2F_6]^+$: 676.1932, found 676,1 940.

EXAMPLE 25A 3-(3,4-Dichlorophenyl)-5-(4-hydroxy-4-phenyl-1-piperidinyl)-1-[[(2-methoxyphenyl)methyl]amino]-2-pentanone O-methyloxime.

Using the product of Example 25, Step 1 as starting material, prepare the compound of Example 25A using 2-methoxybenzylamine in a procedure similar to that described in Example 25, Step 2.

HRMS (FAB, M+H$^+$): m/e calc'd for $[C_{31}H_{37}N_3O_3Cl_2]^+$: 570.2290, found 570.2291

EXAMPLE 26

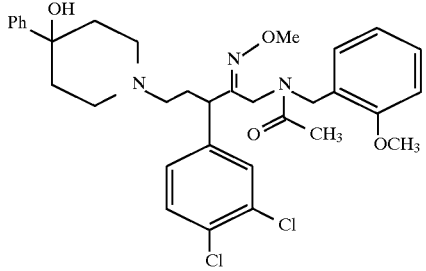

Treat the product of Example 25A (50 mg) in $CH_2Cl_2$ (5 mL) with HOBT (12.4 mg) and AcOH (1 mL) and cool to 0° C. To the cold solution, add DEC (17.6 mg) and stir for a further 18 h. Wash the reaction mixture with 10% $NH_4OH$ soln. (3 mL). Reextract the aqueous layer with $CH_2Cl_2$ (3×3 mL), combine the organic portions, dry over $MgSO_4$, filter and evaporate to give a solid. Purify the crude by silica gel chromatography eluting with $NH_3$/MeOH/$CH_2Cl_2$ mixtures to give the title compound (0.042 g).

Analysis: Calc'd for $C_{33}H_{39}N_3O_4Cl_2 \cdot 0.5H_2O$; C, 63.76, H, 6.49, N, 6.76. Found: C, 63.83, H, 6.85, N, 6.95.

EXAMPLE 27

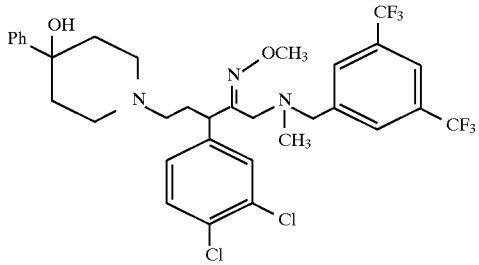

Treat the product obtained in Preparation 5A in a similar manner to the procedures described in Preparation 4 and Example 1 to obtain the desired product.

HRMS (FAB, M+H$^+$): m/e cal'd for $[C_{33}H_{36}N_3O_2Cl_2F_6]^+$: 690.2089, found 690.2085.

EXAMPLE 28

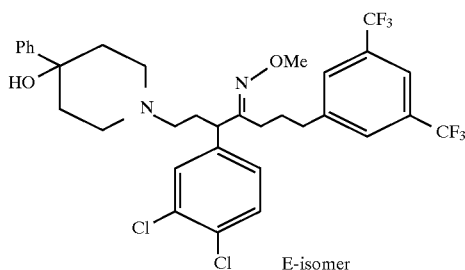

E-isomer

Dissolve the product of Preparation 9 in anhydrous CH₃OH, filter, add 0.82 g (4.6 mmol) of 4-phenyl-4-hydroxypiperidine and 1.1 g of MgSO₄, and stir 30 min at room temperature. Add NaCNBH3 (0.40 g, 6.38 mmol) and stir at room temperature under $N_2$ for 15 h. Filter and evaporate in vacuo. Partition the residue between $CH_2Cl_2$ (150 ml) and $H_2O$. Wash the organic layer with brine, dry ($MgSO_4$), filter and evaporate in vacuo (1.90 g). Purify by flash chromatography (50 g $SiO_2$; eluant:hexane:EtOAc (70:30)) to obtain 1.06 g (61.63%) of the crystalline hemihydrate of the title compound. M.p. 115°–118° C. FAB-Ms.: m/z 675 ($[C_{33}H_{34}{}^{35}Cl_2F_6N_2O_2+H]^+$, 100%). Maleate hemihydrate m.p.56°–60°.

Use the appropriate aldehyde from Preparation 9 and the appropriate amine in the procedure of Example 28 to obtain the compounds shown in the following table:

| Ex. | Z | b | T | Isomer | Physical Data |
|---|---|---|---|---|---|
| 28A | 4-hydroxy-4-phenylpiperidin-1-yl | 2 | 3,5-bis(CF₃)phenyl | Z | maleate.1/2 H₂O: m.p. 61–65° C. |
| 28B | 4-piperidin-1-yl-piperidin-1-yl | 2 | 3,5-bis(CF₃)phenyl | E | dimaleate: m.p.: 193–195.5° C. |
| 28C | 4-hydroxy-4-phenylpiperidin-1-yl | 1 | 3,5-bis(CF₃)phenyl | E | FAB-Ms: m/z 661 ($[C_{32}H_{32}{}^{35}Cl_2F_6N_2O_2 + H]^+$, 100%). |
| 28D | 4-piperidin-1-yl-piperidin-1-yl | 1 | 3,5-bis(CF₃)phenyl | E | maleate.1/2 H₂O: m.p.: 126–130° C. |
| 28E | 4-hydroxy-4-phenylpiperidin-1-yl | 1 | 3,4,5-tri(OCH₃)phenyl | E | maleate: m.p.: 153–156° C. |

-continued

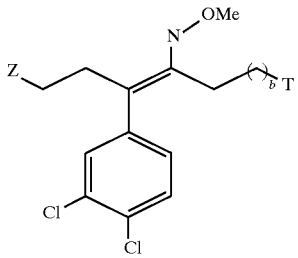

| Ex. | Z | b | T | Isomer | Physical Data |
|-----|---|---|---|--------|---------------|
| 28F | HO-[4-phenyl-piperidin-1-yl]- | 1 | 3,4,5-tri-OCH₃-phenyl | Z | maleate.H₂O: m.p. 70–73° C. |

EXAMPLE 29

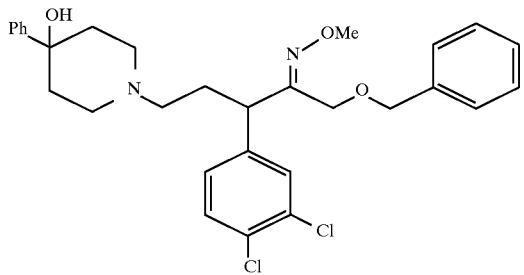

Step 1: Treat the product of Preparation 3 (0.469 g) in a solution of THF (1 mL) and DMF (1 mL) at 0° C. with NaH (50 mg), stir for 15 min., then add benzyl bromide (0.145 mL). Stir the resulting mixture for 18 h, evaporate the solvent under reduced pressure and partition the residue between CH₂Cl₂ (50 mL) and H₂O (50 mL). Separate the organic layer, wash with brine (50 mL) dry over MgSO4, filter and evaporate. Purify the product by silica gel chromatography eluting with $NH_3/MeOH/CH_2Cl_2$ mixtures to give α-[[phenylmethoxy]methyl]-β-(3,4-dichlorophenyl)-4-hydroxy-4-phenyl-1-piperidinol (0.2 g).

Step 2: Oxidize the product of Step 1 (0.1 g) according to the procedure of Preparation 4 to give 1-[[phenylmethoxy]methyl]-3-(3,4-dichlorophenyl)-5-(4-hydroxy-4-phenyl-1-piperidinyl)-2-pentanone (0.178 g).

Step 3: Treat the product of Step 2 (0.16 g) with O-methoxylamine HCl as in the procedure of Example 1 to obtain the title compound (0.14 g). HRMS (FAB, M+H⁺): m/e calc'd for $[C_{30}H_{35}N_2O_3Cl_2]^+$: 541.2025, found 541.2018

Using the product of Preparation 3 and the appropriate halide, prepare the compounds of Examples 29A to 29K, shown in the following tables, using a procedure similar to that described in Example 29:

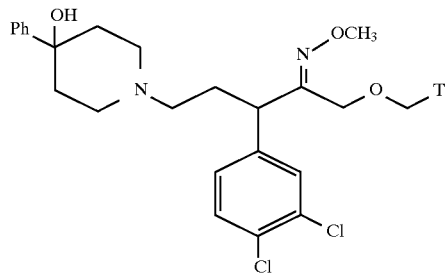

| Ex. | T | Starting Material | HRMS calc'd (FAB, M + H⁺) | HRMS Found |
|-----|---|-------------------|---------------------------|------------|
| 29A | 2-naphthyl-methyl | 2-(BrCH₂)-naphthalene | 591.2181 | 591.2161 |

-continued

| Ex. | T | Starting Material | Calc'd | Found |
|---|---|---|---|---|
| 29B | 2-fluoro-4-methyl-1-methoxyphenyl (3-F, 4-OCH₃) | BrCH₂-(3-F, 4-OCH₃-phenyl) | 589.2036 | 589.2029 |
| 29C | 3-methylphenyl | BrCH₂-(3-CH₃-phenyl) | 555.2181 | 555.2186 |
| 29D | 4-methylphenyl | BrCH₂-(4-CH₃-phenyl) | 555.2181 | 555.2170 |
| 29E | 2-fluorophenyl | BrCH₂-(2-F-phenyl) | 559.1931 | 559.1931 |
| 29F | 3-fluorophenyl | BrCH₂-(3-F-phenyl) | 559.1931 | 559.1925 |
| 29G | 4-fluorophenyl | BrCH₂-(4-F-phenyl) | 559.1931 | 559.1925 |
| 29H | 2-methoxyphenyl | BrCH₂-(2-OCH₃-phenyl) | 571.2130 | 571.2145 |

| Ex. | T | Starting Material | Analysis Calc'd | Analysis Found |
|---|---|---|---|---|
| 29I | 3-methoxyphenyl | BrCH₂-(3-OCH₃-phenyl) | C, 60.35; H, 6.21; N, 4.54 [$C_{31}H_{36}N_2O_4Cl_2 \cdot HCl, 0.5H_2O$] | C, 60.32; H, 6.23; N, 4.63 |
| 29J | 4-methoxyphenyl | BrCH₂-(4-OCH₃-phenyl) | C, 64.64; H, 6.39; N, 4.86 [$C_{321}H_{36}N_2O_4Cl_2 \cdot 0.25 H_2O$] | C, 64.61; H, 6.41; N, 4.89 |
| 29K | 3,4,5-trimethoxyphenyl | BrCH₂-(3,4,5-tri-OCH₃-phenyl) | C, 61.36; H, 6.49; N, 4.34 [$C_{33}H_{40}N_2O_6Cl_2 \cdot 0.8H_2O$] | C, 61.43; H, 6.40; N, 4.38 |

EXAMPLE 30

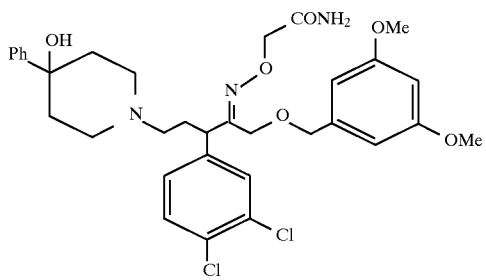

Step 1: Using the procedure of Example 29, replace O-methoxylamine HCl with hydroxylamine in Step 3 obtain 2-[[[2-(3,4-dichlorophenyl)-1-[[(3,5-dimethoxyphenyl) methoxy]methyl]-4-(4-hydroxy-4-phenyl-1-piperidinyl)-2-pentanone oxime.

Step 2: Treat the product of Step 1 (0.40 g) in DMF (10 mL) at 0° C. with NaH (55 mg) then methylbromoacetate (0.115 g). Stir the mixture and allow to warm to room temperature over 2 h. Partition the reaction mixture between EtOAc (50 mL) and H₂O (15 ml). Separate the organic layer, wash with H₂O (2×15 mL), dry over MgSO₄, filter and evaporate. Purify the residue by silical gel chromatography eluting with mixtures of NH₃/MeOH/CH₂Cl₂ to give methyl-2-[[[2-(3,4-dichlorophenyl)-1-[[(3,5-dimethoxyphenyl)methoxy]methyl]-4-(4-hydroxy-4-phenyl-1-piperidinyl)butylidene]amino]oxy]acetate (0.32 g).

Step 3: Treat the product of Step 2 with 4% NH₃/CH₃OH (10 mL) in a sealed bottle and stir for 3 days at room temperature. Evaporate the solution to dryness and purify by silical gel chromatography eluting with mixtures NH₃/MeOH/CH₂Cl₂ to give the title compound (0.25 g). HRMS (FAB, M+H₊): m/e calc'd for $[C_{33}H_{39}N_3O_6Cl_2]^+$: 644.2294, found 644.2282.

EXAMPLE 31

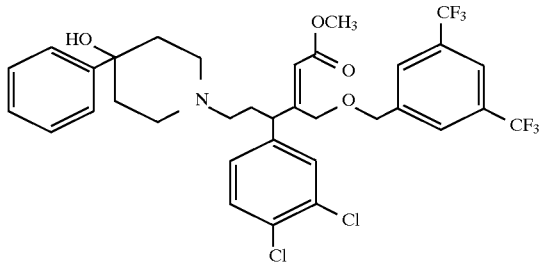

Using a procedure similar to that described in Example 8, treat the ketone of Preparation 4 with diethyl methylphosphonoacetate to obtain the title compound as an E/Z mixture. HRMS (FAB, M+H⁺): m/e calc'd for $[C_{34}H_{34}Cl_2F_6NO_4]^+$: 704.1769, found 704.1757.

EXAMPLE 32

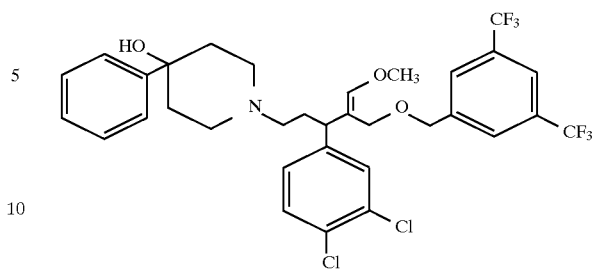

Treat a suspension of $(CH_3OCH_2)Ph_3PBr$ (0.21 g, 0.6 mmol) in dry THF (10 mL) with NaN(TMS)₂ (0.6 mL of a 1.0M solution in THF) at 0° C. After 30 minutes, add the product of Preparation 4 (0.05 g, 0.08 mmol) in dry THF (5 mL) and slowly warm the reaction to room temperature over 1 hour. Stir for 3 hours at room temperature and quench by the addition of water. Extract with CH₂Cl₂ (3×25 mL). Wash the combined organics with brine, dry (Na₂SO₄) and concentrate. Purify the crude material on two preparative TLC plates (20×20 cm, 0.5 mm thickness) eluting with CH₂Cl₂ and CH₃OH saturated with ammonia (98:2) followed by reelution with hexane and 2-propanol (90:10) to provide the product (24 mg, 47%) as a white sticky foam (E/Z mixture). HRMS (FAB, M+H⁺): m/e calc'd for $[C_{33}H_{34}Cl_2F_6NO]^+$: 676.1821, found 1 5 676.1834.

Use the appropriate alkyl-substituted Wittig reagents (alkyl-PPh₃Br) in the procedure of Example 32, to prepare the following compounds:

| Ex. | =A | HRMS calc'd (FAB, M + H⁺) | HRMS Found |
|---|---|---|---|
| 32A | =CH₂ | 646.1714 | 646.1730 |
| 32B | =CH—CH₃ | 660.1870 | 660.1864 |
| 32C | =CH—CH₂—CH₃ | 674.2027 | 674.2013 |

EXAMPLE 33

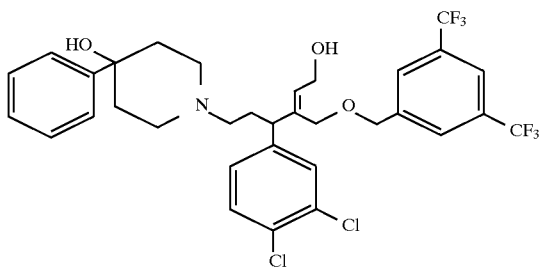

Treat the product of Example 31 (0.69 g, 0.98 mmol) in dry $CH_2Cl_2$ (30.0 mL) at 0° C. with a solution of DiBAl-H (3.9 mL of a 1M solution in $CH_2Cl_2$). Warm to room temperature and stir for 15 minutes. Quench by slowly adding saturated aqueous $Na_2SO_4$. Dilute with water and extract with $CH_2Cl_2$ (3×50 mL), wash with brine, dry ($Na_2SO_4$) and concentrate. Purify the crude material on a flash column (100 g $SiO_2$; eluant $CH_2Cl_2$:$CH_3OH$ saturated with ammonia 95:5) to give the desired product as a white powder (0.52 g, 79%). HRMS (FAB, M+H$^+$): m/e calc'd for $[C_{33}H_{34}Cl_2F_6NO_3]^+$: 676.1820, found 676.1815.

EXAMPLE 34

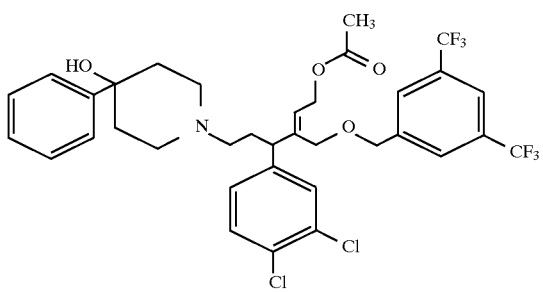

Treat the product of Example 33 (0.5 g, 0.7 mmol) in dry THF (20 mL) with NaH (0.28 g of a 60% dispersion in mineral oil, 7 mmol) and acetic anhydride (0.36 g, 3.5 mmol) at room temperature and stir for 18 hours. Cool to 0° C. and treat with $CH_2Cl_2$ (50 mL) and water (10 mL). Wash the organic layer with water, dry ($Na_2SO_4$) and concentrate. Purify the crude material on a flash column ($SiO_2$; elute with $CH_2Cl_2$:$CH_3OH$ saturated with ammonia 95:5) to give the desired product as a white foam (0.42 g, 79%). HRMS (FAB, M+H$^+$): m/e calc'd for $[C_{35}H_{36}Cl_2F_6NO_4]^+$: 718.1926, found 718.1922.

Using the product of Example 33 as the starting material and the appropriate electrophile in the procedure of Example 34, the following compounds are prepared:

EXAMPLE 34A

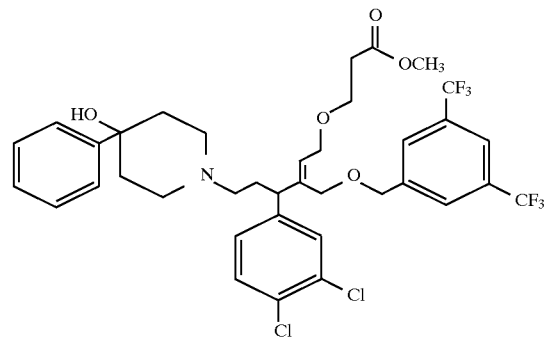

HRMS (FAB, M + H$^+$): m/e calc'd for $[C_{37}H_{39}Cl_2F_6NO_5]^+$: 762.2188, found, 762.2185.

EXAMPLE 34B

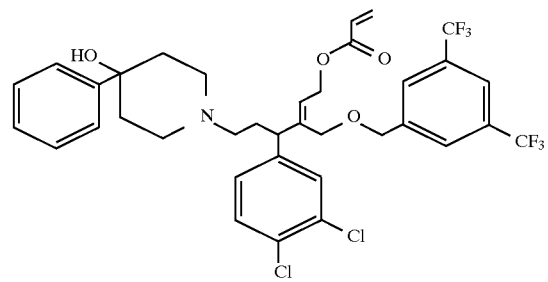

HRMS (FAB, M + H$^+$): m/e calc'd for $[C_{36}H_{36}Cl_2F_6NO_4]^+$: 730.1926, found 730.1925.

EXAMPLES 35, 35A, 35B, 35C

Using the procedures described below, compounds of the following structural formula were prepared, wherein the definitions of A are shown in the table below:

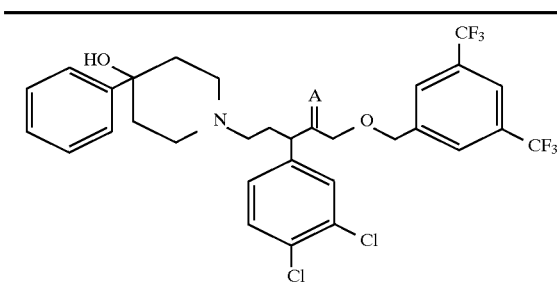

| Ex. | =A | HRMS calc'd (FAB, M + H$^+$) | HRMS Found |
|---|---|---|---|
| 35 | =CH—CH$_2$—N$_3$ | 701.1885 | 701.1885 |
| 35A | =CH—CH$_2$—NH$_2$ | 675.1980 | 675.1979 |
| 35B | =CH—CH$_2$—N(CH$_3$)$_2$ | 703.2293 | 703.2290 |
| 35C | =CHCH$_2$N[(CH$_2$)$_2$OH]$_2$ | 763.2504 | 763.2502 |

EXAMPLE 35

Treat the product of Example 34 (0.8 g, 0.11 mmol) in THF/H$_2$O (5:2, 4 mL) with NaN$_3$ (0.036 g, 5 mmol) and Pd(PPh$_3$)$_4$ (0.013 g, 0.01 mmol) and heat to reflux for 1 hour.

Cool to room temperature and dilute with Et₂O (10 mL). Separate the organic layer and extract the aqueous layer with additional Et₂O (2×5 mL). Wash the combined organic layers with brine, dry (Na₂SO4) and concentrate. Purify the crude material on a flash column (SiO₂; elute with CH₂Cl₂:CH₃OH saturated with ammonia 95:5) to give the desired product as a white sticky foam (0.039 g, 51%).

EXAMPLE 35A

Treat the product of Example 35 (0.21 g, 0.3 mmol) in THF (20 mL) with Ph₃P (0.095 g, 0.36 mmol) and water (0.25 mL) at room temperature and stir for 2 hours. Add additional Ph₃P (0.1 g) and stir for 30 minutes. Concentrate and purify the crude product on a flash column (SiO₂; elute with CH₂Cl₂:CH₃OH saturated with ammonia 90:10) to give the desired product as a dark foam (0.11 g, 50%). HRMS (FAB, M+H⁺): m/e calc'd for $[C_{33}H_{35}Cl_2F_6N_2O_2]^+$: 675.1980, found 675.1979.

EXAMPLE 35B

Use the product of Example 34 as the starting material and dimethylamine in the procedure of Example 35 with THF as the solvent to obtain the desired product.

EXAMPLE 35C

Use the product of Example 34 as the starting material and diethanolamine in the procedure of Example 35 with THF as the solvent to obtain the desired product.

EXAMPLE 36

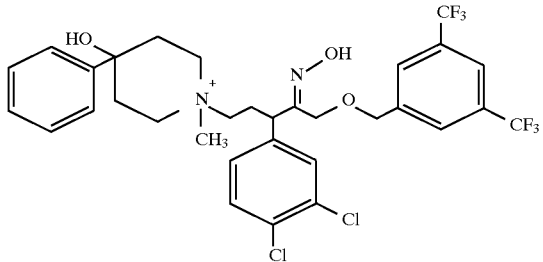

Treat the product of Example 1A (0.036 g, 0.05 mmol) with CH₃I (1 mL) at room temperature and place in the refrigerator for 18 h. Remove the excess CH₃I under a stream of N₂. Dissolve the residue in CH₃OH and add water until turbid. When crystals have formed, remove the solvent with a pipette. Wash the crystals with water and pump dry to give the product as a white solid (0.031 g, 78%) HRMS (FAB, M+H⁺): m/e calc'd for $[C_{32}H_{33}Cl_2F_6N_2O_3]^+$: 677.1772, found 677.1765.

EXAMPLES 37 to 37E

Using the product of Example 1A in the procedure described in Example 8, reacting with 4-bromobutyronitrile, 5-bromovaleronitrile and 6-bromocapronitrile, respectively, the products of Examples 37 to 37B were obtained; subsequent treatment with hydroxylamine as described in Example 11 resulted in compounds 37C to 37E.

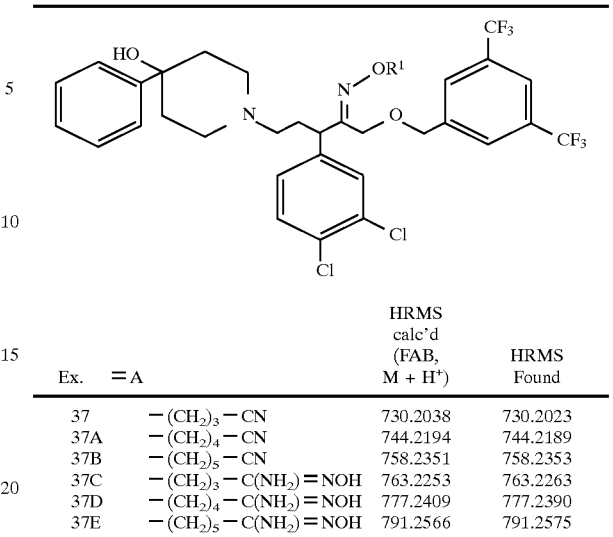

| Ex. | =A | HRMS calc'd (FAB, M + H⁺) | HRMS Found |
|---|---|---|---|
| 37  | —(CH₂)₃—CN              | 730.2038 | 730.2023 |
| 37A | —(CH₂)₄—CN              | 744.2194 | 744.2189 |
| 37B | —(CH₂)₅—CN              | 758.2351 | 758.2353 |
| 37C | —(CH₂)₃—C(NH₂)=NOH      | 763.2253 | 763.2263 |
| 37D | —(CH₂)₄—C(NH₂)=NOH      | 777.2409 | 777.2390 |
| 37E | —(CH₂)₅—C(NH₂)=NOH      | 791.2566 | 791.2575 |

EXAMPLE 38

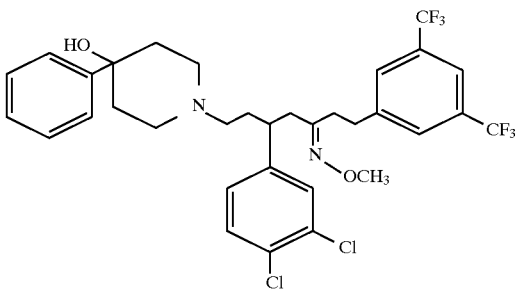

Step 1: Cool a solution of CH₃P(O)(OCH₃)₂ (0.55 g, 4.4 mmol) in dry THF (10 mL) to −780° C. and add n-BuLi (2.75 mL of a 1.6M solution in hexanes) dropwise. Stir for 45 min at −78° C. and add a solution of 4-(3,4-dichlorophenyl)glutaric anhydride (0.52 g, 2 mmol) in dry THF (5 mL). Stir for 2 hours at −78° C. and quench by adding 1N HCl (15 mL). Extract with EtOAc (3×25 mL), wash the combined organic layers with brine, dry (Na₂SO₄) and concentrate. Purify the crude material on a flash column (100 g SiO₂; elute with EtOAc:CH₃OH:HOAc 90:10:2) to give an oil (0.55 g, 75%).

Step 2: Add K₂CO₃ (1.0 g, 7.2 mmol) to a solution of the product of step 1 (2.0 g, 5.2 mmol) and 3,5-bis (trifluoromethyl)benzaldehyde (1.9 g, 7.9 mmol) in dry CH₃CN (60 mL) at room temperature. Stir for 5 hours and filter the crude reaction mixture through filter paper. Concentrate and purify the crude reaction through a flash column (SiO₂; elute with EtOAc: CH₃OH: HOAc 90:10:2) to give a white solid (2.0 9, 77%).

Step 3: React the product of step 2 (5.8 g, 11.6 mmol) with H₂ gas (balloon) in the presence of 10% Pd/C (0.58 g, 10% w/w) for 3 hours at room temperature. Pass the crude reaction through a short pad of silica gel eluting with EtOAc to give 3.7 g of product (64%) to be used directly in the next step.

Step 4: Treat a cooled (0° C.) solution of 4-phenyl-4-hydroxypiperidine (1.6 g, 8.9 mmol) in DMF (50 mL) with 4-methylmorpholine (0.89 g, 8.9 mmol), HOBT (1.0 g, 7.4 mmol) and the product of step 3 (3.7 g, 7.4 mmol). Stir at 0° C. for 30 min and room temperature for 6 h. Concentrate and dilute the residue with 1:1 water:EtOAc (200 mL). Wash the organic layer with brine, dry ($Na_2SO_4$) and concentrate. Purify the crude reaction product on a flash column ($SiO_2$; elute with EtOAc: hexane 4:5) to give a white foam (1.45 g, 35%).

Step 5: Treat a solution of the product of step 4 (0.5 g, 0.75 mmol) in pyridine (30 mL) with $CH_3ONH_2 \cdot HCl$ (0.1 g, 1.2 mmol) and heat to 60° C. for 1.5 hours. Concentrate and purify the residue on a flash column ($SiO_2$; elute with $CH_2Cl_2$:$CH_3OH$ saturated with ammonia 95:5) to give the title compound (0.52 g, 99%) as a white solid and a mixture of E and Z oxime isomers.

Step 6: Treat a solution of the product of step 5 (0.2 g, 0.29 mmol) in $CH_2Cl_2$ (15 mL) at 0° C. with DiBAl-H (64 µL of a 1M solution in $CH_2Cl_2$). After 10 minutes, quench by the addition of saturated aqueous $Na_2SO_4$, dry by the addition of solid $Na_2SO_4$ and concentrate. Purify the crude material on two preparative TLC plates eluting with $CH_2Cl_2$:$CH_3OH$ saturated with ammonia 95:5 to give the title compound (0.027 g, 14% of oxime isomer A and 0.046 g, 24% of oxime isomer B). Isomer A: HRMS (FAB, M+H$^+$): m/e calc'd for $[C_{33}H_{35}Cl_2F_6N_2O_2]^+$: 675.1980, found 675.1986. Isomer B: HRMS (FAB, M+H$^+$): m/e calc'd for $[C_{33}H_{35}Cl_2F_6N_2O_2]^+$: 675.1980, found 675.1986.

EXAMPLE 39

The compounds described in Examples 39 to 39N are prepared in a similar manner to that described in Example 20, using the appropriate oxime and the appropriate amine:

| Example | Z | $R^1$ | HRMS (FAB, M + H$^+$) Calculated | HRMS (FAB, M + H$^+$) Found |
|---|---|---|---|---|
| 39 | H$_2$N-C(=O)-C(Ph)(piperidine-N-CH$_3$)- | —(CH$_2$)$_2$OH | 734.1987 | 734.2001 |
| 39A | piperidine-N-(piperidin-4-yl)-N— | H | 654.2089 | 654.2082 |
| 39B | piperidine-N-(piperidin-4-yl)-N— | —(CH$_2$)$_2$OH | 698.2351 | 698.2349 |
| 39C | H$_2$N-C(=O)-C(Ph)(piperidine-N-CH$_3$)- | —CH$_2$CN | 729.1834 | 729.134 |
| 39D | H$_2$N-C(=O)-C(Ph)(piperidine-N-CH$_3$)- | N-OH with =C(Et)NH$_2$ | 762.2049 | 762.2042 |
| 39E | piperidine-N-(piperidin-4-yl)-N— | —CH$_2$CN | 693.2198 | 693.2206 |

-continued
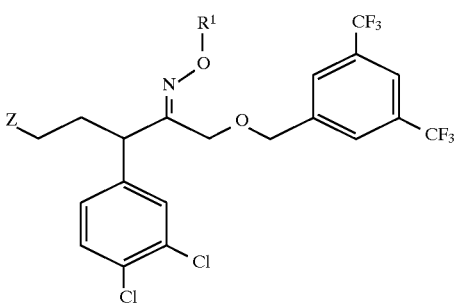
| Example | Z | R¹ | HRMS (FAB, M + H⁺) Calculated | HRMS (FAB, M + H⁺) Found |
|---|---|---|---|---|
| 39F | 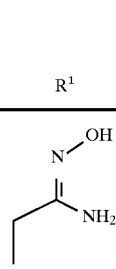 | 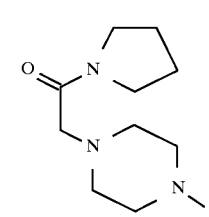 | 726.2412 | 726.2412 |
| 39G | 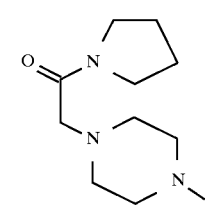 | H | 683.1990 | 683.1993 |
| 39H | 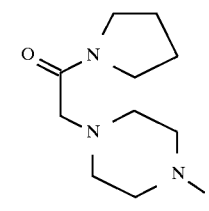 | —CH$_2$CN | 722.2099 | 722.2088 |
| 39I | 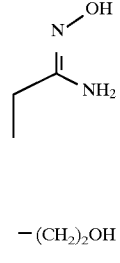 | 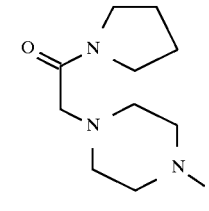 | 755.2314 | 755.2305 |
| 39J | 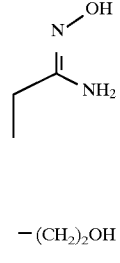 | —(CH$_2$)$_2$OH | 727.2253 | 727.2229 |
| 39K | 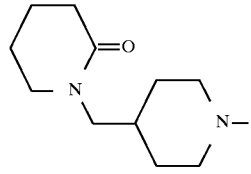 | H | 682.2038 | 682.2042 |

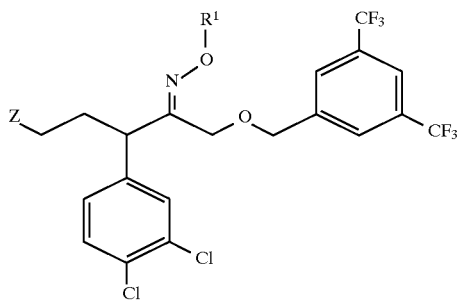

| Example | Z | R¹ | HRMS (FAB, M + H⁺) Calculated | HRMS (FAB, M + H⁺) Found |
|---|---|---|---|---|
| 39L | | —CH₂CN | 721.2147 | 721.2136 |
| 39M | | $\underset{NH_2}{\overset{OH}{\underset{\|}{N}}}$ | 754.2362 | 754.2371 |
| 39N | | —(CH₂)₂CN | 726.2300 | 726.2283 |

EXAMPLES 40 and 40A

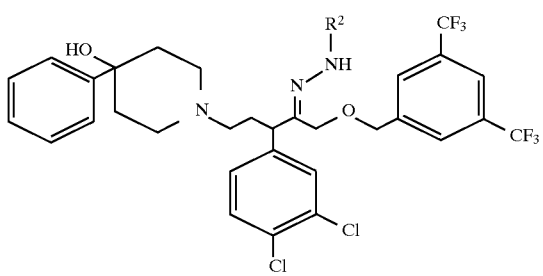

EXAMPLE 40

R² is —C(O)NH₂

Reflux the product of Preparation 4 (52 mg) in EtOH (1.5 mL) with semicarbazide HCl (75 mg) and KOAc (75 mg) for 1 h. Extract the resultant mixture with water, NaHCO₃ and CH₂Cl₂, dry the organic layer and evaporate to obtain a white foam. MASS (FAB, M+H⁺) m/e 705.

EXAMPLE 40A

R² is —C(O)CH₃

Reflux the product of Preparation 4 (42 mg) in EtOH (1.5 mL) with acetylhydrazide (80 mg) and HOAc (25 mg) for 1 h. Extract as in Example 40 and isolate the product by preparative TLC on silica gel, eluting with CH₂Cl₂:CH₃OH (12:1) to obtain the desired compound as a foam. MASS (FAB, M+H⁺) m/e 704

EXAMPLE 41

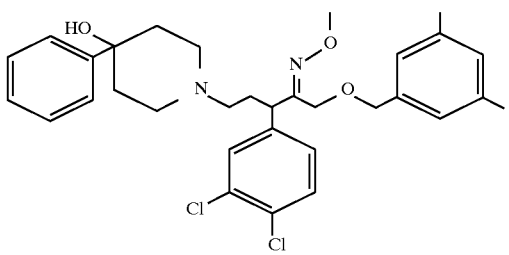

Step 1: 3-(3,4-dichlorophenyl)-dihydro-2(3H)-furanone

Heat [(CH₃)₃Si]₂NLi (230 ml, 1.0M in THF) under N₂ to 45° C. and add 3,4 dichlorophenyl acetic acid methyl ester (40 g, 0.183 moles) dissolved in 60 ml of dry THF dropwise over 2 h. Stir the solution at 45° C. for another 2.5 h. Cool the solution to room temperature, add a dry THF solution (30 ml.) of THP-protected Br(CH₂)₂OH dropwise over 1 h., and stir the solution for 24 h. Cool the solution in an ice bath and quench the reaction by adding, dropwise, 250 ml. of 1.0M aqueous HCl. Extract the solution with Et$_2$O, wash the organic layer twice with 1.0M aqueous HCl, then with water, and dry over anhydrous Na$_2$SO$_4$. Remove the solvent, dissolve the residue in CH$_3$OH and add 0.5 g of pTSA. Stir the solution at room temperature overnight, remove the solvent, add CH$_3$OH (500 ml) and stir for 6 h. Remove the solvent again, add more CH$_3$OH (500 ml.), stir overnight and remove the solvent. Dissolve the resulting oil in CH$_2$Cl$_2$ (1200 ml.), wash twice with saturated aqueous NaHCO$_3$, then water, and dry over anhydrous Na$_2$SO$_4$. Remove the solvent in vacuo. Purify the reaction mixture by flash chromatography (SiO$_2$) using EtOAc: hexanes (3:7) as eluent. Yield: 22 g. Cl-MS: 231 (100%), 233 (65%).

Step 2: alpha-(2-bromoethyl)-3,4-dichlorophenylacetic acid

Treat the product of Step 1 (21.25 g, 91.96 mmoles) at room temperature with 130 ml. of HOAc saturated with HBr gas. Stir at room temperature for 2 days, then pour into 800 ml. of ice-water with stirring. Store the resultant gum in a freezer for two days, then decant the liquid from the solidified gum. Triturate the solid, filter, wash with water and air dry. Yield: 26.2 g (m.p.=80°–81° C.).

Step 3: alpha-(2-bromoethyl)-3,4-dichlorophenylacetic acid chloride

Dissolve the product of Step 2 (8.1 g, 25.96 mmoles) in 20 ml. of dry CH$_2$Cl$_2$. Add oxalyl chloride (8.1 g, 62.3 mmoles), followed by 50 µl of dry DMF and heat the solution to reflux for 3 h. Cool the solution to room temperature and remove the solvent and excess reagent using reduced pressure. Yield: 8.2 g (IR: 1785 cm$^{-1}$).

Step 4: 5-bromo-1-diazo-3-(3,4-dichlorophenyl)--2-pentanone

Prepare a solution of diazomethane from 15 g of MNNG by reaction with 45 ml of 40% aqueous KOH topped with 150 ml. of Et$_2$O and cool in an ice bath. Add an Et$_2$O solution (40 ml.) of the product of Step 3 (8.2 g, 5 24.8 mmoles) in small volumes, stir the solution in the ice bath for 15 min, then heat to reflux for 30 min. Remove the solvent in vacuo. Purify the resulting mixture by flash chromatography on silica gel using CH$_2$Cl$_2$ as eluent. Yield: 7.0 g (IR: 2100 cm$^{-1}$, 1630 cm$^{-1}$).

Step 5: 1-diazo-3-(3,4-dichlorophenyl)-5-(4-hydroxy-4-phenyl-1-piperidinyl)-2-pentanone Dissolve the product of Step 4 (3.93 g, 11.7 mmoles) in 50 ml of dry EtOAc. Add 4-hydroxy-4-phenyl-1-piperidine (2.55 g, 14.4 mmoles), followed by dry Et$_3$N (13.3 ml.). Heat under N$_2$ at 60°–65° C. for 28 h. Cool to room temperature, filter the solid and wash with EtOAc. Apply the filtrate 1 5 to a silica gel column and elute the column with 1.5% CH$_3$OH(NH$_3$)/EtOAc. Yield: 2.34 g; Cl-MS: m/e=432 (M+H$^+$, $^{35}$Cl+$^{37}$Cl isotope).

Step 6: 3-(3,4-dichlorophenyl)-1-[(3,5-dimethylphenyl)methoxy]-5-(4-hydroxy-4-phenyl-1-piperidinyl)-2-pentanone Dissolve 3,5-dimethyl benzyl alcohol (1.32 g, 9.71 mmoles) in 4.0 ml of dry CH$_2$Cl$_2$ and add BF$_3$ etherate (0.44 ml, 3.56 mmoles). Add a dry CH$_2$Cl$_2$ solution (2.0 ml.) of the product of Step 5 (0.7 g, 1.62 mmoles) dropwise at room temperature, under N$_2$, over a period of 4.5 h. Stir the mixture at room temperature for another 30 min, then quench the reaction with water (6.0 ml) followed, after 10 min of stirring, by Et$_3$N (2.0 ml). Stir for 15 min, then dilute with 90 ml of CH$_2$Cl$_2$. Wash the organic layer with water and dry it over anhydrous Na$_2$SO$_4$. Purify the reaction mixture by flash chromatography (SiO$_2$), eluting the column first with 30% EtOAc/hexanes, then, after elution of the excess of 3,5-dimethyl benzyl alcohol, change the eluent to 40% EtOAc/Hexanes. Yield: 0.435 g. HRMS (FAB, M+H$^+$): m/e calc'd for [C$_{31}$H$_{36}$NO$_3$Cl$_2$]$^+$: 540.2072; found 540.2075.

Step 7: Add methoxylamine HCl (75 mg, 0.9 mmoles) to the product of Step 6 (0.32 g, 0.59 mmoles) dissolved in 3.0 ml of dry pyridine. Heat the solution under N$_2$, at 60°–65° C. for 90 min, then remove the pyridine in vacuo. Purify the reaction mixture by preparative TLC, eluting the silica gel plates with EtOAc:Hexanes:CH$_3$OH(NH$_3$) (25:75:2.5). Extract the title compound with MeOH(NH$_3$):EtOAc (5:95). Yield: 0.209 g. HRMS (FAB, M+H$^+$): m/e calc'd for [(C$_{32}$H$_{39}$N2O$_3$Cl$_2$]$^+$: 569.2338; found 569.2335.

Examples 41A to 41P are prepared from the product of Example 41, Step 5, by reaction with suitable alcohols or mercaptansusing a procedure similar to the one described for Example 41, Step 6. The resulting ketones are reacted with methyloxime hydrochloride using a 5 procedure similar to the one described in Example 41, Step 7.

| Ex. | —X—(C)$_b$—T  R$^9$ / R$^8$ | HRMS calc'd (FAB M + H$^+$) | hrms Found |
|---|---|---|---|
| 41A | (3,5-dimethoxybenzyl ether, OCH$_3$/OCH$_3$) | 601.2236 | 601.2230 |
| 41B | (3,5-dichlorobenzyl ether, Cl/Cl) | 609.1245 | 609.1247 |
| 41C | (cyclohexylmethyl ether) | 547.2494 | 547.2487 |
| 41D | (3-trifluoromethylbenzyl thioether, CF$_3$) | 625.1670 | 625.1664 |

-continued

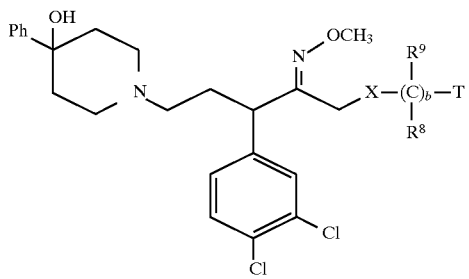

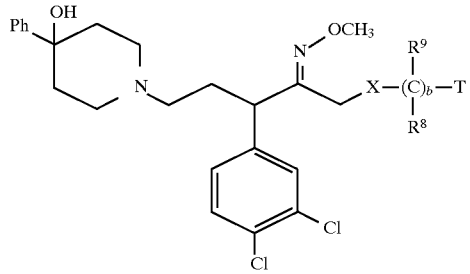

| Ex. | —X—(C)$_b$—T with R$^9$/R$^8$ | HRMS calc'd (FAB M + H$^+$) | hrms Found |
|---|---|---|---|
| 41E | (methylthio-CF$_3$-phenyl) | 611.1514 | 611.1511 |
| 41F | (methoxyethyl-3,5-dimethylphenyl) | 583.2494 | 583.2487 |
| 41G | (methoxyethyl-3,5-bis(CF$_3$)phenyl) | 691.1929 | 691.1932 |
| 41H | (methoxymethyl-3,5-difluorophenyl) | 577.1836 | 577.1843 |
| 41I | (methoxymethyl-3-CF$_3$-5-F-phenyl) | 627.1804 | 627.1809 |
| 41J | (methoxymethyl-biphenyl) | 617.2338 | 617.2329 |
| 41K | (methoxymethyl-adamantyl, isomer A) | 599.2807 | 599.2810 |
| 41L | (methoxymethyl-adamantyl, isomer B) | 599.2807 | 599.2810 |
| 41M | (methoxyethyl-3,5-dichlorophenyl) | 623.1402 | 623.1393 |
| 41N | (methoxymethyl-3,5-dibromophenyl) | 697.0235 | 697.0243 |
| 41O | (methoxymethyl-dimethylbicyclic) | 587.2807 | 587.2810 |

EXAMPLE 42

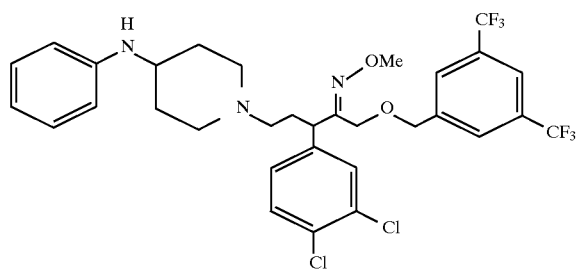

Step 1: Methyl 3-(3,4-dichlorophenyl)-3-[2-(ethoxycarbonyl)-2-(1,3-dithiolanyl)]-propanoate Dissolve [(CH$_3$)$_3$Si]$_2$NLi (171.0 mL of 1.0M solution, 0.171 mol) in dry THF (170 mL), cool to −78° C. under N$_2$, add ethyl 1,3-dithiolane-2-carboxylate (33.2 g, 0.186 mol) in dry THF (120 mL) dropwise and stir at −78° C. for 20 mins. Add methyl 3,4-dichlorocinnamate (34.8 g, 0.150 mol) in DMPU (180 mL) dropwise. Stir at −78° C. for 5 h. Add CH$_3$OH (30 mL), warm to −30° C. and add saturated aqueous NH$_4$Cl (500 mL) and water (500 mL). Extract with EtOAc (3×400 mL), dry combined organic extracts (MgSO$_4$), filter and concentrate. Purify by chromatography (2.5 L of flash silica gel; eluant: 5% EtOAc-hexane then 15% EtOAc-hexane). Combine appropriate fractions and concentrate to give 53.6 g (0.131 mol, 87%) of the title compound as a colorless oil. MS (FAB): m/e 409 (M+1)

Step 2: 2-(Hydroxymethyl)-2-[3-[3-(3,4-dichlorophenyl)-1-hydroxy]-propyl]-1,3-dithiolane Dissolve the product (75.10 g, 0.183 mol) of Step 1 in dry THF (700 mL), cool to 0° C. under N$_2$, add LiAlH$_4$ (275 mL of 1.0M in Et$_2$O, 0.275 mol) dropwise and stir at 0° C. for 30 mins, then at 23° C. for 16 h. Add water (10 mL) dropwise followed by 25 wt % NaOH (10 mL). Dilute with CH$_2$Cl$_2$ (500 mL) and filter through celite. Extract celite with CH$_2$Cl$_2$ via a soxhlet extractor. Concentrate combined organic solutions and triturate with hexane to give 56.8 g (0.167 mol, 92%) of the title compound as a white solid (mp=122°–124° C.). MS (FAB): m/e 339 (M+1)

Step 3: 2-(Hydroxymethyl)-2-[3-[3-(3,4-dichlorophenyl)-1-[dimethyl(1,1-dimethylethyl)silyloxy]]-propyl]-1,3-dithiolane Dissolve the product (67.80 g, 0.200 mol) of Step 2 in dry THF (1300 mL), add Et$_3$N (30.30 g, 41.8 mL, 0.300 mol) and dimethylamino-pyridine (4.90 g, 0.040 mol) and cool to 0° C. under N$_2$. Add t-butyl-dimethylsilyl chloride (36.14 g, 0.240 mol) in dry THF (200 mL) dropwise. Warm slowly to 23° C. and stir for 72 h. Add water (1000 mL), extract with EtOAc, dry combined organic extracts (MgSO$_4$), filter, and concentrate. Purify by chromatography (2.0 L of flash silica, eluant 1:2 EtOAc:hexane). Combine appropriate fractions and concentrate to give 89.4 g (0.197 mol, 99%) of the title compound as a colorless oil. MS (FAB): m/e 453 (M+t)

Step 4: 2-[[3,5-Bis(trifluoromethyl)phenyl]methoxymethyl]-2-[3-[3-(3,4-dichlorophenyl)-1-[dimethyl(1,1-dimethylethyl)silyloxy]]-propyl]-1,3-dithiolane Dissolve the product (89.40 g, 0.197 mol) of Step 3 in dry THF (1 L), cool to 0° C. under N$_2$, add [(CH$_3$)$_3$Si]$_2$NK (434 mL of 0.5M solution, 0.217 mol) dropwise. Add 3,5-bis(trifluoromethyl)benzyl bromide (75.65 g, 45.2 mL, 0.246 mol), stir at 0° C. for 30 mins, then warm slowly to 23° C. Reflux for 16 h, then cool to 23° C. Add saturated aqueous NH$_4$Cl (500 mL) and water (500 mL), extract with EtOAc, dry combined organic extracts (MgSO$_4$), filter, and concentrate. Purify by chromatography (3.0 L flash silica, eluant: 10% CH$_2$Cl$_2$-hexane, 20% CH$_2$Cl$_2$-hexane, then 25% CH$_2$Cl$_2$-hexane). Combine appropriate fractions and concentrate to give 105.5 g (0.155 mol, 79%) of a yellow oil. MS (FAB): m/e 547 (M+1)

Step 5: 2-(Hydroxymethyl)-2-[3-[3-(3,4-dichlorophenyl)-1-[dimethyl(1,1-dimethylethyl)silyloxy]]-propyl]-1,3-dithiolane Dissolve the product (80.30 g, 0.118 mol) of Step 4 in CH$_3$CN (750 mL) and add 48% aqueous HF (55.2 mL, 1.53 mol), stir at 23° C. for 16 h, concentrate and add water (300 mL). Add 2.0N NaOH until pH is 3–4 and then add saturated aqueous NaHCO$_3$. Extract with CH$_2$Cl$_2$, wash combined organic extracts with saturated aqueous NaCl, dry (MgSO$_4$), filter, and concentrate to give 66.7 g (0.118 mol, 100%) of a yellow oil.

Step 6: 1-[[3,5-Bis(trifluoromethyl)phenyl]methoxy]-3-(3,4-dichloro-phenyl)-5-hydroxy-2-pentanone Dissolve the product (99.8 g, 0.176 mol) of Step 5 in THF (1000 mL) and water (1 05 mL), add CaCO$_3$ (44.10 g, 0.440 mol), stir for 5 mins, then add Hg(ClO$_4$)$_2$ (159.7 g, 0.352 mol) in water (185 mL) dropwise. Stir the resultant white precipitate at 23° C. for 5 h, filter, wash the solid with water and EtOAc. Separate layers of filtrate and extract with EtOAc. Wash combined organic extracts with saturated aqueous NaCl, dry (MgSO$_4$), filter, and concentrate to give 86.1 g (0.176, 100%) of the title compound as a yellow oil. MS (FAB): m/e 471 (M+1—H$_2$O)

Step 7: 1-[[3,5-Bis(trifluoromethyl)phenyl]methoxy]-3-(3,4-dichloro-phenyl)-5-hydroxy-2-pentanone O-methyloxime Dissolve the product (86.1 g, 0.176 mol) of Step 6 in EtOH (840 mL) and water (165 mL), add CH$_3$CO$_2$Na (72.2 g, 0.881 mol) and CH$_3$ONH$_2$ HCl (44.12 g, 0.528 mol). Reflux for16 h, cool to 23° C. and concentrate. Add water (800 mL), extract with CH$_2$Cl$_2$, treat organic extracts with charcoal and MgSO$_4$, filter, and concentrate. Purify by chromatography (2.0 L of flash silica, eluant: 1:1 CH$_2$Cl$_2$:hexane then 1:1 EtOAc:hexane). Combine appropriate fractions and concentrate to give 67.6 g (0.130 mol, 74%) of the title compounds as a yellow oil. The E and Z oxime isomers can be separated by chromatography (10.0 g of mixture on 1.5 L of flash silica; eluant: 10% EtOAc-hexane, 20% EtOAc-hexane, then 30% EtOAc-hexane; gives 6.57 g of desired Z isomer). MS (FAB): m/e 518 (M+1)

Step 8: 1-[[3,5-Bis(trifluoromethyl)phenyl]methoxy]-3-(3,4-dichloro-phenyl)-4-formyl-2-butanone O-methyloxime Dissolve oxalyl chloride (2.01 g, 15.82 mmol) in dry CH$_2$Cl$_2$ (30 mL) and cool to −78° C. under N$_2$, add DMSO (2.47 g, 31.64 mmol) in dry CH$_2$Cl$_2$ (12 mL) dropwise and stir at −78° C. for 15 mins. Add the product of Step 7 (6.56 g, 12.66 mmol) in dry CH$_2$Cl$_2$ (20 mL) dropwise and stir at −78° C. for 3 h. Add diisopropylethylamine (4.91 g, 37.97 mmol) and stir at −78° C. for 1 h. Warm slowly to 0° C. and stir at 0° C. for 30 mins. Add water (150 mL) and extract with CH$_2$Cl$_2$. Wash combined organic extracts with saturated aqueous NaCl, dry (MgSO$_4$), filter, and concentrate to give 6.53 g (12.66 mmol, 100%) of a yellow oil. MS (FAB): m/e 516 (M+1).

Step 9: Dissolve the product (1.05 g, 2.03 mmol) of Step 8 and 4-phenylamino-piperidine (1.08 g, 6.13 mmol) in CF$_3$CH$_2$OH (10 mL), add crushed 3A sieves (1 g) and NaBH$_3$CN (0.26 g, 4.07 mmol), and stir at 23° C. for 4 h. Concentrate and add water (60 mL) and EtOAc (60 mL). Filter through celite, separate layers of filtrate and extract aqueous solution with EtOAc. Dry combined organic extracts (MgSO$_4$), filter and concentrate. Purify by chromatography (200 mL of flash silica gel; eluant:3% CH$_3$OH—CH$_2$Cl$_2$). Combine appropriate fractions and concentrate to give 0.98 g (1.45 mmol, 66%) of the title compound as a yellow oil. MS (FAB): m/e 676 (M+1)

The following compounds of formula 42A to 42Z are prepared by reacting the product of Example 42, Step 8, with an appropriate amine according to the procedure of Example 42, Step 9:

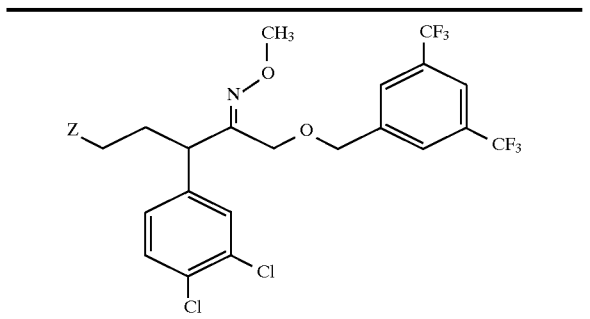
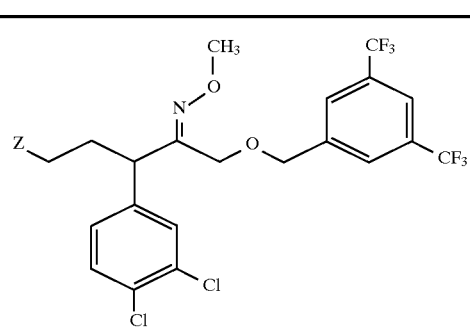

| Ex. | Z | MS (FAB): m/e |
|---|---|---|
| 42A | (dimethylamino)-N-methylpiperidine | 628 (M + 1) |
| 42B | N-methylpiperazine (HN) | 586 (M + 1) |
| 42C | 1-(N-methylpiperidin-4-yl)piperidin-2-one | 682 (M + 1) |
| 42D | 1-(N-methylpiperidin-4-yl)pyrrolidin-2-one | 669 (M + 1) |
| 42E | 1-(N-methylpiperidin-4-yl)piperidine-2-thione | 684 (M + 1) |
| 42F | 4-cyclohexyl-N-methylpiperazine | 668 (M + 1) |
| 42G | morpholine (isomer A) | 587 (M + 1) |
| 42H | morpholine (isomer B) | 587 (M + 1) |
| 42I | N-(N-methylpiperidin-4-yl)benzamide | 704 (M + 1) |
| 42J | ethyl N-methylpiperidine-4-carboxylate | 657 (M + 1) |

| Ex. | Z | MS (FAB): m/e |
|---|---|---|
| 42K | carboxamide spiro piperidine | 711 (M + 1) |
| 42L | 1-(N-methylpiperidin-4-ylcarbonyl)pyrrolidine | 682 (M + 1) |
| 42M | 1-((N-methylpiperidin-4-yl)methyl)piperidin-2-one | 697 (M + 1) |
| 42N | 1-((N-methylpiperidin-4-yl)methyl)pyrrolidin-2-one | 682 (M + 1) |
| 42O | 1-((N-methylpiperidin-4-yl)methyl)piperidine-2-thione | 712 (M + 1) |
| 42P | 1-((N-methylpiperidin-4-yl)methyl)piperidine | 683 (M + 1) |
| 42Q | 3-(cyclopropylmethyl)-1-((N-methylpiperidin-4-yl)methyl)piperidin-2-one | 750 (M + 1) |

-continued

| Ex. | Z | MS (FAB): m/e |
|---|---|---|
| 42R | (allyl-substituted piperidinone with N-methylpiperidinylmethyl) | 736 (M + 1) |
| 42S | HO-pyrrolidine linked to N-methylpiperidine | 670 (M + 1) |
| 42T | H₂N-C(O)- piperidine linked to N-methylpiperidine | 711 (M + 1) |
| 42U | bicyclic diamine with N-methyl | 680 (M + 1) |
| 42V | HO-CH₂-piperidine linked via methylene to N-methylpiperidine | 712 (M + 1) |
| 42W | HOCH₂-piperidine linked via methylene to N-methylpiperidine | 712 (M + 1) |
| 42X | HO-piperidine linked via methylene to N-methylpiperidine | 698 (M + 1) |
| 42Y | piperidine linked to N-methylpyrrolidine | 654 (M + 1) |

-continued

| Ex. | Z | MS (FAB): m/e |
|---|---|---|
| 42Z | benzamido-pyrrolidine N-methyl | 690 (M + 1) |

EXAMPLE 43

Dissolve the product (0.380 g, 0.578 mmol) of Example 42J in THF (3 mL) and CH₃OH (1 mL). Add 1N KOH (2.7 mL, 2.70 mmol) and reflux for 16 h. Cool to 23° C. and add 1N HCl (5 mL) and water (20 mL). Extract with CH₂Cl₂ (3×20 mL), wash combined organic extracts with saturated aqueous NaCl, dry (MgSO₄), filter and concentrate to give 0.312 g (0.496 mmol, 86%) of the title compound as a yellow foam. MS (FAB): m/e 629 (M+1)

EXAMPLE 44

Dissolve 3-pyrrolidinol (0.033 g, 0.375 mmol) in dry THF (2 mL) and cool to 0° C. under N₂. Add diisopropylethylamine (0.097 g, 0.13 mL, 0.750 mmol) then add bromoacetyl bromide (0.076 g, 0.033 mL, 0.375 mmol) in dry THF (1 mL). Stir at 0° C. for 30 mins. Add the product (0.20 g, 0.341 mmol) of Example 42B in dry THF (3 mL), warm to 23° C. slowly and stir for 16 h. Concentrate, add water (20 mL), extract with EtOAc, wash combined organic extracts with saturated aqueous NaCl, dry (MgSO$_4$), filter, and concentrate. Purify by chromatography (70 mL of flash silica gel; eluant: 10% CH$_3$OH—CH$_2$Cl$_2$ then 20% CH$_3$OH—CH$_2$Cl$_2$). Combine appropriate fractions and concentrate to give 0.118 g (0.165 mmol, 49%) of the title compound as a yellow oil.MS (FAB): m/e 713 (M+1).

Using the appropriate amine in the procedure of Example 44, the following compounds of formula 44A and 44B are prepared:

EXAMPLE 44A

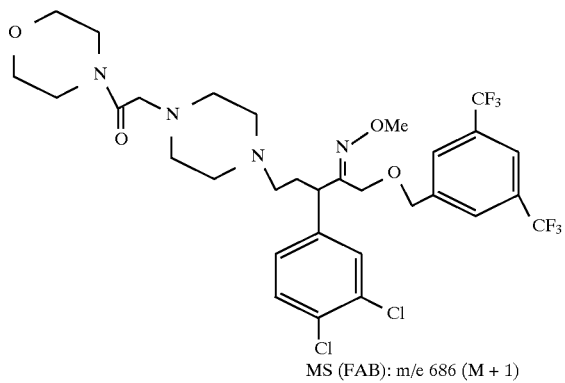

MS (FAB): m/e 686 (M + 1)

EXAMPLE 44B

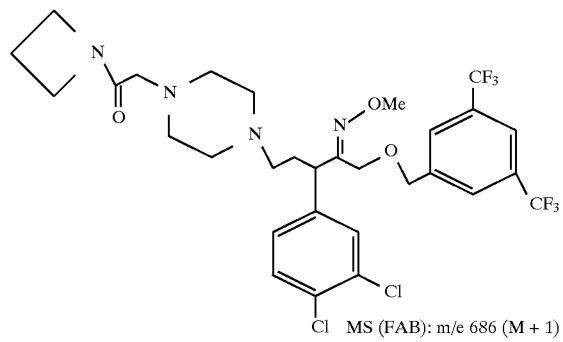

MS (FAB): m/e 686 (M + 1)

EXAMPLE 45

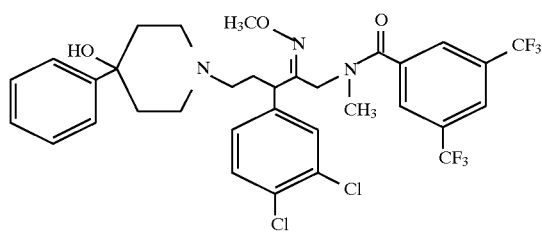

-continued

Step 1:

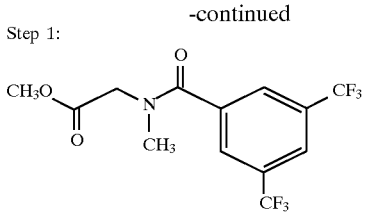

Treat a suspension of sarcosine methyl ester hydrochloride (6.02 g,43 mmole) in CH$_2$Cl$_2$ (250 ml) at 0° C. with 3,5-bistrifluoromethyl benzoyl chloride (7.7 ml, 42.5 mmole) and Et$_3$N (12.5 ml, 89.7 mmole). Stir the mixture at 20° C. for 1 h. Add water (150 ml) to the mixture and separate the organic layer. Dry (MgSO$_4$) and concentrate the organic layer to give crude product. Purify by silica gel chromatography (eluant: EtOAc:hexane (6:4)) to obtain 12 g (81%).

Step 2:

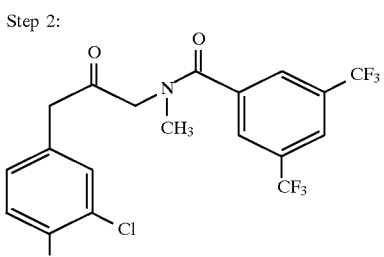

Treat a solution of 3,4-dichlorolphenyl acetic acid (4.15 g, 20 mmole) in anhydrous THF (50 ml) at −60° C. with [(CH$_3$)$_3$Si]$_2$NLi (46.2 ml, 46.2 mmole) and slowly warm the mixture to 0° C. for 4 h. Transfer this solution to a solution of the product of Step 1 (5.46 g, 16 mmole) in anhydrous THF (8 ml) at −30° C. Warm the reaction to −10° C. over 1 h, stir at 0° C. for 1 h and at 20° C. for 4h. Add 50% of aqueous HOAc (15 ml) and extract with EtOAc twice. Separate the organic layer, dry (MgSO$_4$) and concentrate to give the crude product. Purifiy by silical gel chromatography (eluant: hexane/EtOAc, 6:4) to give 5.21 g (69%) of the product. HRMS (FAB, M+H$^+$)=m/e calc'd for [C$_{19}$H$_{14}$NO$_2$Cl$_2$F$_6$]$^+$=472.0306, found 472.0306

Step 3:

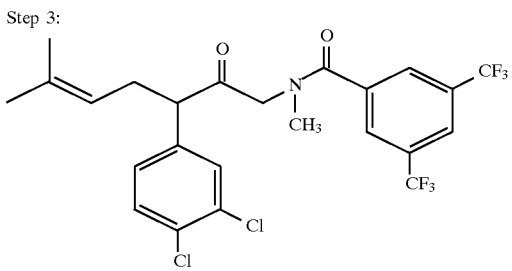

Treat a solution of the product of Step 2 (0.96 g, 2 mmole) in THF (6 ml) at −78° C. with [(CH$_3$)$_3$Si]$_2$NLi (2.5 ml, 2.5 mmole) and stir at −78° C. for 25 h. Add a solution of 1-bromo-3-methyl-2-butene (0.42 g) in THF (1 ml) to the above anion solution at −78° C., slowly warm the solution to 0° C. and stir at 20° C. for 2 h. Add saturated NH$_4$Cl solution (5 ml), extract with EtOAc twice wash the combined EtOAc extracts with brine, dry (MgSO$_4$) and concentrate to give a crude product. Purify by column chromatography (silica gel; eluant: EtOAc:hexane, 2:8) to obtain 1 g of product (87%). MS (FAB, M++) m/e 540.

Step 4:

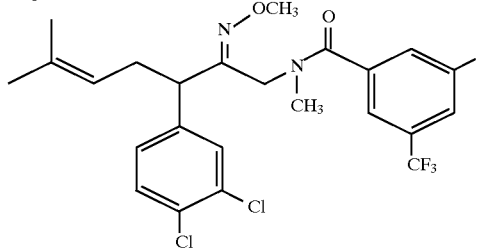

Treat a solution of the product of Step 3 (0.22 g, 0.4 mmole) in pyridine (3 ml) at 70° C. with methoxyamine HCl (95 mg, 1.14 mmole), stir at 70° C. for 6.5 h and then cool to 20° C. Add water to the reaction mixture, extract the solution with EtOAc, dry (MgSO$_4$) and concentrate the EtOAc extracts to give the crude product. Purify by silica gel chromatography (eluant: hexane:Et$_2$O, 1:1) to give 74 mg (32%) of Z-isomer and 130 mg (56%) of E-isomer oximes. MS (FAB, M+H$^+$)=m/e 569.

Step 5:

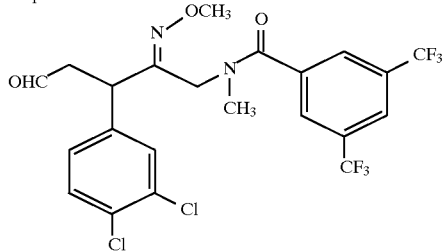

Treat the product of Step 4 (0.387 of E-isomer, 0.68 mmole) in a solution of EtOAc saturated with O$_3$ (7.5 ml) at −78° C. for 5 min. Purge the solution with N$_2$, add (CH$_3$)$_2$S (1.5 ml) and warm the solution from −78° C. to 20° C. over 1 h. Concentrate the solution to give the desired aldehyde which is used directly in the next reaction without further purification. MS (FAB.M +H$^+$)=m/e 543.

Step 6: Treat the product of Step 5 with 4-hydroxy-4-phenylpiperidine in a procedure similar to that described in Example 42, Step 9, to obtain the title compound in overall 77% yield. HRMS(FAB,M$^+$H$^+$)=m/e calc'd for [c33H34N3O3Cl2F6]$^+$:704.1881, found 704.1875.

EXAMPLE 46

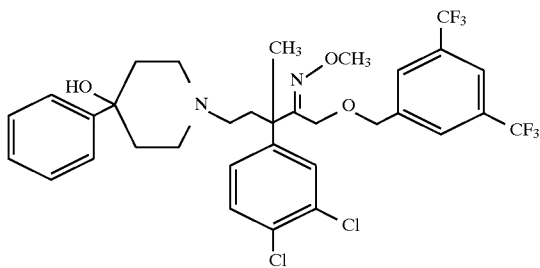

By following a procedure similar to that of Example 45, using the appropriate reagents, the title compound is prepared. HRMS(FAB, M+H$^+$)=m/e calc'd for [C$_{33}$H$_{34}$N$_2$O$_3$Cl$_2$F$_6$]$^+$=691.192, found 691.1938.

EXAMPLE 47

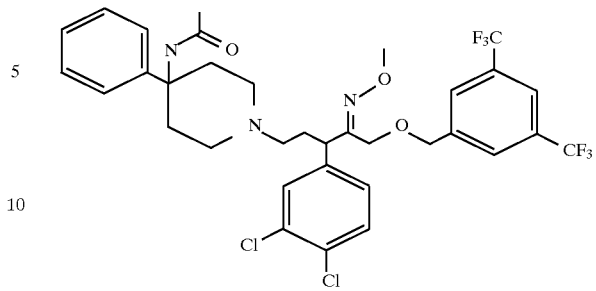

Step 1: Stir a solution of 2-chloro-N-methyl-N-methoxy acetamide (28.2 g, 205 mmol), 3,5-bistrifluoromethyl benzyl alcohol (50.0 g, 205 mmol, 1 eq) and CsCO$_3$ (134 g, 416 mmol) in dry DMF (410 mL) for 20 h. Pour into 1 L Et$_2$O+500 mL hexane+500 mL water. Extract the water layer with 2×1 L Et$_2$O, combine the organic layers, wash with water (2×500 mL) followed by brine (500 mL). Dry over MgSO$_4$, concentrate in vacuo to give 70.2 g (>99%) of the product as a viscous oil.

Step 2: Treat a suspension of Mg turnings (1.8 g) in dry Et$_2$O (12 mL) at 30° C. with a-3,4-trichlorotoluene (10.2 mL) in Et$_2$O (65 mL) dropwise over 1 h, then stir at 23° C. for 20 min. Add the Grignard reagent dropwise to a solution of the product of step 1 (15.0 g, 43.4 mmol) in 350 mL Et$_2$O at −78° C. Stir for 15 min at −78° C., warm to 23° C., pour into 500 mL 0.5N HCl. Extract with Et$_2$O, combine organic layers, wash with brine, dry (MgSO$_4$) and concentrate. Triturate the crude product in cold pentane to give 23.3 g of the pure product as a colorless powder.

Step 3: To [(CH$_3$)$_3$Sl]$_2$NNa (67.4 mL, 1.0M in THF) in THF (540 mL) at −78° C., add the product of step 2 (30.0 g, 67.4 mmol) as a solution in 120 mL THF dropwise over 30 min. Stir for 2 h, then, over 30 min, add 2-iodo-N-methoxy-N- methylacetamide (Prepare by stirring a solution of 2-chloro-N-methoxy-N- methylacetamide (10.58 g, 77.6 mmol) and NaI (11.9 g) in 190 mL acetone for 18 h in the dark. Remove the solvent in vacuo, add 300 mL THF and filter the suspension through a pad of Celite. Concentrate the filtrate and dissolve the crude in 80 mL THF.). Allow to warm to 23° C., adding 15 mL saturated NH$_4$Cl when the internal temperature reaches 0° C., then concentrate in vacuo. Add 750 mL CH$_2$Cl$_2$, 1.5 L Et$_2$O, and 750 mL water. Wash the organic layer with brine, dry over Na$_2$SO$_4$, and concentrate. Purify the crude product by filtration through a plug of silica gel using CH$_2$Cl$_2$/Et$_2$O/hexane (1:1:2) as eluent to give 32.4 g, 88% of the product as a viscous oil.

Step 4: Using a procedure similar to that of Example 1, treat the ketone of step 3 to obtain the corresponding oxime methyl ether in 80% yield.

Step 5: Treat a solution of the product of step 4 (2.02 g, 3.5 mmol) in THF (40 mL, −78° C.) with DIBAL (1M in hexane, 10 mL, 10 mmol) for 10 min. Quench the reaction mixture with sat'd. aq. Na$_2$SO$_4$(2 mL) and allow to warm to room temperature. Dilute the solution with Et$_2$O (750 mL), dry (Na$_2$SO$_4$) and concentrate to give the crude aldehyde as a colorless oil. The aldehyde is used immediately without any further purification.

Step 6: To a solution of the aidehyde from step 5 (184 mg, 0.36 mmol) in CF$_3$CH$_2$OH(2 mL) add 4-phenyl-4-piperidinyl acetamide (157 mg, 0.72 mmol), 3 A crushed molecular sieves, and NaBH$_3$CN (98 mg, 1.6 mmol). Stir the reaction mixture for 1 h, concentrate and purify by silica gel chromatography (eluent: $CH_2Cl_2$:$CH_3OH$:$NH_3$ aq. (20:1:0.1)) to give the Z isomer of the title compound as a colorless foam. HRMS (FAB, M+H$^+$): m/e calc'd for $[C_{34}H_{36}Cl_2F_6N_3O_3]^+$: 718.2038, found 718.2050.

Using the product of Step 5 and the appropriate amine in the procedure of Step 6, the following compounds are prepared:

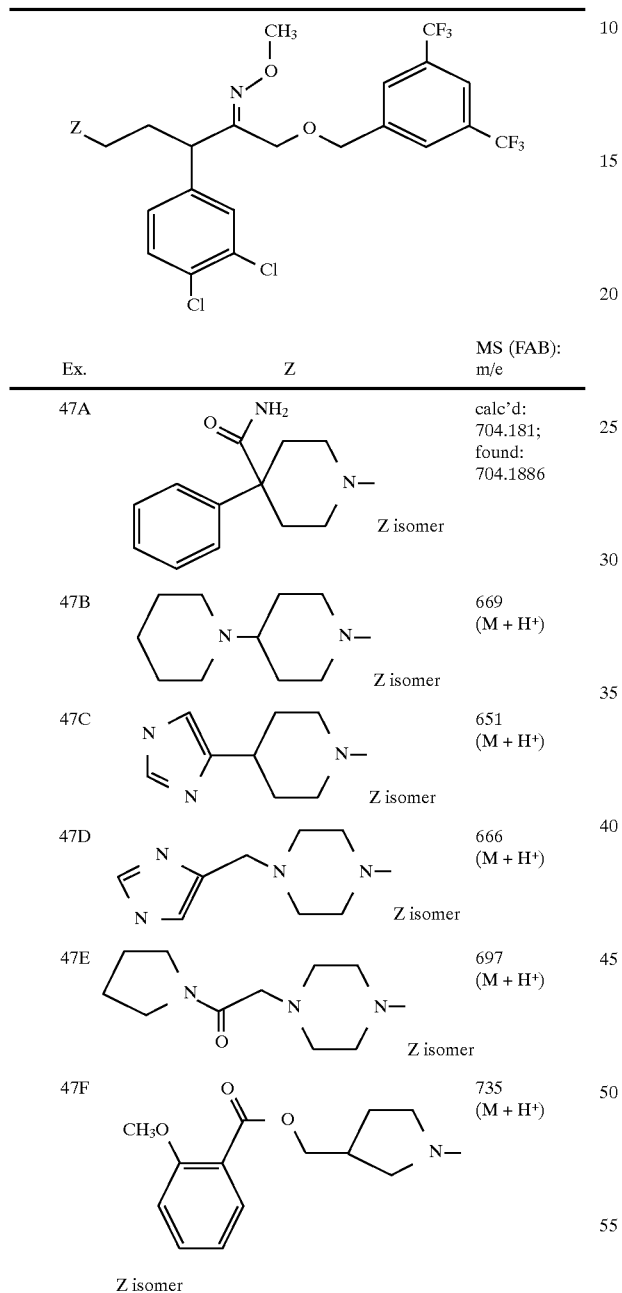

| Ex. | Z | MS (FAB): m/e |
|---|---|---|
| 47A | 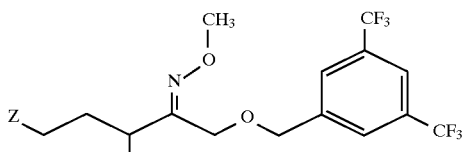 Z isomer | calc'd: 704.181; found: 704.1886 |
| 47B | Z isomer | 669 (M + H$^+$) |
| 47C | Z isomer | 651 (M + H$^+$) |
| 47D | Z isomer | 666 (M + H$^+$) |
| 47E | Z isomer | 697 (M + H$^+$) |
| 47F | Z isomer | 735 (M + H$^+$) |

-continued

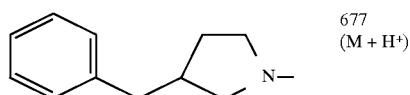

| Ex. | Z | MS (FAB): m/e |
|---|---|---|
| 47G | Z isomer, mixture or diastereomers | 677 (M + H$^+$) |
| 47H | 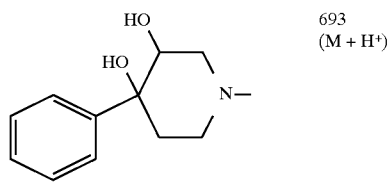 mixture of diastereomers | 693 (M + H$^+$) |
| 47I | 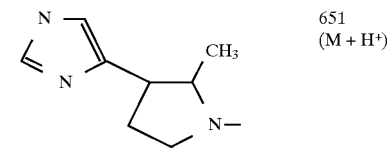 | 651 (M + H$^+$) |

EXAMPLE 48

Use the products of Preparations 10 and 11, and others prepared in a similar manner, in the procedure of Example 47 to obtain the following compounds:

| Ex. | Z | Q | Isomer | Physical Data |
|---|---|---|---|---|
| 48 | 4-hydroxy-4-phenylpiperidin-1-yl | 2-thienyl | Z | MS (Cl/CH4, M + H+): 614 |
| 48A | 4-hydroxy-4-phenylpiperidin-1-yl | 4-pyridyl | Z | MS (FAB M + H+): 610.2 |
| 48B | 4-hydroxy-4-phenylpiperidin-1-yl | 1-pyrrolyl | E/Z mixture | MS (FAB M + H+): 598.1 |
| 48C | 4-hydroxy-4-phenylpiperidin-1-yl | 2-pyrazinyl | Z | MS (FAB M + H+): 611.2 |
| 48D | 4-hydroxy-4-phenylpiperidin-1-yl | 2-naphthyl | Z | MS (FAB M + H+): 659.3 |
| 48E | 4-(2-oxo-2-pyrrolidin-1-yl-ethyl)piperazin-1-yl | 2-naphthyl | Z | MS (FAB M + H+): 679.3 |
| 48F | 4-((2-oxopyrrolidin-1-yl)methyl)piperidin-1-yl | 2-pyrazinyl | E/Z mixture | MS (FAB M + H+): 616.4 |
| 48G | 4-hydroxy-4-phenylpiperidin-1-yl | 3-pyridazinyl | E/Z mixture | MS (FAB M + H+): 611.0 |
| 48H | 4-hydroxy-4-phenylpiperidin-1-yl | 4-quinolinyl | Z | MS (FAB M + H+): 660.0 |

-continued

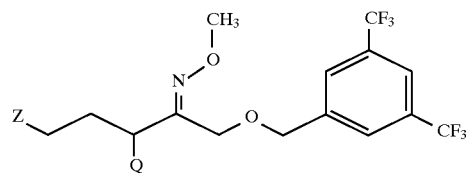

| Ex. | Z | Q | Isomer | Physical Data |
|---|---|---|---|---|
| 48I | (structure: N-acyl-piperidinyl with carbonyl) | 4-methylquinolinyl | Z | MS (FAB M + H+): 650.9 |
| 48J | (structure: 4-hydroxy-4-phenylpiperidinyl) | 3-methylisoxazolyl | E/Z mixture | MS (FAB M + H+): 614.0 |
| 48K | (structure: N-thioacyl-piperidinyl with C=S) | 3-methylisoxazolyl | E/Z mixture | MS (FAB M + H+): 605.0 |

EXAMPLE 49

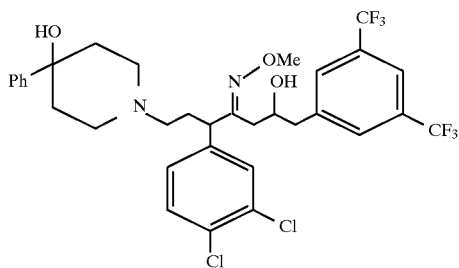

Step 1:

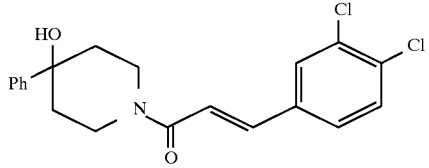

To a solution of 3,4-dichlorocinnamic acid (5.4 g, 20 mmoles), 4-hydroxy-4-phenylpiperidine (3.6 g, 20.3 mmoles) and Et$_3$N (3 mL) in dry THF (100 mL), add a THF suspension of EDCl (3.85 g, 20 mmoles in 30 mL dry THF). After 2 h, add water (100 mL) and extract the product into EtOAc (100 mL). Wash the organic phase with aqueous K$_2$CO$_3$ (50 mL) followed by 0.5M HCl (50 mL). Dry the organic phase (MgSO4) and remove the solvent under reduced pressure. The crude product crystallizes (7.5 g) on standing. HRMS (FAB, M+H$^+$): m/e calc'd for [C$_{20}$H$_{20}$NO$_2$Cl$_2$]$^+$: 376.0871, found 376.0856.

Step 2:

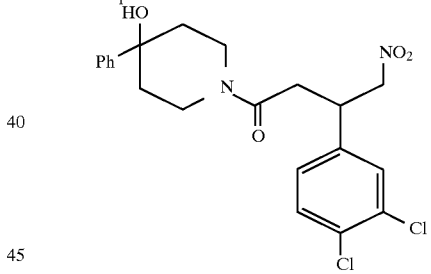

Treat a solution of the product of Step 1 (0.5 g, 1.37 mmoles) in CH$_3$NO$_2$ (10 mL) with 1 mL of Triton B (40% benzyltrimethylammonium hydroxide in CH$_3$OH). Heat the stirred solution to reflux for 3.5 h. Cool the mixture, neutralize with 1M HCl and dilute with water (30 mL). Extract the product into EtOAc (2×30 mL), dry (MgSO$_4$) and concentrate to an oil. Purify by silica gel chromatography (eluant: EtOAC/Hexane (1:1 to 2:1)) to obtain 0.309 9 of the title compound and 0.160 g starting material. HRMS (FAB, M+H$^+$): m/e calc'd for [C$_{21}$H$_{23}$N$_2$O$_4$Cl$_2$]$^+$: 437.1035, found 437.1023.

Step 3:

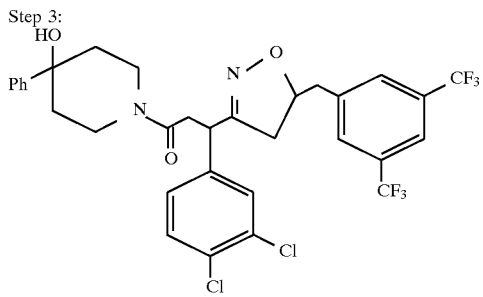

Step 3a: Treat a solution of 3,5-bis(trifluoromethyl) bromobenzene (45.87 g, 0.156 moles) in degassed toluene (300 mL) with allyltributyltin (54.47 g, 0.164 moles) and $[(C_6H_5)_3P]_4Pt$ (1.8 g, 1.44 mmoles) and reflux for 24 h. Distill the toluene at atmospheric pressure and distill the residue under reduced pressure (10 mm Hg) at 90°–100° C. to afford 23.89 g of the title compound. B.p.: 92°–97° C. at 10 mm Hg. MS (Cl, M+H$^+$), m/e 255.

Step 3: Treat a THF solution (15 mL) of a mixture of the products of Step 2 (1.8 g, 4.1 mmoles) and Step 3a (2.2 g, 8.6 mmoles) with $C_6H_5NCO$ (1.67 g, 14 mmoles), followed by four drops (~0.05 g) of dry $Et_3N$ and stir the mixture for 20 h at room temperature under $N_2$. Dilute with hexane (5 mL) and filter to remove solids. Concentrate the filtrate to an oil and purify by flash silica gel chromatography (eluant: EtOAc/hexane 1:1) to give the two diastereoisomers of the title compound (total yield: 1.3 g): diastereoisomer A: 0.8 g; diastereoisomer B: 0.5 g. Diastereoisomer A: HRMS (FAB, M+H$^+$): m/e calc'd for $[C_{32}H_{29}N_2O_3Cl_2F_6]^+$: 673.1459, found 673.1462; M.P. 80°–85° C. Diastereoisomer B: HRMS FAB, M+H$^+$): m/e calc'd for $[C_{32}H_{29}N_2O_3Cl_2F_6]^+$: 673.1459, found 673.1455; M.P. 85°–88° C.

Step 4:

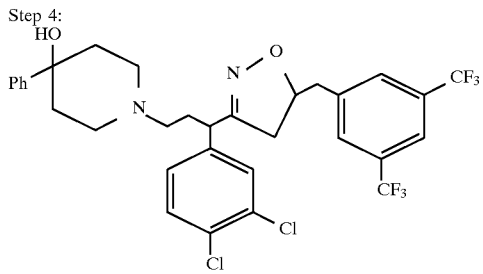

Treat a cold (5° C.), stirred solution of the product of Step 3 (2.02 g, 3 mmoles in 50 mL of dry THF) under $N_2$ with neat 10M $(CH_3)_2S \cdot BH_3$ (0.5 mL). Heat at reflux for 3 h, cool to room temperature and quench the reaction with 1N HCl (5 mL). Evaporate the solvent with warming under reduced pressure, treat the mixture with 50 mL of $CH_3OH$ and 2 g of $K_2CO_3$, stir with heating at reflux for 6 h. Cool the mixture, dilute with water (75 mL) and extract the product into $CH_2Cl_2$ (2×50). Wash the organic layer with water (2×30 mL), dry (MgSO$_4$) and remove the solvent under vacuum. Purify the residue by silica gel flash chromatography (eluant: EtOAc/hexane/$CH_3OH$, 4:5:1 to 6:3:1) to afford 0.330 g of diastereoisomer A and 0.180 g diastereoisomer B. Diastereoisomer A: HRMS (FAB, M+H$^+$): m/e calc'd for $[C_{32}H_{31}N_2O_2Cl_2F_6]^+$: 659.1667, found 659.1665 Diastereoisomer B: HRMS (FAB, M+H$^+$): m/e calc'd for $[C_{32}H_{31}N_2O_2Cl_2F_6]^+$: 659.1667, found 659.1665.

Step 5:

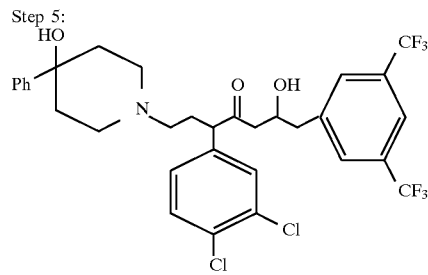

Wash Raney Nickel (0.3 g, 50% aqueous suspension) with EtOH (4×5 mL), add EtOH (15 mL), glacial HOAC (0.250 g) and the the product of Step 4 (diastereoisomer A, 0.3 g, 0.45 mmoles), degas and evacuate the mixture under vacuum. Introduce an atmosphere of $H_2$ gas and stir the mixture vigorously overnight at room temperature. Purge the mixture with $N_2$, filter through celite and concentrate under vacuum. Pass the residue through a pad of silica gel, eluting with EtOAc, and concentrate to an oil to afford 0.206 g of the title compound as a mixture of diastereoisomers. HRMS (FAB, M+H$^+$): m/e calc'd for $[C_{32}H_{32}NO_3Cl_2F_6]^+$: 648.1496, found 648.1507.

Step 6: Treat a solution of the product of Step 5 (0.25 g, 0.37 mmoles) in $CH_3OH$ (2 mL) and pyridine (3 mL) with $CH_3ONH_2$ HCl (0.50 gms, 0.71 mmoles) and heat at reflux for 3 h. Evaporate the solvent and dissolve the residue in EtOAc (5 mL), wash with water, dry (MgSO$_4$) and concentrate to afford 0.106 g of a mixture of diastereoisomers. HRMS (FAB, M+H$^+$): m/e calc'd for $[C_{33}H_{33}N_2O_3Cl_2F_6]^+$: 691.1929, found 691.1938.

EXAMPLES 50 to 56

Using the procedures described below, compounds of the following formula were prepared, wherein the variables are as defined inthe table:

| Ex. | A | $-\begin{pmatrix}R^6\\|\\C\\|\\R^7\end{pmatrix}_d - X - \begin{pmatrix}R^9\\|\\C\\|\\R^8\end{pmatrix}_b -$ | HRMS (FAB, M + H$^+$): m/e calc'd | HRMS (FAB, M + H$^+$): m/e found |
|---|---|---|---|---|
| 50 | =NOCH$_3$ | —CH$_2$C(O)CH$_2$— | 689.1772 | 689.1765 |
| 51 | =NOCH$_3$ | —CH$_2$C(=NOH)CH$_2$— | 704.1881 | 704.1889 |
| 52 | =NOCH$_3$ | —CH$_2$C(=NOCH$_3$)CH$_2$— | 718.2038 | 718.2051 |
| 53 | =NOH | —C(O)CH$_2$CH$_2$— | 675.1616 | 675.1594 |
| 54 | =NOCH$_3$ | —C(O)CH$_2$CH$_2$— | 689.1772 | 689.1775 |
| 55 | =NH | —NHCH$_2$CH$_2$— | 686.1827 | 686.1840 |
| 56 | =NOH | —NHCH$_2$— | 688.1619 | 688.1626 |

EXAMPLE 50

Treat a cold (−5° C.) acetone (10 mL) solution of the productof Example 49 (0.3 g, 0.433 mmoles) with 0.8 mL of freshly prepared Jones reagent (CrO$_3$, H$_2$SO$_4$). Stir for 15 min and neutralize to pH 8 with 2 mL of saturated aqueous NaHCO₃ diluted with 15 mL of water. Extract the product with CH₂Cl₂ (2×10 mL), dry (MgSO₄) and remove the solvent by vacuum distillation to give a light brown solid (0.3 g). Purify the product by preparative silica gel TLC (CH₂Cl₂/CH₃OH/NH₄OH, 9:1:0.6) to give a yellow gummy solid (0.14 g).

EXAMPLE 51

Treat a mixture of the product of Example 50 (0.06 g, 0.087 mmoles), HONH₂·HCl (0.03 g, 0.43 mmoles) with pyridine (0.3 mL) in CH₃OH (0.5 mL) and reflux with stirring under an inert atmosphere for 4 h. Cool the reaction mixture to room temperature, dilute with water (5 mL) and extract the product into EtOAc (2×5 mL). Wash the organic phase with water (2×5 mL), dry (MgSO₄) and concentrate under reduced pressure to an oil. Purify the product by preparative silica gel TLC (eluant: EtOAc/hexane, 2:1) to afford the title compound as a white solid (0.032 g). M.p.: 55°–60° C.

EXAMPLE 52

Treat a mixture of the product of Example 50 (0.04 g, 0.0578 mmoles) with CH₃ONH₂·HCl (0.024 g, 0.29 mmoles) in a manner similar to that describd in Example 51 to afford the title compound as a yellow gum (0.02 g).

EXAMPLE 53

Step 1:

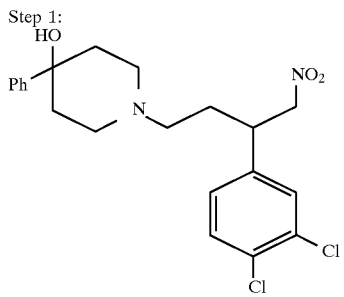

Treat a 25 mL THF solution the product of Example 1, Step 2 (1.3 g, 2.97 mmoles) with 10M (CH₃)₂S·BH₃ (0.9 mL, 9 mmoles) with stirring under N₂. Heat the mixture to reflux for 2 h, cool to 5° C. and quench the reaction with 1.5M H₂SO₄. Dilute the mixture with 30 mL of water and extract the product into EtOAc (2×30 mL). Dry the organic layer (MgSO₄) and concentrate to dryness to afford a white solid. Take up the residue in CH₃OH (40 mL) and add solid K₂CO₃ (1 gm). Heat the mixture to reflux for 2 h, cool, filter through celite and concentrate to ⅓ the original volume. Dilute the mixture with water (25 mL), extract into EtOAc (2×30 mL), wash the organic layer with water (2×25 ml), dry and remove the solvent under vacuum to afford 1.06 g of the title compound. MS(Cl, M+H⁺), m/e 423.

Step 2: Treat a suspension of potassium tert-butoxide in 5 mL of DMSO with a solution of the product of Step 1 (0.4 gm, 0.944 mmoles in 10 mL of DMSO). Stir at room temperature for 30 min, then treat with a solution of the product of Preparation 12 (1.369 g, 3.78 mmoles) in DMSO (10 mL). Stir the mixture at room temperature overnight under an inert atmosphere. Dilute the mixture with water (25 mL) and extract with EtOAc. Wash the organic phase with water (2×25 mL), dry and concentrate under reduced pressure to give a semisolid. Triturate the solid with Et₂O and filter to give a light yellow solid (0.56 g). Recrystallize from CH₂Cl₂ to give 0.36 g of a white solid. M.p. 145°–150°

Step 3: Treat the product of Step 2 (0.25 g, 0.36 mmoles) in 5 mL of CH₃CN with Et₃N (0.5 g, 0.5 mmoles) and CS₂ (0.4 g, 5 mmoles). Heat the reaction to 50° C. for 5 h. Remove solvent and excess volitiles by vacuum distillation and purify the product by preparative TLC (eluant, EtOAc/hexane/CH₃OH, 5:4:1) to give the title compound (0.147 g).

EXAMPLE 54

Treat a solution of the product of Example 53 (0.05 g, 0.074 mmoles) in THF (1 mL) with a suspension of NaH (3.2 mg of a 60% dispersion in mineral oil, from which oil is removed by washing with 0.5 mL of hexane, 0.08 mmoles NaH) in THF (0.5 mL) at room temperature for 30 min with stirring under an inert atmosphere. Cool the mixture to −70° C.and treat with an 0.2M solution of CH₃I in THF (0.4 mL, 0.08 mmoles). Gradually warm the mixture to 10° C. Add water (2 ml) and extract the product into EtOAc (5 mL), dry (MgSO₄) and concentrate under reduced pressure to give a yellow solid. Purify the product by preparative silica gel TLC (EtOAc/hexane, 2:1) to afford the title compound (0.012 g).

EXAMPLE 55

Step 1: Treat a solution (5 mL) of the product of Example 53, Step 1 (0.24 g, 0.56 mmoles) in CH₃CN (5 mL) with Et₃N (0.6 mL). Stir for 10 min at room temperature, add neat CS₂, stir the mixture under N₂ overnight and then heat to 70° C. for 1 h. Remove solvent and excess volitiles by vacuum distillation and the purify the product by preparative silica gel TLC (EtOAc/hexane, EtOAc/hexane 6:4, then CH₃OH/EtOAc/hexane 1:5:5) to afford 0.132 gm of the title compound. MS(Cl, M+H⁺), m/e 389.

Step 2: Treat a solution of the product of Step 1 (0.201 g, 0.516 mmoles in 2 mL of CH₂Cl₂) with a solution of Al(CH₃)₃ in hexane (0.26 mL of 2M Al(CH₃)₃ in hexane). In a separate flask, treat a solution of of the product of Preparation 13 (0.167 g, 0.568 mmoles in 2 mL of CH₂Cl₂) with Al(CH₃)₃ (0.284 mL of 2M Al(CH₃)₃) and mix thoroughly. After 20 min, mix the two solutions and warm the resulting mixture to 70° C. overnight with stirring under N₂. Dilute the reaction mixture with EtOAc (5mL) and treat with 0.2M HCl (5 mL) with thorough mixing. Wash the EtOAc layer with water, dry (MgSO₄) and concentrate to an oil. Purify the product by preparative silica gel TLC (eluant: EtOAc/Hexane/CH₃OH, 5:4:1) to afford 0.0135 g of the title compound.

EXAMPLE 56

Step 1: Treat the product of Example 55, Step 1 (0.33 g, 0.85 mmoles) in 6 mL of a mixture of CH₃OH and pyridine (5:1) with HONH₂ HCl (0.08g, 1.1 mmoles) and heat for 1 h at reflux with stirring under N₂. Cool the mixture to room temperature and remove the solvent by vacuum distillation. Purify the residue by preparative silica gel TLC (eluant: EtOAc/hexane, 2:1) to obtain a white solid (0.350 gm). HRMS (FAB, M+H⁺): m/e calc'd for $[C_{21}H_{26}N_3O_2Cl_2]^+$: 422.1402, found 422.1404.

Step 2: Treat the product of Step 1 (0.1 g, 0.24 mmoles) in dry pyridine (1.5 mL) at 0° C. with 3,5-bis (trifluoromethyl)benzoyl chloride (0.07 gm, 0.25 mmoles) with stirring under N₂. Warm the reaction to room temperature over ½ h, then heat at 80° C. for 1 h. Remove the solvent by vacuum distillation and purify the product by preparative silica gel TLC (EtOAc/hexane 1:1) to afford a clear glassy solid (0.127 g). MS(Cl, M+H³⁰), m/e 611.

Step 3: Treat a solution of the product of Step 3 (0.1 g, 0.155 mmoles in 3 mL of Et₂O) with three portions (50 mgs each) solid LiAlH$_4$. Stir the mixture under N$_2$ for 1 h at room temperature and then carefully quench with a mixture of CH$_3$OH and 3M NaOH (1:1, 2 mL). Remove solids by filtration through celite and remove solvent by vacuum distillation to afford a gummy residue. Purify the product by preparative silica gel TLC (eluant, EtOAc/hexane/CH$_3$OH, 8:1:1) to afford the title compound as a glassy solid (0.27 g).

The following formulations exemplify some of the dosage forms of this invention. In each, the term "active compound" refers to a ound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLES B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
|   | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE C

Sterile Powder for Injection

| Ingredient | mg/vial | mg/vial |
|---|---|---|
| Active sterile powder | 100 | 500 |

For reconstitution add sterile water for injection or bacteriostatic water for injection.

The in vitro and in vivo activity of the compounds of formula I can be determined by the following procedures.

In Vitro Procedure to Identify NK$_1$ Activity

Test compounds are evaluated for their ability to inhibit the activity of the NK$_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% O$_2$ and 5% CO$_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P inhibits the electrical field stimulated-induced contractions of the guinea pig vas deferens. In unpaired studies, all tissues (control or drug treated) are exposed to cumulative concentrations of Substance P ($1 \times 10^{-10}$ M-$7 \times 10^{-7}$ M). Single log-concentrations of the test compounds are given to separate tissues and allowed to equilibrate for 30 minutes before a Substance P concentation-response curve is generated. At least 5 separate tissues are used for each control and individual drug-concentration for every drug assay.

Inhibition of the Substance P is demonstrated by a rightward shift of its concentration-response curve. These shifts are used to determine the pA$_2$ value, which is defined as the negative log of the molar concentration of the inhibitor which would require that twice as much agonist be used to elicit a chosen response. This value is used to determine relative antagonist potency.

Isolated Hamster Trachea NK$_2$ Assay

General methodology and characterization of hamster trachea responses to neurokinin agonists as providing an NK$_2$ monoreceptor assay is found in C. A. Maggi, et al., *Eur. J. Pharmacol* 166 (1989) 435 and J. L. Ellis, et al., *J. Pharm. Exp. Ther.* 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoractomy and cutting the heart. Cervical trachea segments are removed to room temperature Krebs buffer, pH 7.4, aerated with 95% O$_2$-5% CO$_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6–0 silk. Baths are filled with Krebs buffer, pH 7.4, maintained at 37° C. and continuously aerated with 95% O2–5% CO$_2$ gas. Tracheal rings are placed under 1.0 g initial tension and allowed a 90 min equilibration period with four 1 $\mu$M NKA challenge, wash and recovery cycles at 20 min intervals. 30 min vehicle pretreatment is followed by cumulative additions of rising doses of NKA (3 nM-1 $\mu$M final concentration, 5 min intervals between additions). The final NKA response is followed by a 15 min wash and recovery period. 30 min pretreatment with a test compound or its vehicle is followed by cumulative additions of rising doses of NKA (3 nM-10$\mu$M final concentration if necessary, 5 min intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio $\geq 2$ at a screening concentration of 1 μM (i.e. $pA_{2} \geq =6.0$) are considered actives. Further dose response data is obtained for actives so that an apparent $pA_2$ estimate can be calculated. $pA_2$ is calculated either by estimation of $K_i$ as described by Furchgott (where $pA_2$=-Log $K_i$, R. F. Furchgott, *Pharm. Rev.* 7 [1995] 183) or by Shild Plot Analysis (O. Arunlakshana & H. O. Shild, *Br. J. Pharmacol.* 14[1959] 48) if the data is sufficient.

Effect of $NK_1$ Antagonists on Substance P-Induced Airway Microvascular Leakage in Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated ($V_T$=4 ml, f=45 breaths/min) with a Harvard rodent respirator. The jugular vein is cannulated for the injection of drugs.

The Evans blue dye technique (Danko, G. et al., *Pharmacol. Commun.*, 1, 203–209, 1992) is used to measure airway microvascular leakage (AML). Evans blue (30 mg/kg) is injected intravenously, followed 1 min later by i.v. injection of substance P (10 μg/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 μg/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge CA, model MP45-1, range ±2 cmH$_2$O) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, CA, model MP45-1, range ±20 cm H$_2$O). The volume, airflow and transpulmonary pressure signals are monitored by means of a pulmonary analysis computer (Buxco Electronics, Sharon, CT, model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 μg/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L100$) or decreased $C_{Dyn}$ by 40% ($C^{Dyn}40$) from baseline values are obtained by log-linear interpolation of the dose response curves.

Neurokinin Receptor Binding Assay(s)

Chinese Hamster ovary (CHO) cells transfected with the coding regions for the human neurokinin 1 (NK1) of the human neurokinin 2 (NK2) receptors are grown in Dulbecco's minimal essential medium supplemented with 10% fetal calf serum, 0.1 mM non-essential amino acids, 2 mM glutamine, 100units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMl media at 40° C. for 5 minutes. The pellet is resuspended inTris-HCl (pH7.4) containing 1 uM phsphoramidon and 4 ug/ml of chymostatin at a cell density of $30 \times 10^6$ cells/ml. The suspension is then homogenized in a Brinkman Polytron (setting 5) for 30–45 seconds. The homogenate is centrifuged at 800×g for 5 min at 4° C. to collect unbroken cells and nuclei. The supernatant is centrifuged in a Sorvall RC5C at 19,000 rpm (44,00×g) for 30 min at 4° C. The pellet is resuspended, an aliquot is removed for a protein determination (BCA) and washed again. The resulting pellet is stored at –80° C.

To assay receptor binding, 50 μl of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/mmole) (Zenca) (1.0 nM for the NK-2 assay) is added to tubes containing buffer (50 mM Tris-HCl (pH 7.4) with 1 mM MnCl$_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethylenimine. Filters are washed 2 times with 3 ml of 50 mM Tris-HCl (pH7.4). Filters are added to 6 mls of Ready-Safe liquid scintillation cocktail and quantified by liquid scintillation spectrometry in a LKB 1219 RackBeta counter. Non-specific binding is determined by the addition of either 1 μM of CP-99994 (NK-1) or 1 μM SR-48968 (NK-2) (both synthesized by the chemistry department of Schering-Plough Research Institute). $IC_{50}$ values are determined from competition binding curves and Ki values are determined according to Cheng and Prusoff using the experimentally determined value of 0.8 nM for the NK-1 receptor and 2.4 nM for the NK-2 receptor.

$NK_3$ activity is determined by following a procedure similar to that described in the literature, e.g., *Molecular PharmacoL,* 48 (1995), p. 711–716.

% Inhibition is the difference between the percent of maximum specific binding (MSB) and 100%. The percent of MSB is defined by the following equation, wherein "dpm" is disintegrations per minute:

$$\% MSB = \frac{(dpm \text{ of unknown}) - (dpm \text{ of nonspecific binding})}{(dpm \text{ of total binding}) - (dpm \text{ of nonspecific binding})} \times 100$$

It will be recognized that compounds of formula I exhibit $NK_1$, $NK_2$ and/or $NK_3$ antagonist activity to varying degrees, e.g., certain compounds have strong $NK_1$ antagonist activity, but weaker $NK_2$ and $NK_3$ antagonist activity, while others are strong $NK_2$ antagonists, but weaker $NK_1$ and $NK_3$ antagonists. While compounds with approximate equipotency are preferred, it is also within the scope of this invention touse compounds of with unequal $NK_1/NK_2/NK_3$ antagonist activity when clinically appropriate.

Using the test procedures described above, the following data (% inhibition or Ki) were obtained for preferred and/or representative of formula I:

| Ex. | % Inhibition $NK_1$ (1 µM dose) | Ki ($NK_1$) (nM) | % Inhibition $NK_2$ (1 µM dose) | Ki ($NK_2$) (nM) | Ki ($NK_3$) (nM) |
|---|---|---|---|---|---|
| 1 | 88.0 | 25 | 95.0 | 20 | 109 |
| 1C | 44.0 | — | 16.0 | — | — |
| 2 | 69.0 | 40 | 17.0 | — | — |
| 7 | 69.0 | 121 | 13.0 | — | — |
| 22AK | 67 | 132 | 95 | 2.0 | — |
| 22AL | 12.0 | — | 100 | 2.0 | — |
| 35C | 93 | 2.0 | 0.0 | — | — |
| 39F | 93 | 4.3 | 96 | 12.0 | — |
| 42L | 91 | 4.6 | 86 | 123.0 | — |

Compounds of the present invention exhibit a range ofactivity: percent inhibition at a dosage of 1 µM ranges from about 0 to about 100% inhibition of $NK_1$ and/or about 0to about 100% inhibition of $NK_2$. Preferred are compounds having a Ki≦100 nM for the $NK_1$ receptor. Also preferred are compounds having a Ki≦100 nM for the $NK_2$ receptor. Another group of preferred compounds are those having a Ki≦100 nM for each of the $NK_1$and $NK_2$ receptors.

We claim:

1. A compound represented by the structural formula

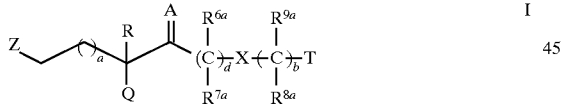

or a pharmaceutically acceptable salt thereof, wherein:
  a is 0, 1, 2 or 3;
  b and d are independently 0, 1 or 2;
  R is H, $C_{1-6}$ alkyl, —$OR^6$ or $C_2$–$C_6$ hydroxyalkyl;
  A is =N—$OR^1$, =N—N($R^2$)($R^3$), =C($R^{11}$)($R^{12}$) or =$NR^{25}$;
  X is a bond, —C(O)—, —O—, —$NR^6$—, —S(O)$_e$—, —N($R^6$)C(O)—, —C(O)N($R^6$)— —OC(O)$NR^6$—, —OC(=S)N$R^6$—, —N($R^6$)C(=S)O—, —C(=$NOR^1$)—, —S(O)$_2$N($R^6$)—, —N($R^6$)S(O)$_2$—, —N($R^6$)C(O)O— or —OC(O)—, provided that when d is 0, X is a bond, —C(O)—, —$NR^6$—, —C(O)N ($R^6$)—, —N($R^6$)C(O)—, —OC(O)N$R^6$—, —C(=$NOR^1$)—, —N($R^6$)C(=S)O—, —OC(=S) $NR^6$—, —N($R^6$)S(O)$_2$— or —N($R^6$)C(O)O—; provided that when A is =C($R^{11}$)($R^{12}$) and d is 0, X is not —$NR^6$— or —N($R^6$)C(O)—; and provided that when A is =$NR^{25}$, d is 0 and X is —$NR^6$— or —N($R^6$)C (O)—;

T is H, $R^4$-aryl, $R^4$-heterocycloalkyl, $R^4$-heteroaryl, phthalimidyl, $R^4$-cycloalkyl or $R^{10}$-bridged cycloalkyl;

Q is $R^5$-phenyl, $R^5$-naphthyl, —$SR^6$, —N($R^6$)($R^7$), or —$OR^6$ [or $R^5$-heteroaryl], provided that when Q is —$SR^6$, —N($R^6$)($R^7$) or —$OR^6$, R is not —$OR^6$;

$R^1$ is H, $C_{1-6}$ alkyl, —(C($R^6$)($R^7$))$_n$—G, —$G^2$, —(C($R^6$) ($R^7$))$_p$—M— (C($R^{13}$)($R^{14}$))$_n$—(C($R^8$)($R^9$))$_u$—G, —C(O)N($R^6$)—(C($R^{13}$)($R^{14}$))$_n$—(C($R^8$)($R^9$))$_u$—G or —(C($R^6$)($R^7$))$_p$—M—($R^4$-heteroaryl);

$R^2$ and $R^3$ are independently selected from the group consisting of H, $C_{1-6}$ alkyl, —CN, —(C($R^6$)($R^7$))$_n$—G, —$G^2$, —C(O)—(C($R^8$)($R^9$))$_n$—G and —S(O)$_e R^{13}$; or $R^2$ and $R^3$, together with the nitrogen to which they are attached, form a ring of 5 to 6 members, wherein 0, 1 or 2 ring members are selected from the group consisting of —O—, —S— and —N($R^{19}$)—;

$R^4$ and $R^5$ are independently 1–3 substituents independently selected from the group consisting of H, halogeno, —$OR^6$, —OC(O)$R^6$, —OC(O)N($R^6$)($R^7$), —N($R^6$)($R^7$), $C_{1-6}$ alkyl, —$CF_3$, —$C_2F_5$, —$COR^6$, —$CO_2R^6$, —CON($R^6$)($R^7$), —S(O)$_e R^{13}$, —CN, —$OCF_3$, —$NR^6 CO_2 R^{16}$, —$NR^6 COR^7$, —$NR^8 CON$ ($R^6$)($R^7$), $R^{15}$-phenyl, $R^{15}$-benzyl, $NO_2$, —N($R^6$)S(O)$_2$ $R^{13}$ or —S(O)$_2$N($R^6$)($R^7$); or adjacent $R^4$ substituents or adjacent $R^5$ substituents can form a —O—$CH_2$—O— group; and $R^4$ can also be $R^{15}$-heteroaryl;

$R^6$, $R^7$, $R^8$, $R^{6a}$, $R^{7a}$, $R^{8a}$, $R^{13}$ and $R^{14}$ are independently selected from the group consisting of H, $C_{1-6}$ alkyl, $C_2$–$C_6$ hydroxyalkyl, $C_1$–$C_6$ alkoxy-$C_1$–$C_6$ alkyl, $R^{15}$-phenyl, and $R^{15}$-benzyl; or $R^6$ and $R^7$, together with the nitrogen to which they are attached, form a ring of 5 to 6 members, wherein 0, 1 or 2 ring members are selected from the group consisting of —O—, —S— and —N($R^{19}$)—;

$R^9$ and $R^{9a}$ are independently selected from the group consisting of $R^6$ and —$OR^6$ $R^{10}$ and $R^{10a}$ are independently selected from the group consisting of H and $C_{1-6}$ alkyl;

$R^{11}$ and $R^{12}$ are independently selected from the group consisting of H, $C_1$–$C_6$ alkyl, —$CO_2R^6$, —$OR^6$, —C(O)N($R^6$)($R^7$), $C_1$–$C_6$ hydroxyalkyl, —(CH$_2$)$_r$—OC(O)$R^6$, —(CH$_2$)$_r$—OC(O)CH=$CH_2$, —(CH$_2$)$_r$—O (CH$_2$)$_s$—$CO_2R^6$, —(CH$_2$)$_r$—O—(CH$_2$)$_s$—C(O)N($R^6$) ($R^7$) and —(CH$_2$)$_r$—N($R^6$)($R^7$);

$R^{15}$ is 1 to 3 substituents independently selected from the group consisting of H, $C_1$–$C_6$ alkyl, $C_1$–$C_6$ alkoxy, $C_1$–$C_6$ alkylthio, halogeno, —$CF_3$, —$C_2F_5$, —$COR^{10}$, —$CO_2R^{10}$, —C(O)N($R^{10}$)$_2$, —S(O)$_e R^{10a}$, —CN, —N($R^{10}$)$COR^{10}$, —N($R^{10}$)CON($R^{10}$)$_2$ and —$NO_2$;

$R^{16}$ is $C_{1-6}$ alkyl, $R^{15}$-phenyl or $R^{15}$-benzyl;

$R^{19}$ is H, $C_1$–$C_6$ alkyl, —C(O)N($R^{10}$)$_2$, —$CO_2R^{10}$, —(C ($R^8$)($R^9$))$_f$—$CO_2R^{10}$ or —(C($R^8$)($R^9$))$_u$—C(O)N ($R^{10}$)$_2$;

f, n, p, r and s are independently 1–6;
u is 0–6;
G is selected from the group consisting of H, $R^4$-aryl, $R^4$-hetero-cycloalkyl, $R^4$-heteroaryl, $R^4$-cycloalkyl, —$OR^6$, —N($R^6$)($R^7$), —$COR^6$, —$CO_2R^6$, —CON($R^7$) ($R^9$), —S(O)$_e R^{13}$, —$NR^6 CO_2 R^{16}$, —$NR^6 COR^7$, —$NR^8 CON$($R^6$)($R^7$), —N($R^6$)S(O)$_2 R^{13}$, —S(O)$_2$N ($R^6$)($R^7$), —OC(O)$R^6$, —OC(O)N($R^6$)($R^7$), —C(=$NOR^8$)N($R^6$)($R^7$), —C(=$NR^{25}$)N($R^6$)($R^7$), —N($R^8$)C(=$NR^{25}$)N($R^6$)($R^7$), —CN, —C(O)N($R^6$) $OR^7$, and —C(O)N($R^9$)—($R^4$-heteroaryl), provided that when n is 1 and u is 0, or when $R^9$ is —$OR^6$, G is not —OH or —N($R^6$)($R^7$);

117

M is selected from the group consisting of a double bond, —O—, —N($R^6$)—, —C(O)—, —C($R^6$)($OR^7$)—, —C($R^8$)(N($R^6$)($R^7$))—, —C(=NO$R^6$)N($R^7$)—, —C(N($R^6$)($R^7$))=NO—, —C(=N$R^{25}$)N($R^6$)—, —C(O)N($R^9$)—, —N($R^9$)C(O)—, —C(=S)N($R^9$)—, —N($R^9$)C(=S)— and —N($R^6$)C(O)N($R^7$)—, provided that when n is 1, G is not OH or —NH($R^6$); and when p is 2–6, M can also be —N($R^6$)C(=N$R^{25}$)N($R^7$)— or —OC(O)N($R^6$)—;

$G^2$ is $R^4$-aryl, $R^4$-heterocycloalkyl, $R^4$-heteroaryl, $R^4$-cycloalkyl, —CO$R^6$, —CO$_2R^{16}$, —S(O)$_2$N($R^6$)($R^7$) or —CON($R^6$)($R^7$);

e is 0, 1 or 2, provided that when e is 1 or 2, $R^{13}$ and $R^{10a}$ are not H;

$R^{25}$ is H, $C_1$–$C_6$ alkyl, —CN, $R^{15}$-phenyl or $R^{15}$-benzyl;

Z is

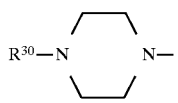

or morpholinyl;

g and j are independently 0–3;

h and k are independently 1–4, provided the sum of h and g is 1–7;

J is two hydrogen atoms, =O, =S, =N$R^9$ or =NO$R^1$;

L and $L^1$ are independently selected from the group consisting of H, $C_1$–$C_6$ alkyl, $C_1$–$C_6$ alkenyl, —CH$_2$-cycloalkyl, $R^{15}$-benzyl, $R^{15}$-heteroaryl, —C(O) $R^6$, —(CH$_2$)m—O$R^6$, —(CH$_2$)$_m$—N($R^6$)($R^7$), —(CH$_2$)$_m$—C(O)—O$R^6$ and —(CH$_2$)$_m$—C(O)N($R^6$)($R^7$);

m is 0 to 4, provided that when j is 0, m is 1–4;

$R^{26}$ and $R^{27}$ are independently selected from the group consisting of H, $C_1$–$C_6$ alkyl, $R^4$-aryl and $R^4$-heteroaryl; or $R^{26}$ is H, $C_1$–$C_6$ alkyl, $R^4$-aryl or $R^4$-heteroaryl, and $R^{27}$ is —C(O)$R^6$, —C(O)—N($R^6$)($R^7$), —C(O)($R^4$-aryl), —C(O)($R^4$-heteroaryl), —SO$_2R^{13}$ or —SO$_2$—($R^4$-aryl);

$R^{28}$ is H, —(C($R^6$)($R^{19}$))$_t$—G, —(C($R^6$)($R^7$))$_v$—$G^2$ or —NO$_2$;

t and v are 0, 1, 2 or 3, provided that when j is 0, t is 1, 2 or 3;

$R^{29}$ is H, $C_1$–$C_6$ alkyl, —C($R^{10}$)$_2$S(O)$_eR^6$, $R^4$-phenyl or $R^4$-heteroaryl;

$R^{30}$ is H, $C_1$–$C_6$ alkyl, $R^4$-cycloalkyl, —(C($R^{10}$)$_2$)$_w$—($R^4$-phenyl), —(C($R^{10}$)$_2$)$_w$-($R^4$-heteroaryl), —C(O)$R^6$, —C(O)O$R^6$, —C(O)N($R^6$)($R^7$),

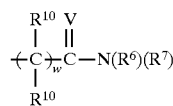

or

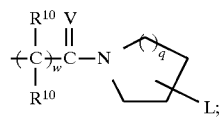

w is 0, 1, 2, or 3;

V is =O, =S or =N$R^6$; and

118 q is 0–4.

2. A compound of claim 1 wherein X is —O—, —C(O)—, a bond, —N$R^6$—, —S(O)$_e$—, —N($R^6$)C(O)—, —C(O)N$R^6$, —OC(O)N$R^{6-}$ or —C(=NO$R^1$)—.

3. A compound of claim 1 wherein Q is $R^5$-phenyl, or $R^5$-naphthyl.

4. A compound of claim 1 wherein $R^{6a}$, $R^{7a}$, $R^{8a}$ and $R^{9a}$ are independently selected from the group consisting of H, hydroxyalkyl and alkoxyalkyl.

5. A compound of claim 1 wherein X is —O—, —C(O)—, a bond, —N$R^6$—, —S(O)$_e$—, —N($R^6$)C(O)—, —C(O)N$R^6$, —OC(O)N$R^{6-}$ or —C(=NO$R^1$)—; T is $R^4$-aryl, $R^4$-heteroaryl, $R^4$-cycloalkyl or $R^{10}$-bridged cycloalkyl; Q is $R^5$-phenyl, or $R^5$-naphthyl; $R^{6a}$, $R^{7a}$, $R^{8a}$ and $R^{9a}$ are independently selected from the group consisting of H, hydroxyalkyl and alkoxyalkyl; and Z is

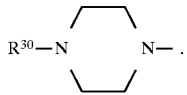

6. A compound of claim 1 wherein A is =N—O$R^1$.
7. A compound of claim 1 wherein A is =N—N($R^2$)($R^3$).
8. A compound of claim 1 wherein A is =C($R^{11}$)($R^{12}$).
9. A compound of claim 1 wherein A is =N$R^{25}$.
10. A compound of claim 5 wherein A is =N—O$R^1$.
11. A compound of claim 10 wherein X is —O—, —N$R^6$—, —N($R^6$)C(O)— or —C(O)N$R^6$—.
12. A compound of claim 10 wherein T is $R^4$-aryl.
13. A compound of claim 10 wherein Q is $R^5$-phenyl.
14. A compound of claim 10 wherein $R^{6a}$, $R^{7a}$, $R^{8a}$ and $R^{9a}$ are each H.
15. A compound of claim 1 wherein Q is $R^5$-phenyl, T is $R^4$-aryl, R is H, a is 1, A is =NO$R^1$, and

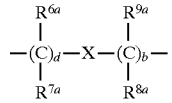

is —CH$_2$—O—CH$_2$, —CH$_2$—N($R^6$)C(O)—, —CH$_2$N$R^6$CH$_2$— or CH$_2$C(O)N$R^6$—.

16. A compound of claim 15 wherein T is $R^4$-phenyl and

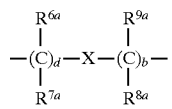

17. A compound of claim 15 wherein $R^1$ is H, alkyl, —(CH$_2$)n—G, —(CH$_2$)$_p$—M—(CH$_2$)$_n$—G or —C(O)N($R^6$)($R^7$), wherein M is —O— or —C(O)N($R^9$)— and G is —CO$_2R^6$, —O$R^6$, —C(O)N($R^6$)($R^9$), —C(=NO$R^8$)N($R^6$)($R^7$), —C(O)N($R^9$)($R^4$-heteroaryl) or $R^4$-heteroaryl.

18. A pharmaceutical composition comprising an effective amount of a compound of claim 1 and a pharmaceutically acceptable carrier.

19. A method of treating asthma, cough, bronchospasm, central nervous system diseases, inflammatory diseases and gastrointestinal disorders comprising administering an effective amount of a compound of claim 1 to a mammal in need of such treatment.

20. A compound of claim 1 selected from the group consisting of 119 120
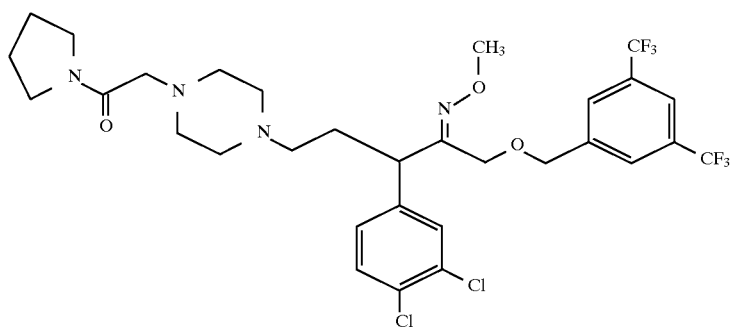
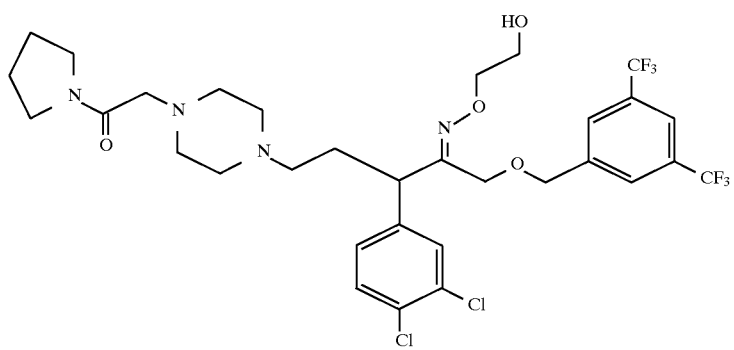
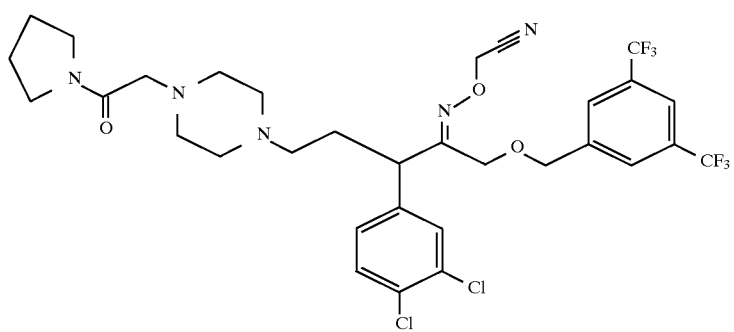
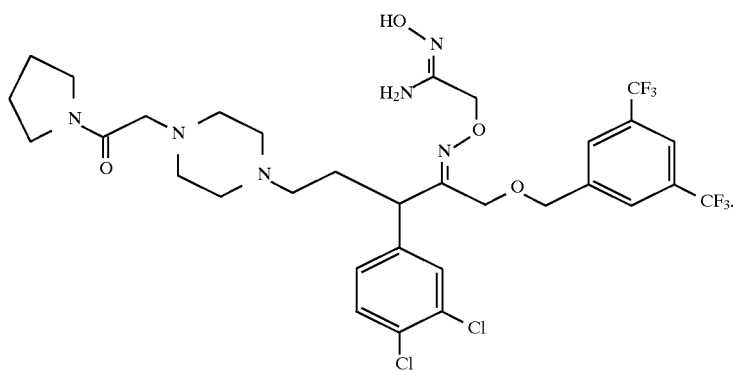
* * * * *